(12) United States Patent
Humphreys et al.

(10) Patent No.: US 10,562,966 B2
(45) Date of Patent: *Feb. 18, 2020

(54) ANTIBODIES OF THE CLASS IGG4

(75) Inventors: David Paul Humphreys, Berkshire (GB); Shirley Jane Peters, Berkshire (GB); Ralph Adams, Berkshire (GB); James Heads, Berkshire (GB)

(73) Assignee: UCB BIOPHARMA SPRL, Brussels (BE)

( * ) Notice: Subject to any disclaimer, the term of this patent is extended or adjusted under 35 U.S.C. 154(b) by 555 days.

This patent is subject to a terminal disclaimer.

(21) Appl. No.: 13/817,961

(22) PCT Filed: Aug. 19, 2011

(86) PCT No.: PCT/GB2011/051563
§ 371 (c)(1),
(2), (4) Date: Aug. 16, 2013

(87) PCT Pub. No.: WO2012/022982
PCT Pub. Date: Feb. 23, 2012

(65) Prior Publication Data
US 2013/0323236 A1    Dec. 5, 2013

(30) Foreign Application Priority Data

Aug. 20, 2010 (GB) .................................. 1014033.3

(51) Int. Cl.
*C07K 16/00* (2006.01)
*C12P 21/08* (2006.01)
*C07K 16/24* (2006.01)
*C07K 1/00* (2006.01)

(52) U.S. Cl.
CPC .................................. *C07K 16/24* (2013.01)

(58) Field of Classification Search
None
See application file for complete search history.

(56) References Cited

U.S. PATENT DOCUMENTS

| | | |
|---|---|---|
| 4,741,900 A | 5/1988 | Alvarez et al. |
| 4,816,397 A | 3/1989 | Boss et al. |
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbus et al. |
| 5,661,016 A | 8/1997 | Lonberg et al. |
| 5,667,425 A | 9/1997 | Pineau et al. |
| 5,677,425 A * | 10/1997 | Bodmer ................. C07K 16/30 530/350 |
| 5,698,426 A | 12/1997 | Huse |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,821,047 A | 10/1998 | Garrard et al. |
| 5,969,108 A | 10/1999 | McCafferty et al. |
| 6,331,415 B1 | 12/2001 | Cabilly et al. |
| 2008/0063635 A1 | 3/2008 | Takahashi et al. |
| 2013/0323236 A1 | 12/2013 | Humphreys |
| 2015/0017169 A1 | 1/2015 | Humphreys |

FOREIGN PATENT DOCUMENTS

| | | |
|---|---|---|
| EP | 0392745 | 10/1990 |
| EP | 0438474 | 7/1991 |
| EP | 0463151 | 1/1992 |
| EP | 0546073 B1 | 6/1993 |
| EP | 1810979 | 7/2007 |
| EP | 2194066 | 6/2010 |
| EP | 2 409 990 | 1/2012 |
| WO | WO8601533 | 3/1986 |
| WO | WO9002809 | 3/1990 |
| WO | WO9109967 | 7/1991 |
| WO | WO9110737 | 7/1991 |
| WO | WO9201047 | 1/1992 |
| WO | WO9202551 | 2/1992 |

(Continued)

OTHER PUBLICATIONS

Brekke et al. Immunologist 1994, 2:125-130.*
Murray et al. Harper's Biochemistry. 23rd Edition, 1993, Chapter 4:24-28.*
Schuurman et al. Molecular Immunology 2001, 38:1-8.*
Kohler, et al. Nature, 256:495-497 (1975).
Kozbor, et al., Immunology Today, 4:72-79 (1983).
Cole, et al., Monoclonal Antibodies and Cancer Therapy, pp. 77-96 (1985).
Babcook, J., et al. Proc. Natl. Acad. Sci., 93:7843-7848 (1996).
Brinkmann, et al., J. Immunol. Methods, 182:41-50 (1995).
Ames, et al., J. Immunol. Methods, 184:177-186 (1995).
Kettleborough, et al., Eur. J.Immunol., 24:952-958 (1994).
Persic, et al., Gene, 187:9-18 (1997).

(Continued)

*Primary Examiner* — Chun W Dahle
(74) *Attorney, Agent, or Firm* — McDonnell Boehnen Hulbert & Berghoff LLP

(57) ABSTRACT

The present invention provides an antibody of the class IgG4 comprising at least one heavy chain which comprises a $C_H1$ domain and a hinge region, wherein in each heavy chain: a. the inter-chain cysteine at position 127, numbered according to the Kabat numbering system, in the $C_H1$ domain is substituted with another amino acid; and b. one or more of the amino acids positioned in the upper hinge region is substituted with cysteine.

19 Claims, 46 Drawing Sheets

Specification includes a Sequence Listing.

(56) References Cited

FOREIGN PATENT DOCUMENTS

| WO | WO9218619 | 10/1992 |
|---|---|---|
| WO | WO9306231 | 4/1993 |
| WO | WO9311236 | 6/1993 |
| WO | WO9515982 | 6/1995 |
| WO | WO9520401 | 8/1995 |
| WO | WO9820734 | 5/1998 |
| WO | WO9825971 | 6/1998 |
| WO | WO8900195 | 1/1999 |
| WO | WO8901476 | 2/1999 |
| WO | WO9922583 | 5/1999 |
| WO | WO03031581 | 4/2003 |
| WO | 2004/003019 | 1/2004 |
| WO | WO2004051268 | 6/2004 |
| WO | WO05117984 | 12/2005 |
| WO | WO2007106120 | 9/2007 |
| WO | WO2004106377 | 12/2007 |
| WO | WO2008038024 | 4/2008 |
| WO | WO2008145142 | 12/2008 |
| WO | WO201063785 | 6/2010 |

OTHER PUBLICATIONS

Burton, et al., Advances in Immunology, 57:191-280 (1994).
Ward, et al., Nature, 341:544-546 (1989).
Orlandi, et al., Proc. Natl. Acad. Sci., 86:3833-3837 (1989).
Riechmann, et al., Nature, 332:323-327 (1988).
Bird, et al., Science, 242:423-426 (1988).
Mountain, et al., Biotechnol. Genet. Eng. Rev., 10:1-142 (1992).
Verma, et al., Journal of Immunological Methods, 216:165-181 (1998).
Angal, et al., Molecular Immunology, 30:105-108 (1993).
Harris, R.J., Journal of Chromatography, 705:129-134 (1995).
Hellstrom, et al., Controlled Drug Delivery, pp. 623-653 (1987).
Thorpe, et al., Immunol. Rev., 62:119-58 (1982).
Dubowchik, et al., Pharmacology and Therapeutics, 83:67-123 (1999).
Chapman, Advanced Drug Delivery Reviews, 54:531-545 (2002).
Schuurman, et al., Molecular Immunology, 38:1-8 (2001).
Lu, et al., Journal of Pharmaceutical Sciences, 97:960-969 (2008).
Aalberse, et aL, Immunology, 105:9-19 (2002).
Bloom, et al., Protein Science, 6:407-415 (1997).
Schuurman, et al., Immunology, 97-693-698 (1999).
Wypych, et al., J. Biol. Chem., 283:16194-16205 (2008).
LeFranc, et al. Dev. Comp. Immunol., 29:185-203 (2005).
Smith-Gill et al., J.Immunol. 139:4135-4144, (1987).
Kumar et al., J. Biol. Chem. 275:35129-35136, (2000).
Song et al., Biochem Biophys Res Comm 268:390-394 (2000).
Silva et al., J. Biol. Chem. 290(9):5462-5469 (Feb. 27, 2015).
Kolfschoten et al., "Anti-inflammatory activity of human IgG4 antibodies by dynamic Fab arm exchange," Science, 2007, 317(5844), 1554-1557.
Brekke et al., "Structure-Function Relationships of Human IgG", Immunologist, 1994, vol. 2, 125-130.
Ibragimova et al, "Stability of the Beta-Sheet of the WW Domain: A Molecular Dynamics Simulation Study," Biophysical Journal, 1999, vol. 77, 2191-2198.
Dufner et al., "Harnessing phage and ribosome display for antibody optimisation," Trends in Biotechnology, 2006, 24(11) 523-529.
Salfeld, J.G., "Isotype selection in antibody engineering," Nature biotechnology, 2007, 25(12) 1369-1372.
Dall-Acqua et al., "Modulation of the Effector Functions of a Human IgG1 through Engineering of its Hinge Region," The Journal of Immunology, 2006, vol. 177, 1129-1138/.
Non-Final Office Action dated Aug. 29, 2016, issued in connection with U.S. Appl. No. 14/380,310, filed Aug. 21, 2014, 15 pages.
Final Office Action dated Apr. 29, 2016, issued in connection with U.S. Appl. No. 14/380,310, filed Aug. 21, 2014, 15 pages.
Non-Final Office Action dated Oct. 16, 2015, issued in connection with U.S. Appl. No. 14/380,310, filed Aug. 21, 2014, 20 pages.
Restriction Requirement dated Jun. 10, 2015, issued in connection with U.S. Appl. No. 14/380,310, filed Aug. 21, 2014, 7 pages.
Restriction Requirement dated Jun. 2, 2015 issued in connection with U.S. Appl. No. 14/380,309, filed Aug. 21, 2014, 7 pages.
Non-Final Office Action dated Nov. 13, 2015, issued in connection with U.S. Appl. No. 14/380,309, filed Aug. 21, 2014, 19 pages.
Non-Final Office Action dated Sep. 22, 2016, issued in connection with U.S. Appl. No. 14/380,309, filed Aug. 21, 2014, 25 pages.
Final Office Action dated Mar. 28, 2017, issued in connection with U.S. Appl. No. 14/380,309, filed Aug. 21, 2014, 19 pages.
Non-Final Office Action dated Aug. 31, 2017, issued in connection with U.S. Appl. No. 14/380,309, filed Aug. 21, 2014, 19 pages.
Final Office Action dated Jan. 29, 2018, issued in connection with U.S. Appl. No. 14/380,309, filed Aug. 21, 2014, 14 pages.

* cited by examiner

Figure 1a

IgG1 wild type CH1 & hinge

(A)STKGPSVFPLAPSSKSTSGGTAALGCLVKDYFPEPVTVSWNSGALTSGVHTFPAVLQSSGLYSLSSVVTVPSSSLGTQTYICNVNHKPSNTKV
DKRV(E)PKSCDKTHTCPPCPAPELLGGP     (SEQ ID NO:1)

IgG4 wild type CH1 & hinge

(A)STKGPSVFPLAPCSRSTSESTAALGCLVKDYFPEPVTVSWNSGALTSGVHTFPAVLQSSGLYSLSSVVTVPSSSLGTKTYTCNVDHKPSNTKV
DKRV(E)SKYGPPCPSCPAPEFLGGP     (SEQ ID NO:2)

Ig wild type kappa constant light chain

TVAAPSVFIFPPSDEQLKSGTASVVCLLNNFYPREAKVQWKVDNALQSGNSQESVTEQDSKDSTYSLSSTLTLSKADYEKHKVYACEVTHQGLSSP
VTKSFNRGEC  (SEQ ID NO:60)

| Light chain | $C_L$ | | | |
|---|---|---|---|---|
| Human κ | ENRGEC (SEQ ID NO:3) | | | |

| Heavy chain | $C_H1$ (N-term) | UPPER | CORE | LOWER |
|---|---|---|---|---|
| Human IgGγ1 | LAPSSKSTS (SEQ ID NO:4) | EPKSCDKTHT (SEQ ID NO:5) | CPPCP | APELLGGP |
| Human IgGγ2 | LATCSRSTS (SEQ ID NO:6) | ERK | CCVECPPCP | APPVA GP |
| Human IgGγ3 | LAPCSRSTS (SEQ ID NO:8) | ELKTPLGDTTHT (SEQ ID NO:7) | CPRCP (EPKSCDTPPPCPRCP)₃ (SEQ ID NO:9) | APELLGGP |
| Human IgGγ4 | LAPCSRSTS↑C427 (SEQ ID NO:10) | ESKYGPP↑G230 (SEQ ID NO:11) | CPSCP↑↑C239 C242 | APEFLGGP |

| Heavy chain | $C_H1$ (N-term) | Hinge | | |
|---|---|---|---|---|
| Human IgD | LTSGCRHPK (SEQ ID NO:67) | (q) SPKAQASSVPTAQPQAEGSLAKATTAPATTRNT (SEQ ID NO:68) | | |

| Heavy chain | $C_H1$ (C-term) | $C_H2$ (N-term) | | |
|---|---|---|---|---|
| Human IgM | LVSDSSPS (SEQ ID NO:69) | EKNVPLP (SEQ ID NO:70) | (v) LABLPPKVSV (SEQ ID NO:71) | |

| | CH1 | | | | | | | HINGE | | | | | | | | | |
|---|---|---|---|---|---|---|---|---|---|---|---|---|---|---|---|---|---|
| EU Numbering for IgG1 | 131 | 216 | 217 | 218 | 221 | | | 222 | 223 | 224 | 225 | 226 | 227 | 228 | 229 | 230 |
| Kabat Numbering for IgG1 | 127 | 226 | 227 | 228 | 232 | 233 | 234 | 235 | 236 | 237 | 238 | 239 | 240 | 241 | 242 | 243 |
| IMGT Numbering for IgG1 | 10 | 1 | 2 | 3 | 4 | 5 | 6 | 7 | 8 | 9 | 10 | 11 | 12 | 13 | 14 | 15 |
| IgG1 wt residues | S | E | P | K | S | C | D | K | T | H | T | C | P | P | C | P |
| EU Numbering for IgG4 | 131 | 216 | 217 | 218 | 219 | 220 | 224 | 225 | | | | 226 | 227 | 228 | 229 | 230 |
| Kabat Numbering for IgG4 | 127 | 226 | 227 | 228 | 229 | 230 | 237 | 238 | | | | 239 | 240 | 241 | 242 | 243 |
| IMGT Numbering for IgG4 | 10 | 1 | 2 | 3 | 4 | 5 | 6 | 7 | | | | 8 | 9 | 10 | 11 | 12 |
| IgG4 wt residues | C | E | S | K | Y | G | P | P | | | | C | P | S | C | P |
| Mutations to IgG4 | S | | C or P | C | C or S | C | D or A | K or A | A or T or G | A or H or G | A or T or G | S | P | P | C | S |

Figure 2b

|  | CH1 | HINGE | | | | | | |
|---|---|---|---|---|---|---|---|---|
| Kabat Numbering | 127 | 226 | 227 | 228 | 229 | 230 | 232 | 233 |
| IMGT Numbering for IgG3 | 10 | 1 | 2 | 3 | 4 | 5 | 6 | 7 |
| IgG3 wt residues | C | E | L | K | T | P | L | G |
| Mutations to IgG3 | S | C | C | C | C | C | C | C |

Figure 2c

|  | CH1 | | | | CH2 | | |
|---|---|---|---|---|---|---|---|
| Kabat numbering for IgM | 127 | 223 | 223A | 223B | 223C | 243G | 243H | 243I |
| IMGT Numbering for IgM | 10 | 121 | 122 | 123 | 124 | 1.5 | 1.4 | 1.3 |
| IgM wt residues | C | V | P | L | P | V | I | A |
| Mutations to IgM | S | C | C | C | C | C | C | C |

Figure 2d

|  | CH1 | Hinge | | | | | | |
|---|---|---|---|---|---|---|---|---|
| Kabat numbering for IgD | 128 | 227 | 228 | 229 | 230 | 231 | 232 | 233 |
| IMGT Numbering for IgD | 11 | 1 | 2 | 3 | 4 | 5 | 6 | 7 |
| IgD wt residues | C | E | S | P | K | A | Q | A |
| Mutations to IgD | S | C | C | C | C | C | C | C |

Figure 3a

| Mutations to HC IgG4 | G4 | G1 | 1 | 2 | 3 | 6 | 7 | 8 | 12 | 13 | 15 | 16 |
|---|---|---|---|---|---|---|---|---|---|---|---|---|
| C127S | | | * | | | | | | | | | |
| C230C | | | | * | * | * | * | * | | | * | * |
| C239S | | | | | | * | * | * | | | * | * |
| S241P | | | | * | | | | | * | | | * |
| C242S | | | | | * | | | | | * | | |

Figure 3b

| HC Cys position | G4 | G1 | 1 | 2 | 3 | 6 | 7 | 8 | 12 | 13 | 15 | 16 |
|---|---|---|---|---|---|---|---|---|---|---|---|---|
| 127 | LC | | | | | | | | | | | |
| 230 (G4) 233 (G1) | | LC | LC or HC | LC | LC | LC | LC | LC | LC | LC | LC | LC |
| 239 | HC | HC | LC or HC | | | HC | HC | | | HC | HC or LC | HC or LC |
| 242 | HC | HC | | LC | | | | | | | HC or LC | HC or LC |

Figure 4a

| Mutations to G4 | G4 | G1 | 28 | 28P | 29 | 30 | 31 | 32 | 33 | 34 | 35 | 36 | 37 | 38 | 39 | 44 | 45 | 46 | 47 |
|---|---|---|---|---|---|---|---|---|---|---|---|---|---|---|---|---|---|---|---|
| C127S | | | * | * | * | * | * | * | * | * | * | * | * | * | * | * | * | * | * |
| S227C | | | | | | | | | | | | * | * | * | * | | | | |
| K228C | | | | | | | | | | | | | | | | | | | |
| Y229C | | | * | * | * | | | * | * | * | * | | | | | | | | |
| Q230C | | | | | | * | * | | | | | | | | | | | | |
| P238PAAA | | | | * | | | | | | | | | | | | | | | |
| C239S | | | | | | | * | | * | * | * | | * | | | * | * | * | * |
| S241P | | | | | | | | | | | | | | | | * | * | | |
| C242S | | | * | | | * | | | | | * | | | * | * | | * | * | * |

ANTIBODIES

Figure 4b

| HC Cys position | G4 | G1 | 28 | 29 | 30 | 31 | 32 | 33 | 34 | 35 | 36 | 37 | 38 | 39 | 44 | 45 | 46 | 47 |
|---|---|---|---|---|---|---|---|---|---|---|---|---|---|---|---|---|---|---|
| 127 | LC | | | | | | | | | | | | | | | | | |
| 227 | | LC | | | | | | LC | LC | LC | LC or HC | LC | LC | LC | | | LC | LC |
| 228 | | | LC or HC | LC | LC | LC | LC or HC | | | | | | | | | | | |
| 229 (34) | | | | | | | | | | | | | | | LC or HC | LC | LC | |
| 230 (34) 233 (G1) | | LC | HC or LC | HC | HC | | HC or LC | HC | HC | | HC or LC | HC | HC | | HC or LC | HC or LC | HC | |
| 239 | HC | HC | LC or HC | | | | HC or LC | | | | | | | | | | | |
| 242 | HC | HC | | | | | | | | | | | | | | | | |

Figure 5

(Ab 6) (SEQ ID NO:12)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) SKYGPPSPCPSSPAPEFLGGP (Ab 7) (SEQ ID NO:13)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) SKYCPPCPSSPAPEFLGGP (Ab 8) (SEQ ID NO:14)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) SKYCPPSPCPSSPAPEFLGGP (Ab 15) (SEQ ID NO:15)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) SKYCPPCPSCPAPEFLGGP (Ab 16) (SEQ ID NO:16)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) SKYCPPCPCPSCPAPEFLGGP (Ab 28) (SEQ ID NO:17)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) SKCGPPCPSCPAPEFLGGP (Ab 29) (SEQ ID NO:18)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) SKCGPPSPSCPAPEFLGGP

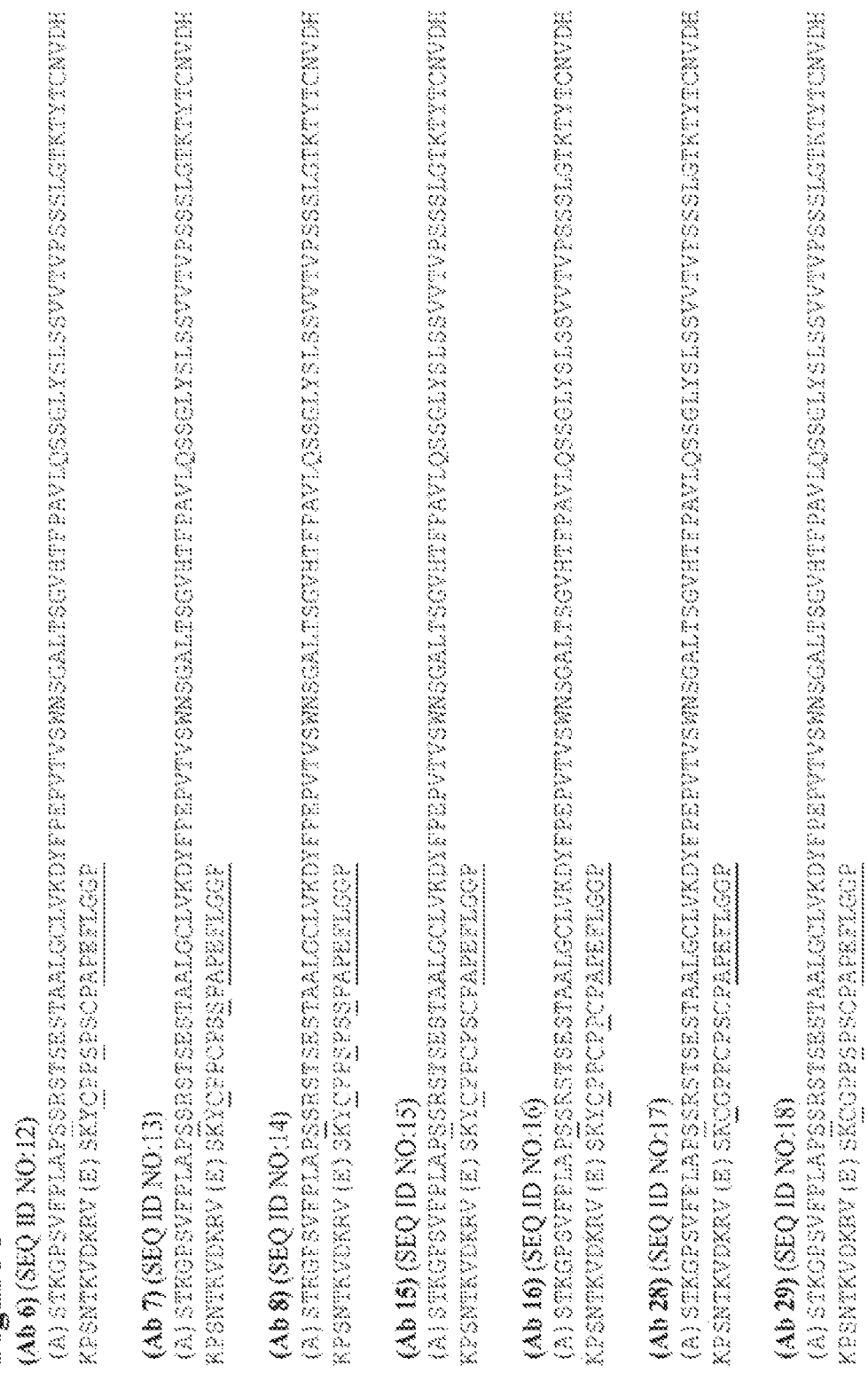

Figure 5, Continuation (Ab 30) (SEQ ID NO:19)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SKCGPPCPSSPAPEFLGGP (Ab 31) (SEQ ID NO:20)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SKCGPPSPSPAPEFLGGP (Ab 32) (SEQ ID NO:21)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SCYGPPCPSCPAPEFLGGP (Ab 33) (SEQ ID NO:22)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SCYGPPSPSPAPEFLGGP (Ab 34) (SEQ ID NO:23)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SCYGPPCPSSPAPEFLGGP (Ab 35) (SEQ ID NO:24)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SCYGPPSPSCPAPEFLGGP (Ab 36) (SEQ ID NO:25)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) CKYGPPCPSCPAPEFLGGP (Ab 37) (SEQ ID NO:26)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) CKYGPPSPSCPAPEFLGGP Figure 5, Continuation (Ab 38) (SEQ ID NO:27)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) CRYCPCPSSPAPEPLGGP (Ab 39) (SEQ ID NO:28)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) CRYGPPSPSPAPEPLGGP (Ab 44) (SEQ ID NO:29)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SKYCPPAAACPSCPAEELGGP (Ab 45) (SEQ ID NO:30)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SKYCPPAAASPSCPAEELGGP (Ab 46) (SEQ ID NO:31)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SKYCPPAAACPSSPAPEPLGGP (Ab 47) (SEQ ID NO:32)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SKYCPPAAASPSSPAPEPLGGP (Ab 2) (SEQ ID NO:33)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (B) SKYGPPSPSCPAPEFLGGP Figure 5, Continuation (Ab 3) (SEQ ID NO:34)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) SKYGPPCPSSPAPEFLGGP (Ab 48) (SEQ ID NO:35)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) PRSCDKTHTCPPCPAPEFLGGP (Ab 28P) (SEQ ID NO:36)
(A) STKGPSVFPLAPSSRSTSESTAALGCLVKDYFPEPVTVSWNSGALTSGVHTFPAVLQSSGLYSLSSVVTVPSSSLGTKNTYTCNVDH KPSNTKVDKRV (B) SKCGPPCPPCPAPEFLGGP (Ab 44P) (SEQ ID NO:37)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (B) SKYCPPAAACPPCPAPEFLGGP

Figure 6

IgG4 CH2 and CH3: (SEQ ID NO:64)
SVFLFPPKPKDTLMISRTPEVTCVVVDVSQEDPEVQFNWYVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDIAVEWESNGQPENNYKTTPPVLDSDGSFFLYSRLTVDKSR
WQEGNVFSCSVMHEALHNHYTQKSLSLSLGK IgG4 CH2 IgG1 CH3: (SEQ ID NO:65)
SVFLFPPKPKDTLMISRTPEVTCVVVDVSQEDPEVQFNWYVDGVEVHNAKTKPREEQFNSTYRVVSVLTVLHQDWLNGKEYKCKVSNKG
LPSSIEKTISKAKGQPREPQVYTLPPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGK (Ab 6) (SEQ ID NO:38)
(A) STKGPSVFPLATSSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPCPSCPAFEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 7) (SEQ ID NO:39)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPCPSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 8) (SEQ ID NO:40)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPSPSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK Figure 6, Continuation (Ab 15) (SEQ ID NO:41)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E)SKYGPPCPSCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK (Ab 16) (SEQ ID NO:42)
(A) STKGPSVFPLAPSSRSTSESTAALGCLVKDYFPEPVTVSWNSGALTSGVHTFPAVLQSSGLYSLSSVVTVPSSSLGTTTYTCNVDH KPSNTKVDKRV(E)SKYGPPCPPCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK (Ab 28) (SEQ ID NO:43)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E)SKCGPPCPSCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK (Ab 29) (SEQ ID NO:44)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E)SKCGPPSCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK (Ab 30) (SEQ ID NO:45)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E)SKCGPPCPSCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK Figure 6, Continuation (Ab 31) (SEQ ID NO:46)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (E) SKCGPSPSPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK (Ab 32) (SEQ ID NO:47)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (E) SCVGPCPSCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK (Ab 33) (SEQ ID NO:48)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (E) SCVGPCPSCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK (Ab 34) (SEQ ID NO:49)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (E) SCVGPCPSCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK (Ab 35) (SEQ ID NO:50)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (E) SCVGPCPSCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK Figure 6, Continuation (Ab 36) (SEQ ID NO:51)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)CKYGPFCPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 37) (SEQ ID NO:52)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)CKYGPFCPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 38) (SEQ ID NO:53)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)CKYGPFCPSSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKCQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 39) (SEQ ID NO:54)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)CKYGPPSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 40) (SEQ ID NO:55)
(A) STKGPSVFPLAPSSRSTSESTAALGCPSCPAAACPSCPAPEFLGGPSVFLFPPKPKDTLMISRTPEVTCVVVDVSQEDPEVQFNWYVDGVEVHNAKTKF
REEQFNSTYRVSVLTVLHQDWLNGKEYKCAVSNKGLPSSIEKTISKAKGQPREPQVVTLPPSQEEMTKNQVSLTCLVKGFYPSDIAVE
WESNGQPENNYKTTPPVLDSDGSFFLYSRLTVDKSRWQEGNVFSCSVMHEALHNHYTQKSLSLSLGK Figure 6, Continuation (Ab 45) (SEQ ID NO:56)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E)SKYGPPAAASPSCPAPEFLGGPSVFLFPPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQQGNVFSCSVMHEALHNHYTQKSLSLSLGK (Ab 46) (SEQ ID NO:57)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E)SKYCPPAAACPSCPAPEFLGGPSVFLFPPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQQGNVFSCSVMHEALHNHYTQKSLSLSLGK (Ab 47) (SEQ ID NO:58)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E)SKYCPPAAASPSCPAPEFLAGTSVFLFPPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQQGNVFSCSVMHEALHNHYTQKSLSLSLGK (Ab 2) (SEQ ID NO:59)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E)SKYGPPCPSCPAPEFLGGPSVFLFPPKPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQPREPQVYTLPPSQEEMTKNQVSLTCLVKGFYPSDIAVEW ESNGQPENNYKTTPPVLDSDGSFFLYSRLTVDKSRWQQGNVFSCSVMHEALHNHYTQKSLSLSLGK (Ab 3) (SEQ ID NO:60)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E)SKYGPPCPSCPAPEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPREPQVYTLPPSQEEMTKNQVSLTCLVKGFYPSDIAVEWE SNGQPENNYKTTPPVLDSDGSFFLYSRLTVDKSRWQQGNVFSCSVMHEALHNHYTQKSLSLSLGK Figure 6, Continuation (Ab 48P) (SEQ ID NO:61)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (E) PKSCIKTHTCPPCPAPEFLGGPSVFLFPPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHNHYTQKSLSLSLGK (Ab 28P) (SEQ ID NO:62)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKHV (E) SKCGPPCPPCPAPEFLGGPSVFLFPPKPKDTLMISRTPEVTCVVVDVSQEDPEVQFNWYVDGVEVHNAKTKPEE QFNSTYRVVSVLTVLHQDWLNGKEYKCKVSNKGLPSSIEKTISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHEALHNHYTQKSLSLSLGK (Ab 44P) (SEQ ID NO:63)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV (E) SKYCPPAAACPCPAACPCFAEELGGTSVFLFPKPKDTLMISRTPEVTCVVVDVSQEDPEVQFNWYDGVEVHNAKTKP REEQFNSTYRVVSVLTVLHQDWLNGREYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHNHYTQKSLSLSLGK

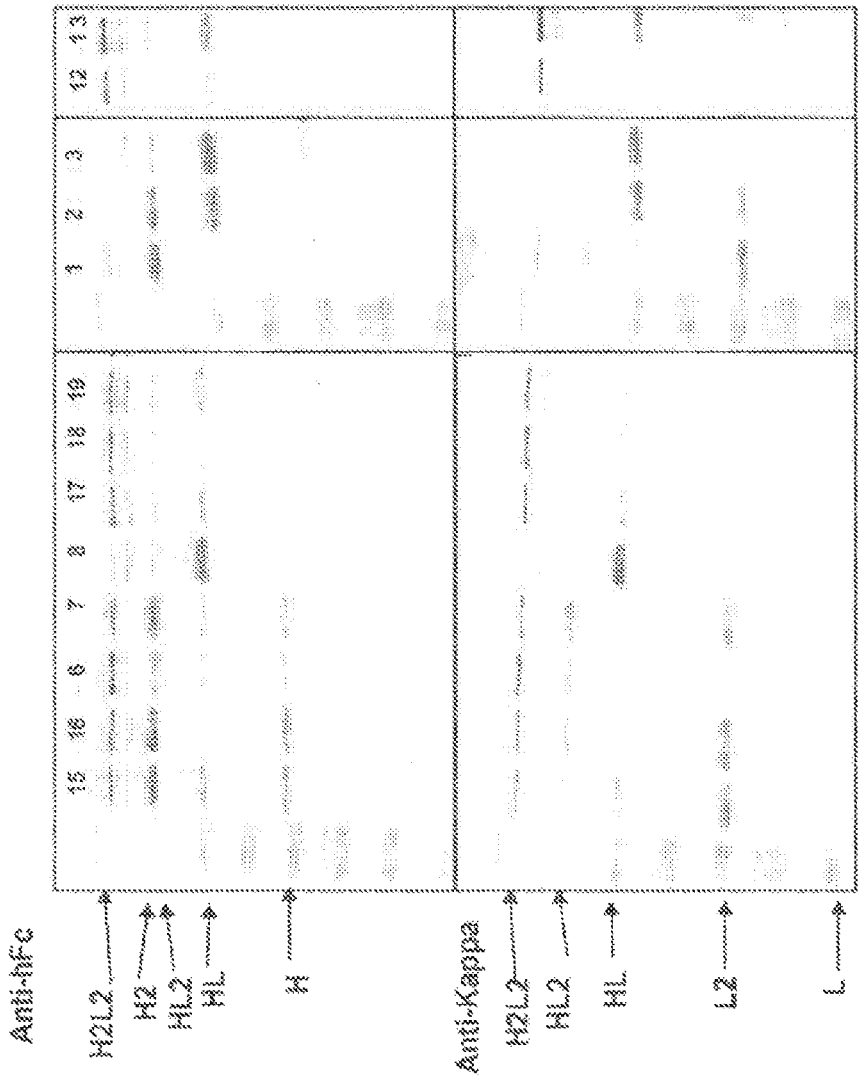

Figure 16

| Antibody | $k_a$ (M$^{-1}$s$^{-1}$) | $k_d$ (s$^{-1}$) | $K_D$ (M) | KD (pM) |
|---|---|---|---|---|
| Control | | | | |
| 17 (hg4 wt) | 3.03E+06 | 2.41E-04 | 7.95E-11 | 80 |
| 18 (hg4 S241P) | 2.65E+06 | 2.51E-04 | 9.47E-11 | 95 |
| 19 (hG1 wt) | 2.77E+06 | 3.54E-04 | 1.28E-10 | 128 |
| 17 (hg4 wt) | 2.87E+06 | 3.26E-04 | 1.14E-10 | 114 |
| Mutants | | | | |
| 15 (C127S G233C) | 3.13E+06 | 2.73E-04 | 8.72E-11 | 87 |
| 16 (C127S G233C S241P) | 2.83E+06 | 3.54E-04 | 1.25E-10 | 125 |
| 6 (C127S G233C C239S) | 2.89E+06 | 3.32E-04 | 1.15E-10 | 115 |
| 7 (C127S G233C C242S) | 2.98E+06 | 2.95E-04 | 9.90E-11 | 99 |
| 8 (C127S G233C C239S C242S) | 2.71E+06 | 2.62E-04 | 9.67E-11 | 97 |

Figure 18

Alternative Ala spacer lengths

17. IgG4 wt
15. C127S G230C
49. C127S G230C ^A
50. C127S G230C ^AA
44. C127S G230C ^AAA
51. C127S G230C ^AAAAA
52. C127S G230C ^AAAAAA
19. IgG1 wt

Altering the spacer length does not influence the migration pattern observed on a gel

* Fab stability °C

Figure 21

Replacing PP with IgG1 residues, DKTHT and truncations thereof

17. IgG4 wt
15. C127S G230C

68. C127S G230C ^DK

67. C127S G230C ^DKT

66. C127S G230C ^DKTH

56. C127S G230C ^DKTHT

19. IgG1 wt

* Fab stability °C

Figure 25 MCF7

Figure 28 Expression

Figure 29 Expression

Figure 30 Expression

ANTIBODIES OF THE CLASS IGG4

This application is a national phase entry of International Application No. PCT/GB2011/051563, filed Aug. 19, 2011, which claims the benefit of Great Britain Application No. 1014033.3, filed Aug. 20, 2010, the disclosures of which are incorporated by reference herein.

The present invention relates to an improved antibody having an altered arrangement of disulphide bonds compared to a wild type antibody and a method to produce the improved antibody.

The biopharmaceutical industry encompassing recombinant proteins, monoclonal antibodies (mAbs) and nucleic acid-based drugs is growing rapidly. Antibody engineering has resulted in the design and production of antibody fragments or alternative formats. Preferred molecular format along with other aspects such as production yield, protein quality and storage stability are taken into consideration when selecting an antibody-based protein as a therapeutic agent.

The basic structure of all immunoglobulin (Ig) molecules comprises two identical heavy chains (HCs) and two identical light chains (LCs) which are coupled by disulphide bonds. Each LC consists of a variable ($V_L$) and constant domain ($C_L$). Based on the HC, five main Ig classes are recognized: IgG, IgA, IgD, IgE and IgM. For IgG, the HC consists of one variable domain ($V_H$) and three constant domains ($C_H$1-3). The $C_H$2 and $C_H$3 domains form the Fc part of the molecule that is responsible for stimulating effector function and is linked to the Fab fragment ($V_H V_L$ and $C_H C_L$) by a hinge region which confers flexibility to the IgG molecule. Two antigen recognition sites are located at the ends of the $V_L$ and $V_H$ domains. IgG is further subdivided into 4 different isotypes: IgG1, IgG2, IgG3 and IgG4.

Fc-mediated effector functions i.e. antibody dependent cytotoxicity (ADCC) or complement dependent cytotoxicity (CDC) are isotype dependent. Each isotype has evolved to perform a specific function within the body. The IgG1 isotype is currently the most widely used as a therapeutic due to its extended half-life, enhanced ADCC activation and complement activation. Other isotypes are considered as therapeutic agents dependant on the target and desired effect. For instance, when target antigens are simply to be neutralized and effector functions are less important, alternative isotypes such as IgG2 and IgG4 can be used. Alternatively, IgG with re-engineered Fc/effector function may be considered.

IgG2 also has minimal associated effector function but is prone to dimerisation which is not fully understood. IgG4 remains a useful isotype because of its relative lack of effector function induction. However, IgG4 also has some inherent practical difficulties namely its propensity to form half antibody, its ability to exchange half molecules and its shorter serum half life.

In vitro, IgG4 molecules conform to the prototypical IgG structure, but in vivo they have been observed to form half-molecules each comprising a single light chain and a single heavy chain caused by formation of intra heavy chain disulphide bonds within the hinge. A large percentage of circulating IgG4 have been observed to be bispecific, but functionally monovalent. This is because the half-molecule can form IgG4 with other IgG4 half-molecules (Schuurman, J., Van Ree, R., Perdok, G. J., Van Doorn, H. R., Tan, K. Y., Aalberse, R. C., 1999. Normal human immunoglobulin G4 is bispecific: it has two different antigen-combining sites. Immunology 97, 693-698).

The formation of half molecules of IgG4 can be reduced by introduction of a Ser to Pro mutation at position 241 (numbered according to the Kabat numbering system) in the hinge (Angal, S. et al., 1993. A single amino acid substitution abolishes the heterogeneity of chimeric mouse/human (IgG4) antibody. Mol Immunol 30, 105-108). In addition, this point mutation did not influence the compact structure of IgG4 thereby allowing IgG4 to retain its reduced ability to activate complement.

Following the discovery of the S241P mutation, further mutations to IgG4 have been investigated in order to understand the inter-heavy chain interaction in IgG4 antibodies, reduce IgG4 effector function and enhance structural stability. In Schuurman et al. (Schuurman, J et al., 2001. The inter-heavy chain disulphide bonds of IgG4 are in equilibrium with intra-chain disulphide bonds. Molecular Immunology 38, 1-8), the observed instability of inter-heavy chain disulphide bonds of IgG4 was investigated using IgG4 mutants. In mutant M1 Cys 131 (numbered according to EU numbering system or Cys 127 according to Kabat numbering system), which is involved in the inter-heavy-light chain ($C_L$-$C_{H1}$) disulphide bond, was replaced by serine and it was found that this mutant resulted in the formation of dimers of light chains and dimers of heavy chains. In mutant M2 cysteine 226 (226 numbered according to EU numbering system or 239 according to Kabat numbering system), which is involved in an inter-heavy chain disulphide bond in the hinge, was replace by serine and it was found that this mutant had a more stable inter-heavy chain linkage compared to IgG4 and prevents the formation of an intra-heavy chain disulphide bond.

Mutations in the $CH_2$ and $CH_3$ domains of IgG4 antibodies have also been investigated in order to reduce the formation of aggregates of IgG4 antibodies. US 2008/0063635 Takahashi et al. has investigated a mutant of IgG4 in which arginine at position 409 (409 numbered according to EU numbering system or 440 numbered according to the Kabat numbering system) in the CH3 domain is substituted with lysine, threonine, methionine or leucine in order to inhibit aggregate formation at low pH. Further mutations at L235, D265, D270, K322, P329 and P331 (L235, D265, D270, K322, P329 and P331 numbered according to EU numbering system or L248, D278, D283, K341, P348 and P350 numbered according to the Kabat numbering system) are also taught in order to attenuate CDC activity. WO2008/145142 Van de Winkel et al. discloses stable IgG4 antibodies that have a reduced ability to undergo Fab-arm exchange by substitution of the arginine residue at position 409, the Phe residue at position 405 or the Lys at position 370 (R409, F405 and K370 numbered according to EU numbering system or R440, F436 and K393 numbered according to the Kabat numbering system) even in the absence of the S228P (S228 numbered according to EU numbering system or S241 according to the Kabat numbering system) mutation in the hinge region.

The alteration of the number of cysteine residues present in the hinge region of antibodies has been previously investigated. U.S. Pat. No. 5,677,425 Bodmer et al. discloses that the number of cysteine residues in the hinge region may be increased in order to facilitate the use of the cysteine thiol groups for attaching effector or reporter molecules. U.S. Pat. No. 5,677,425 also teaches that the number of cysteine residues in the hinge region may be reduced to one in order to facilitate the assembly of the antibody molecules, since it will only be necessary to form a single disulphide bond, which will provide a specific target for attaching the hinge region either to another hinge region or to an effector or reporter molecule.

However, there is still a need to provide new antibodies having improved properties which makes them even more suitable for use as a therapeutic. The present invention provides new mutant antibodies which have advantageous properties including improved biophysical properties compared to wild-type antibodies. In particular it has been surprisingly found that modification of the position of the cysteine residue in the heavy chain of an IgG4 antibody which forms a disulphide bond with a cysteine in the light chain provides an IgG4 antibody having improved stability compared to a wild-type IgG4 antibody.

SUMMARY OF THE INVENTION

In one aspect, the present invention provides an antibody of the class IgG4 comprising at least one heavy chain which comprises a $C_H1$ domain and a hinge region, wherein in each heavy chain:
  a. the inter-chain cysteine at position 127, numbered according to the Kabat numbering system, in the $C_H1$ domain is substituted with another amino acid; and
  b. one or more of the amino acids positioned in the upper hinge region is substituted with cysteine.

The cysteine in the $C_H1$ domain which forms an inter-chain disulphide bond with a cysteine in a light chain is the cysteine at position 127, numbered according to the Kabat numbering system, is shown in FIG. 1b.

Changing the position of the disulfide bond in the IgG4 constant region results in a higher Tm being observed for the Fab domain. The temperature at which 50% of the protein is unfolded is designated the Tm. Experimentally, the Tm is determined as the inflection point of, for example the fluorescence-vs.-temperature curve (i.e. the temperature where the fluorescence-vs.-temperature curve is the steepest).

Thus a higher Tm infers a higher thermal stability. Thus the molecules of the present disclosure have a higher thermal stability.

Whilst not wishing to be bound by theory this may be as result of reduction of strain or internal tension in the disulphide bond or polypeptide molecules obtained.

Further improvements in thermal stability can also be obtained by the introduction of further modifications into the IgG4 constant region.

The one or more amino acids positioned in the upper hinge region which are substituted with cysteine may be selected from 226, 227, 228, 229, 230, 237 and 238, numbered according to the Kabat numbering system, as shown in FIG. 1b (underlined amino acids in upper hinge region.

In a preferred embodiment the one or more amino acids positioned in the upper hinge region which are substituted with cysteine are one or more of the amino acids at positions selected from 227, 228, 229 and 230, numbered according to the Kabat numbering system, as shown in FIGS. 1b and 2a. In this latter arrangement then formation of the interchain (light chain-heavy chain) disulfide bond is in a position analogous to the disulfide bridge found in IgG1 constant regions.

The present inventors have established that IgG1 have higher thermal stability than IgG4 molecules in the Fab and Fc domains. However, the present disclosure allows the provision of an IgG4 molecule without ADCC effector function but with the thermal stability and/or other advantageous properties so an IgG1 molecule.

There appears to be three general aspects which influence the stability of the Fab domain in IgG4 molecule formed. The first is the position of the disulfide bridge. The second is the environment proximal to the disulfide bridge, that is to say the nature of the residues around the disulfide bond and the third is the length of the upper hinge region.

Thus present invention also provides an IgG4 antibody comprising a heavy chain with an upper hinge, core and lower hinge, and said upper hinge and core in the heavy chain or each heavy chain therein is 13 to 17, such as 15 amino acids in length.

In one embodiment the IgG4 antibody has an upper hinge and core of 15 amino acids in length.

In one embodiment the upper hinge and core comprises the natural 12 amino acids found in an IgG4 hinge and a further three amino acids, for example 3 alanine residues, or 3 glycine residues or a combination thereof.

In one embodiment the hinge has the one of the following sequences:

ESKYGPPAAACPSCP SEQ ID No: 72

ESKYGPPGGGCPSCP SEQ ID No: 73

ESKYGPPTHTCPSCP SEQ ID No: 74

ESKYGDKTHTCPSCP SEQ ID No: 75

EPSKYGPPAAACPSCP SEQ ID No: 76

EPSKYGPPGGGCPSCP SEQ ID No: 77

EPSKYGPPTHTCPSCP SEQ ID No: 78

EPSKYGDKTHTCPSCP SEQ ID No: 79

ESKSYGPPAAACPSCP SEQ ID No: 80

ESKSYGPPGGGCPSCP SEQ ID No: 81

ESKSYGPPTHTCPSCP SEQ ID No: 82

ESKSYGDKTHTCPSCP SEQ ID No: 83

ESKYGPPAAACPPCP SEQ ID No: 84

ESKYGPPGGGCPPCP SEQ ID No: 85

ESKYGPPTHTCPPCP SEQ ID No: 86

ESKYGDKTHTCPPCP SEQ ID No: 87

EPSKYGPPAAACPPCP SEQ ID No: 88

EPSKYGPPGGGCPPCP SEQ ID No: 89

EPSKYGPPTHTCPPCP SEQ ID No: 90

-continued

EPSKYGDKTHTCPPCP SEQ ID No: 91

ESKSYGPPAAACPPCP SEQ ID No: 92

ESKSYGPPGGGCPPCP SEQ ID No: 93

ESKSYGPPTHTCPPCP SEQ ID No: 94

ESKSYGDKTHTCPPCP SEQ ID No: 95

In one embodiment the upper hinge and core in the IgG4 molecule of the disclosure consists a natural IgG1 hinge i.e. EPKSCDKTHTCPPC SEQ ID No: 96 or a derivative thereof such as:

EPKSCDKAAACPPCP SEQ ID No: 97

EPKSCDKGGGCPPCP SEQ ID No: 98

EPKSCDKTHTSPPCP SEQ ID No: 99

EPKSCDKTHTCPPSP SEQ ID No: 100

EPKSCDKTHTSPPSP SEQ ID No: 101

EPKSCDKAAASPPCP SEQ ID No: 102

EPKSCDKAAACPPSP SEQ ID No: 103

EPKSCDKAAASPPSP SEQ ID No: 104

EPKSCDKGGGSPPCP SEQ ID No: 105

EPKSCDKGGGCPPSP SEQ ID No: 106

EPKSCDKGGGSPPSP SEQ ID No: 107

In a further aspect the invention provides an antibody of the class IgG4 comprising at least one heavy chain which comprises a $C_H1$ domain and a hinge region, wherein in each heavy chain:

the inter-chain cysteine at position 127, numbered according to the Kabat numbering system, in the $C_H1$ domain is substituted with another amino acid; and the hinge in the heavy chain or each heavy chain therein is 15 amino acids in length.

Suitable hinges are described above.

In a further aspect, the present invention also provides an antibody of the class IgG4 comprising at least one heavy chain which comprises a $C_H1$ domain and a hinge region, wherein in each heavy chain:
a. the cysteine at position 127, numbered according to the Kabat numbering system, is substituted with another amino acid; and
b. the cysteine at position 239 or the cysteine at position 242, numbered according to the Kabat numbering system, are substituted with another amino acid.

In one embodiment according to the latter aspect of the invention the IgG4 molecule also contains 22 amino acids in the hinge, for example as described above.

The antibodies provided by the present invention show advantageous properties compared to a wild-type IgG4 antibody. It has been surprisingly found that antibodies of the present invention show improved thermostability in particular of the Fab domain compared to a wild-type IgG4 antibody.

In a further aspect, the present invention also provides an antibody of the class IgG3 comprising at least one heavy chain which comprises a $C_H1$ domain and a hinge region, wherein in each heavy chain:
a. the cysteine in the $C_H1$ domain which forms an inter-chain disulphide bond with a cysteine in a light chain is substituted with another amino acid; and
b. one or more of the amino acids positioned in the upper hinge region is substituted with cysteine.

In a further aspect, the present invention provides an antibody of the class IgM comprising at least one heavy chain which comprises a $C_H1$ domain and a $C_H2$ domain, wherein in each heavy chain:
a. the cysteine in the $C_H1$ domain which forms an inter-chain disulphide bond with a cysteine in a light chain is substituted with another amino acid; and
b. one or more of the amino acids positioned in the $C_H1$ domain or $C_H2$ domain is substituted with cysteine.

In a further aspect, the present invention provides an antibody of the class IgD comprising at least one heavy chain which comprises a $C_H1$ domain and a hinge region, wherein in each heavy chain:
a. the cysteine in the $C_H1$ domain which forms an inter-chain disulphide bond with a cysteine in a light chain is substituted with another amino acid; and
b. one or more of the amino acids positioned in the hinge region is substituted with cysteine.

The present invention also provides an expression vector comprising a sequence which encodes the antibodies of the present invention and a host cell comprising the expression vector.

The present invention also provides an antibody as defined above for use in the treatment of a disease or disorder. Further provided is a method for the treatment of a disease or disorder comprising administering a therapeutically effective amount of an antibody as defined above.

In one embodiment the antibody is for use in the treatment of a disease other than cancer.

BRIEF DESCRIPTION OF THE FIGURES

FIG. 1a shows the human $C_H1$ and hinge sequences of IgG1 wild type and IgG4 wild type, wherein the hinge residues are underlined, and the kappa light chain constant sequence.

FIG. 1b shows:
the human kappa light chain constant sequence indicating the cysteine (underlined) that forms the inter-chain $C_L$-$C_H1$ disulphide bond;
the human IgG 1, 2, 3 and 4 heavy chain N-terminal $C_H1$ residues and hinge region sequences wherein the cysteine position (in upper hinge for IgG1 and in N-terminal $C_H1$ for IgG 2, 3 and 4) is indicated (underlined) which forms the inter-chain $C_L$-$C_H1$ disulphide bond;
the human IgD heavy chain N-terminal $C_H1$ residues and part of the hinge region sequences wherein the cysteine position in the N-terminal $C_H1$ sequence is indicated (underlined) which forms the inter-chain $C_L$-$C_H1$ disulphide bond;

Figure 8:
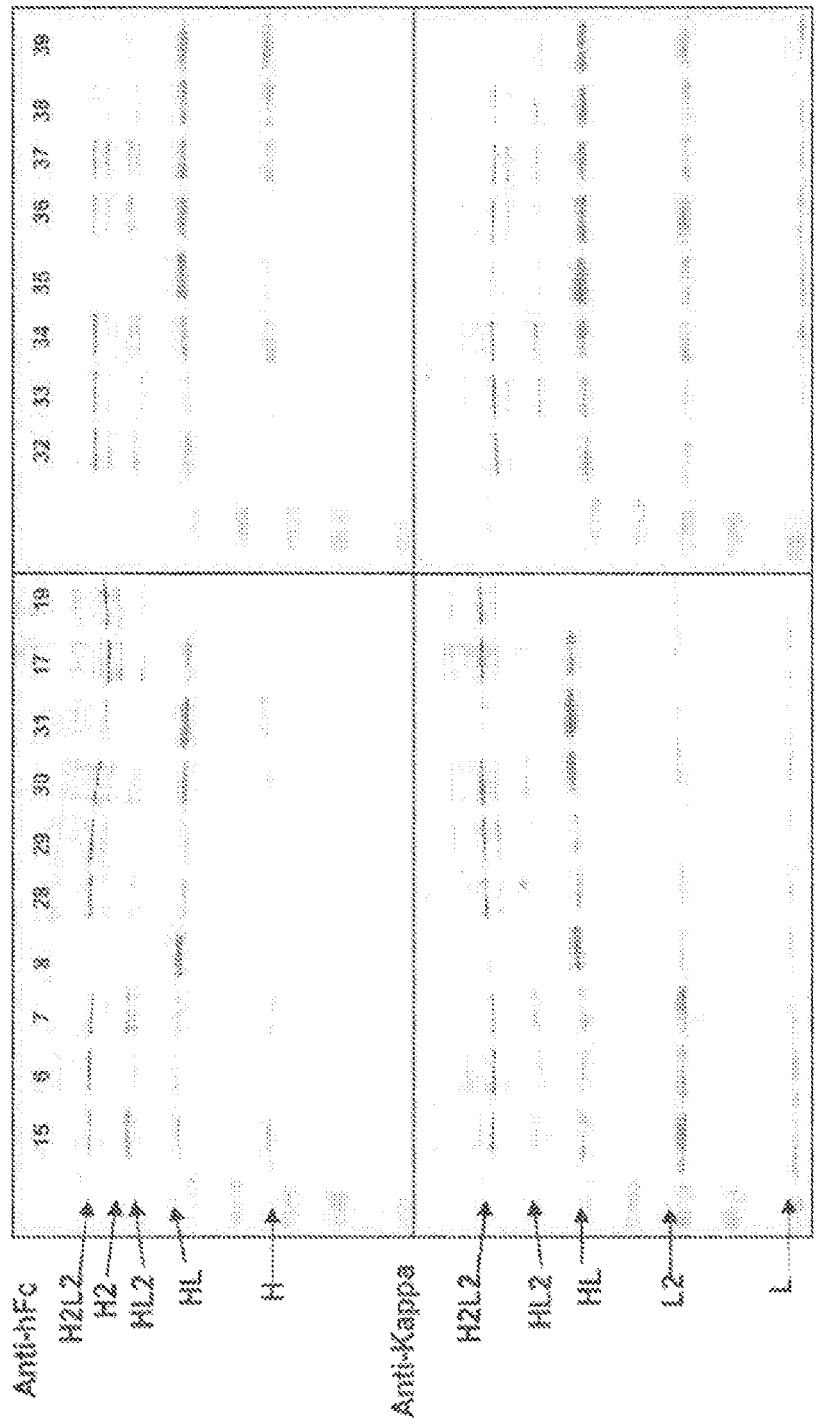

the human IgM heavy chain N-terminal $C_H1$, C-terminal $C_H1$ residues and selected N-terminal $C_H2$ residues wherein the cysteine position in the N-terminal $C_H1$ is indicated (underlined) which forms the inter-chain $C_L$-$C_H1$ disulphide bond; and the residues in the upper hinge of IgG3 and IgG4, the hinge of IgD and in the C-terminal $C_H1$ and the $C_H2$ of IgM where underlined residues indicate positions where one or more residues may be substituted with cysteine in the antibodies of the present invention.

FIG. 2a shows the $C_H1$ cysteine residue (C127) which forms the inter-chain disulphide bond with a cysteine in the light chain and the upper and core hinge residues of IgG1 wild type, IgG4 wild type and the positions where mutations have been introduced in the IgG4 antibodies of the present invention.

FIG. 2b shows the $C_H1$ cysteine residue (C127) which forms the inter-chain disulphide bond with a cysteine in the light chain and the hinge residues of IgG3 wild type and the positions where one or more residues are substituted with cysteine in the IgG3 antibodies of the present invention.

FIG. 2c shows the $C_H1$ cysteine residue (C127) which forms the inter-chain disulphide bond with a cysteine in the light chain and selected $C_H1$ and $C_H2$ residues of IgM wild type and the positions where one or more residues are substituted with cysteine in the IgM antibodies of the present invention.

FIG. 2d shows the $C_H1$ cysteine residue (C128) which forms the inter-chain disulphide bond with a cysteine in the light chain and the hinge residues of IgD wild type and the positions where one or more residues are substituted with cysteine in the IgD antibodies of the present invention.

FIG. 3a shows the mutations introduced in IgG4 antibodies according to the present invention.

FIG. 3b shows the positions of the residues in the mutated heavy chain of the IgG4 antibodies shown in FIG. 3a and the predicted disulphide bond that can form with a cysteine in either the light chain (LC) or with another mutated heavy chain (HC). Where the cysteine may bond with a cysteine in the LC or HC, the underlined chain is the predicted predominant disulphide bond arrangement.

FIG. 4a shows the mutations introduced in IgG4 antibodies according to the present invention.

FIG. 4b shows the positions of the cysteine residues in the IgG4 antibodies shown in FIG. 4a and predicted disulphide bond that can form with a cysteine in either the light chain (LC) or heavy chain (HC). Where the cysteine may bond with a cysteine in the LC or HC, the underlined chain is the predicted predominant disulphide bond arrangement.

FIG. 5 shows the sequences of the $C_H1$ and hinge region of IgG4 antibodies according to the present invention.

FIG. 6 shows the sequences of the $C_H1$, hinge region, $C_H2$ and $C_H3$ of IgG4 antibodies according to the present invention.

FIG. 7 shows the Western Blot analysis of antibodies according to the present invention with the top gel showing the results using an Anti-human Fc Antibody and the bottom gel showing the results using an Anti-Kappa Antibody.

FIG. 8 shows the Western Blot analysis of antibodies according to the present invention with the top gel showing the results using an Anti-human Fc Antibody and the bottom gel showing the results using an Anti-human Kappa Antibody.

Figure 9:
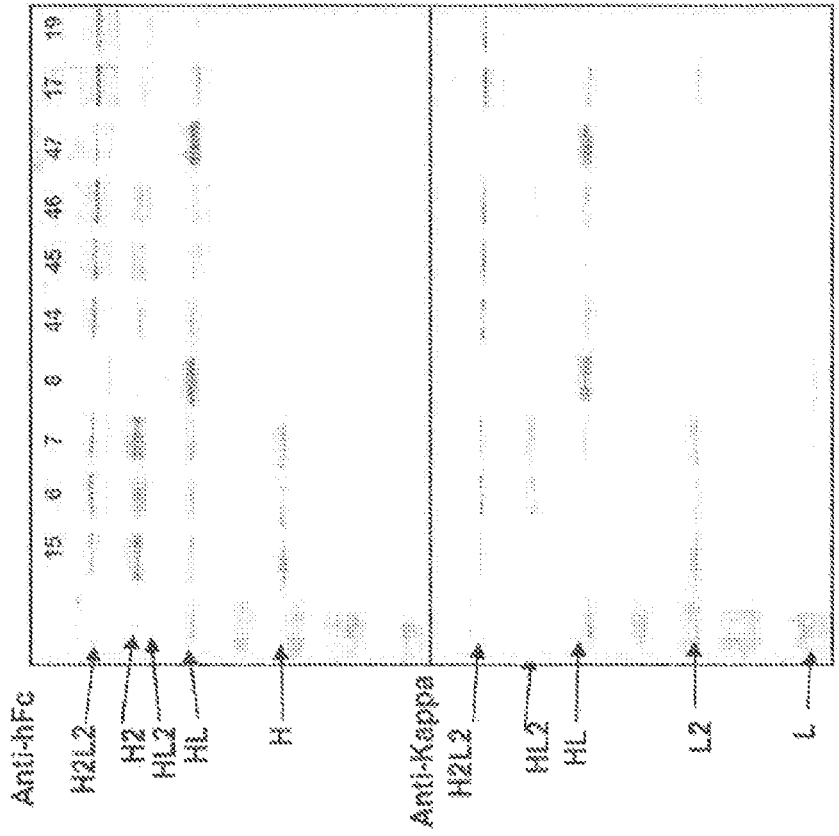

FIG. 9 shows the Western Blot analysis of antibodies according to the present invention with the top gel showing the results using an Anti-human Fc Antibody and the bottom gel showing the results using an Anti-human Kappa Antibody.

Figure 10:
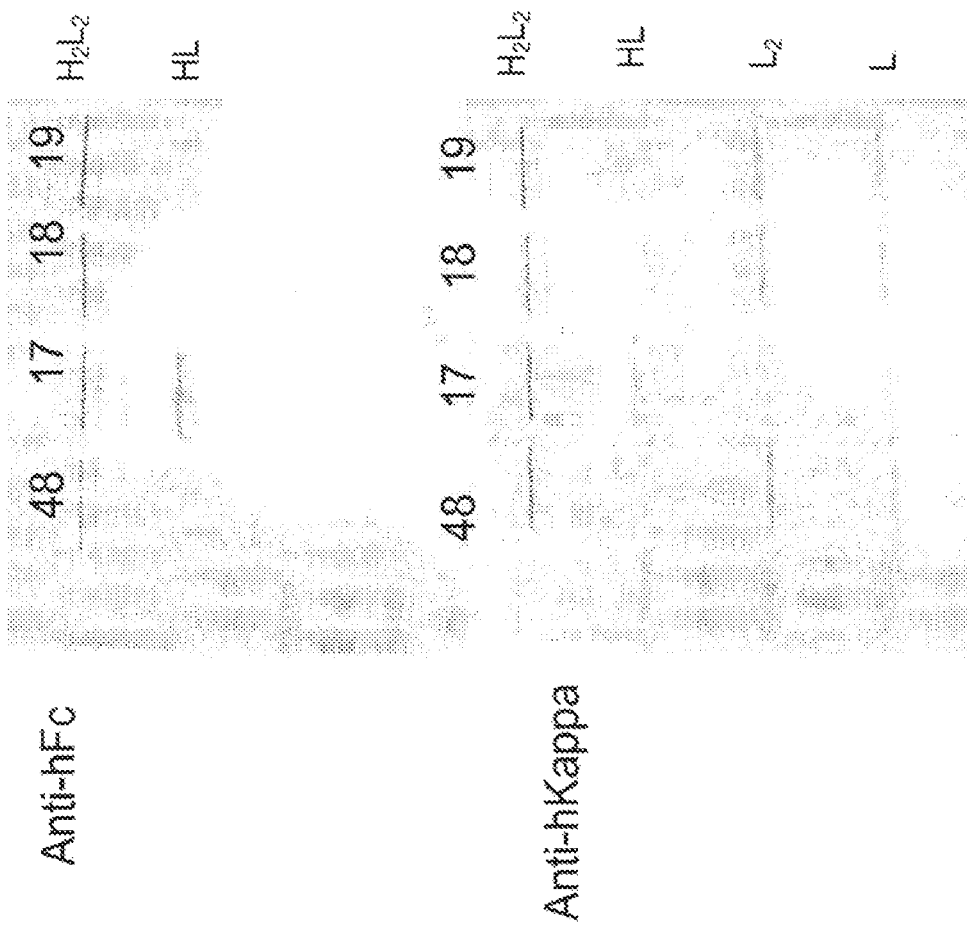

FIG. 10 shows the Western Blot analysis of an antibody according to the present invention with the top gel showing the results using an Anti-human Fc Antibody and the bottom gel showing the results using an Anti-human Kappa Antibody.

Figure 11:
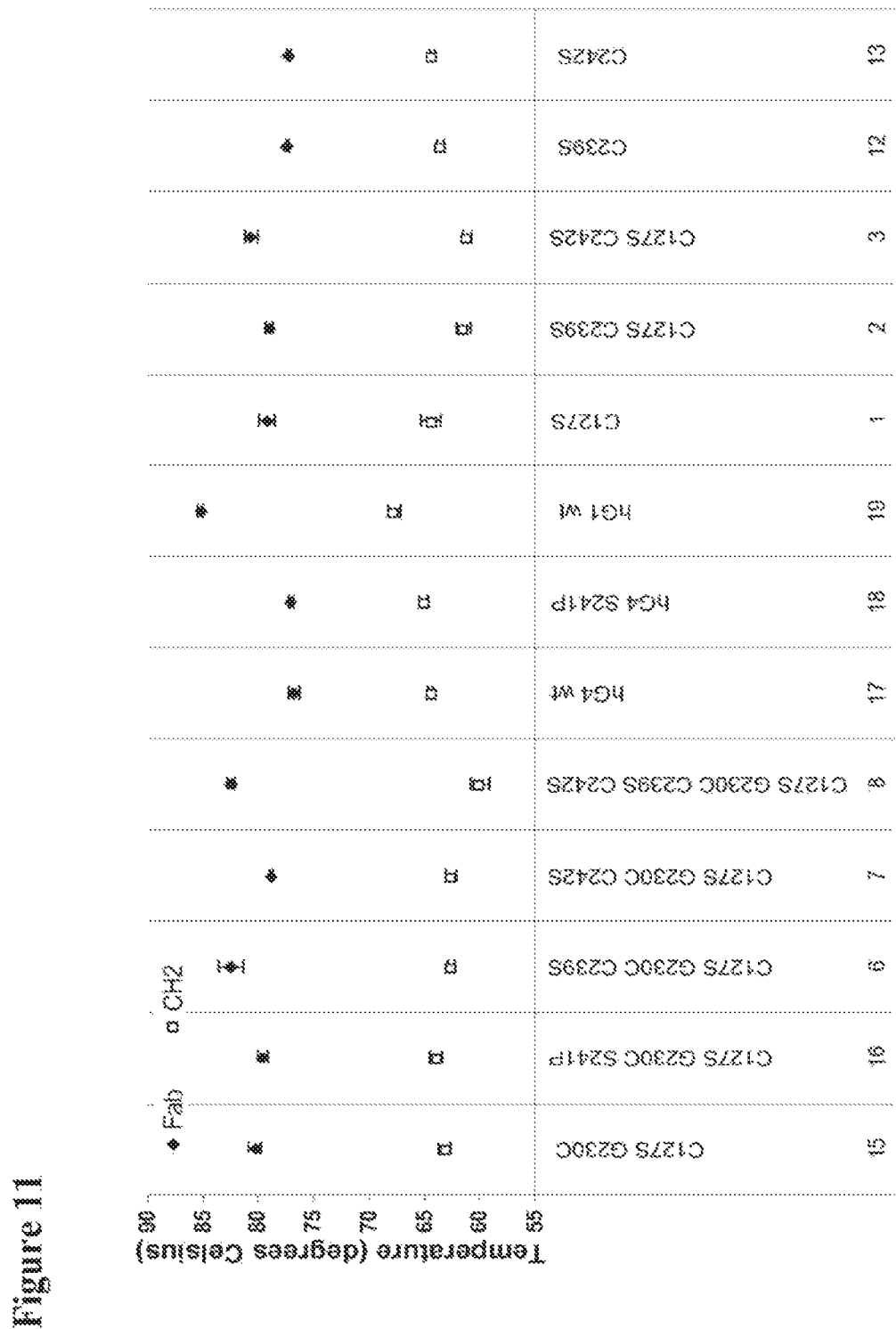

FIG. 11 shows the results of a Thermofluor analysis of antibodies of the present invention which shows the Fab and $C_H2$ domain thermostabilities.

Figure 12:
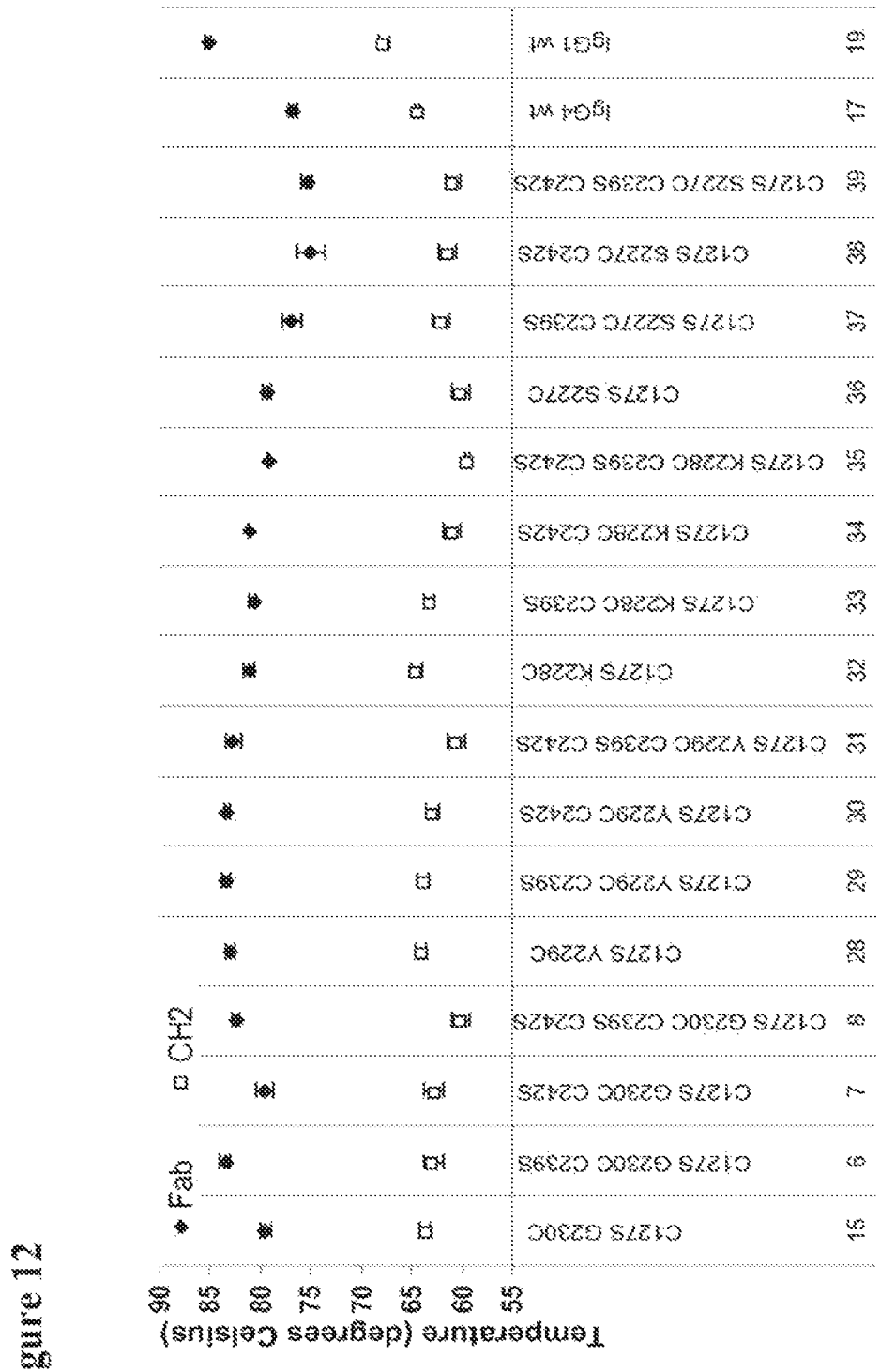

FIG. 12 shows the results of a Thermofluor analysis of antibodies of the present invention which shows the Fab and $C_H2$ domain thermostabilities.

Figure 13:

FIG. 13 shows the results of a Thermofluor analysis of antibodies of the present invention which shows the Fab and $C_H2$ domain thermostabilities.

Figure 14:
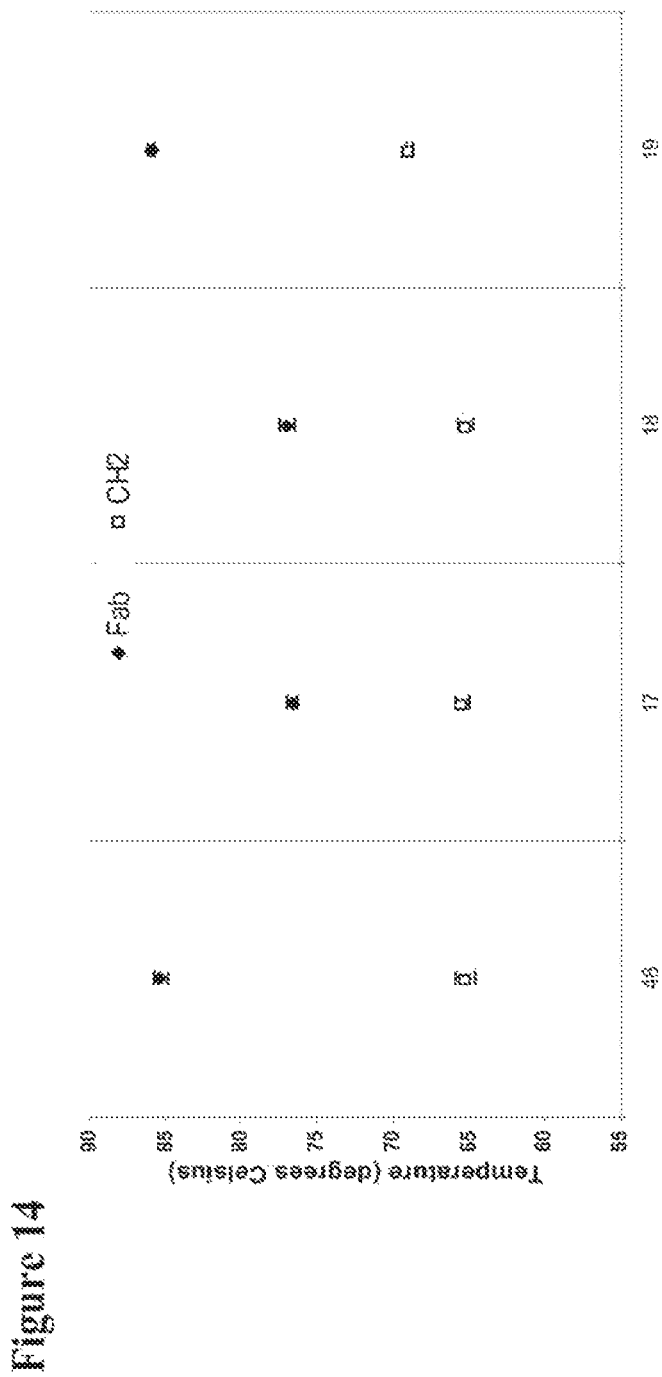

FIG. 14 shows the results of a Thermofluor analysis of antibodies of the present invention which shows the Fab and $C_H2$ domain thermostabilities.

Figure 15:
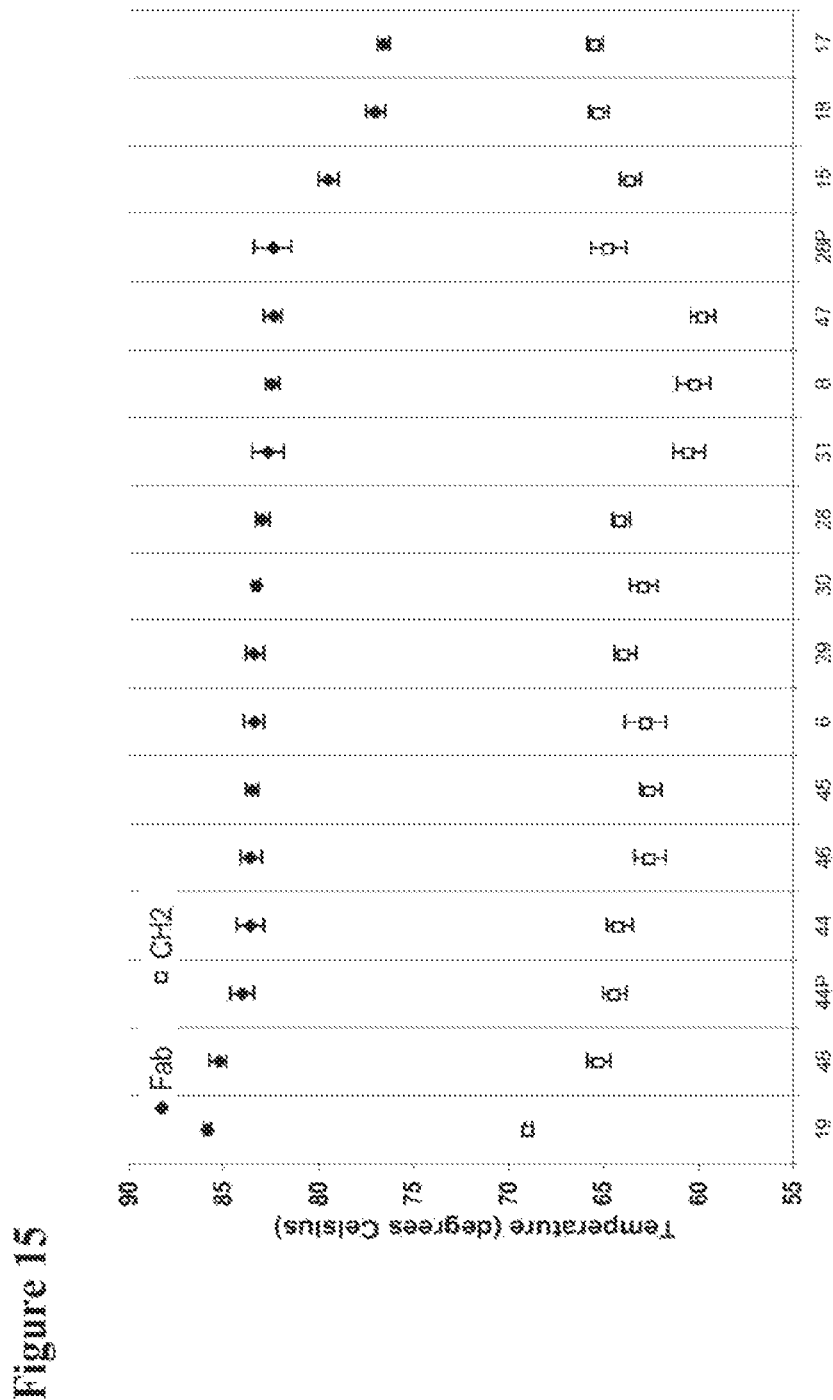

FIG. 15 shows the ranking of the thermostabilities of selected antibodies of the present invention.

FIG. 16 shows the results of an affinity assay for selected antibodies of the present invention and control antibodies.

Figure 17:
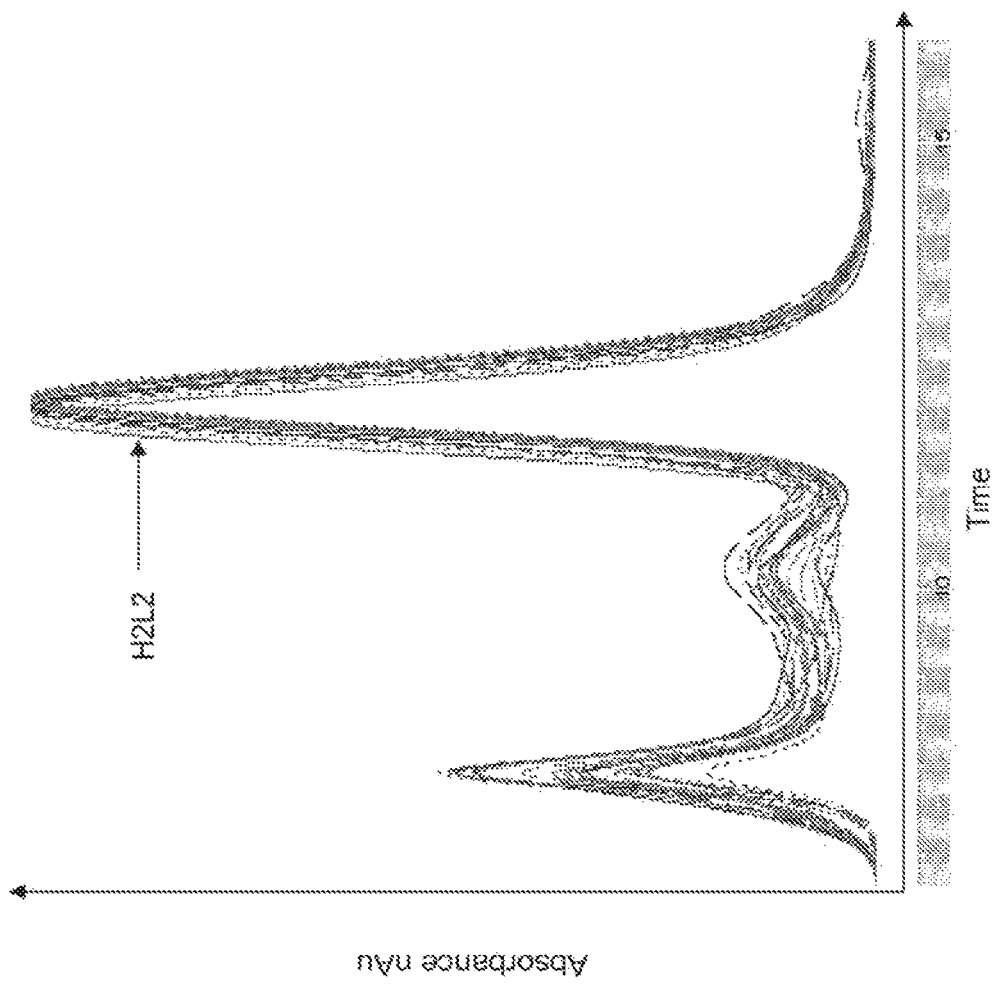

FIG. 17 shows the results of an HPLC analysis of selected antibodies of the present invention.

FIG. 18 shows a Western Blot analysis of antibodies according the present invention with different linkers.

Figure 19:
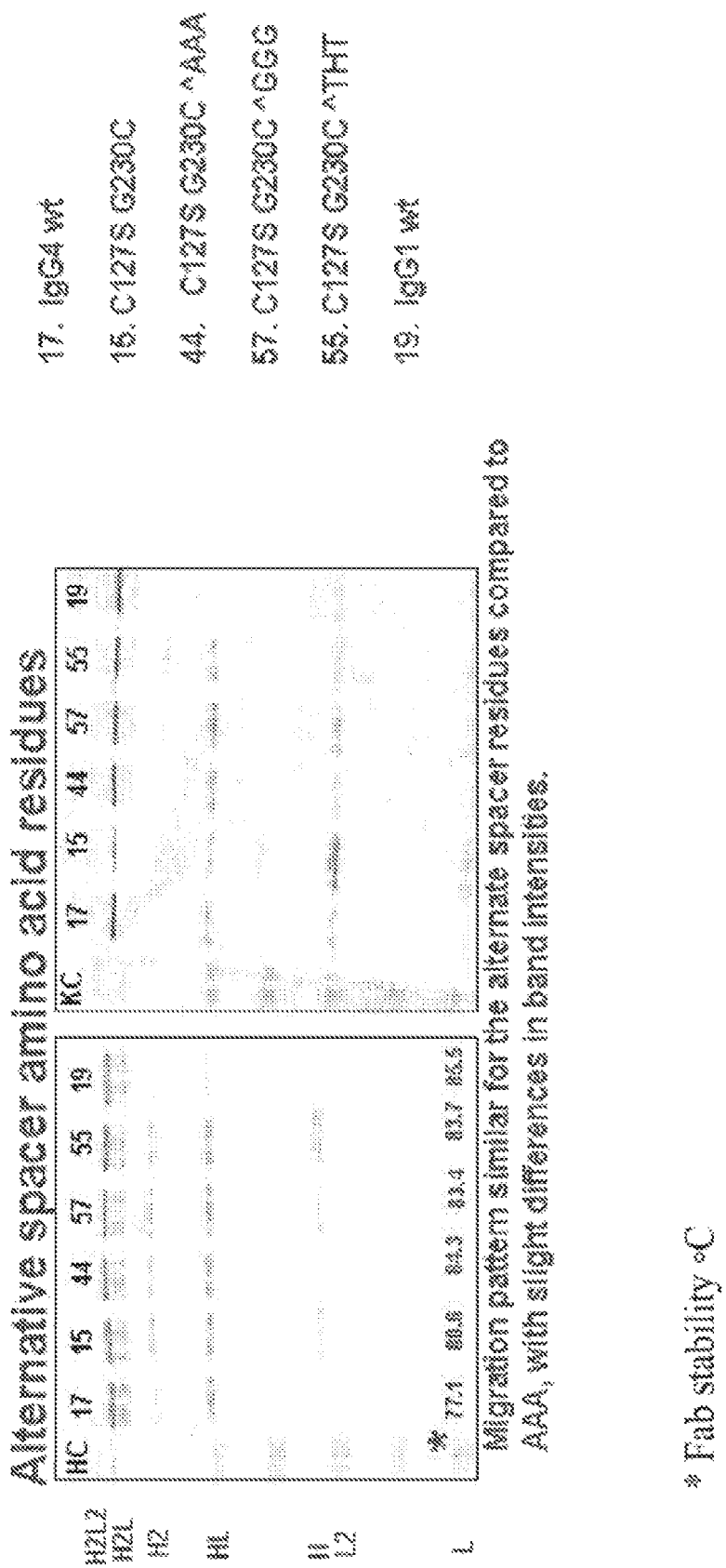
Figure 20:
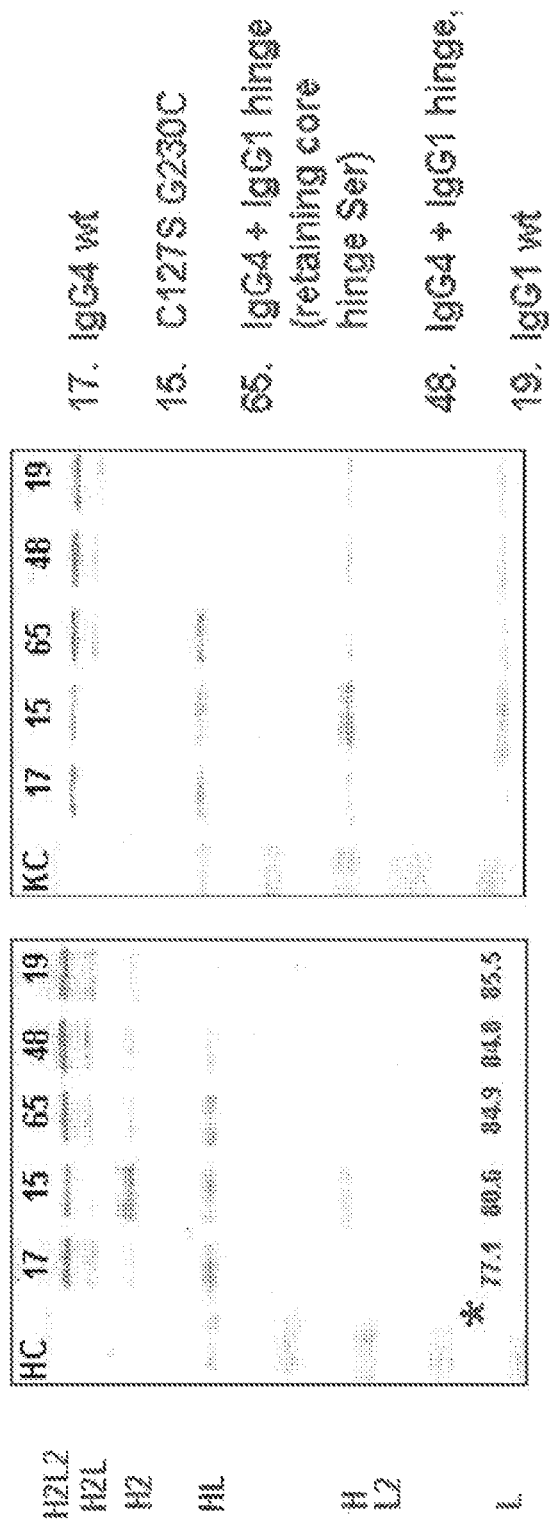

FIG. 19 shows a Western Blot analysis of antibodies according the present invention with different linkers.

FIGS. 20 to 24 show a Western Blot analysis of antibodies according the present invention with various mutations.

Figure 25:
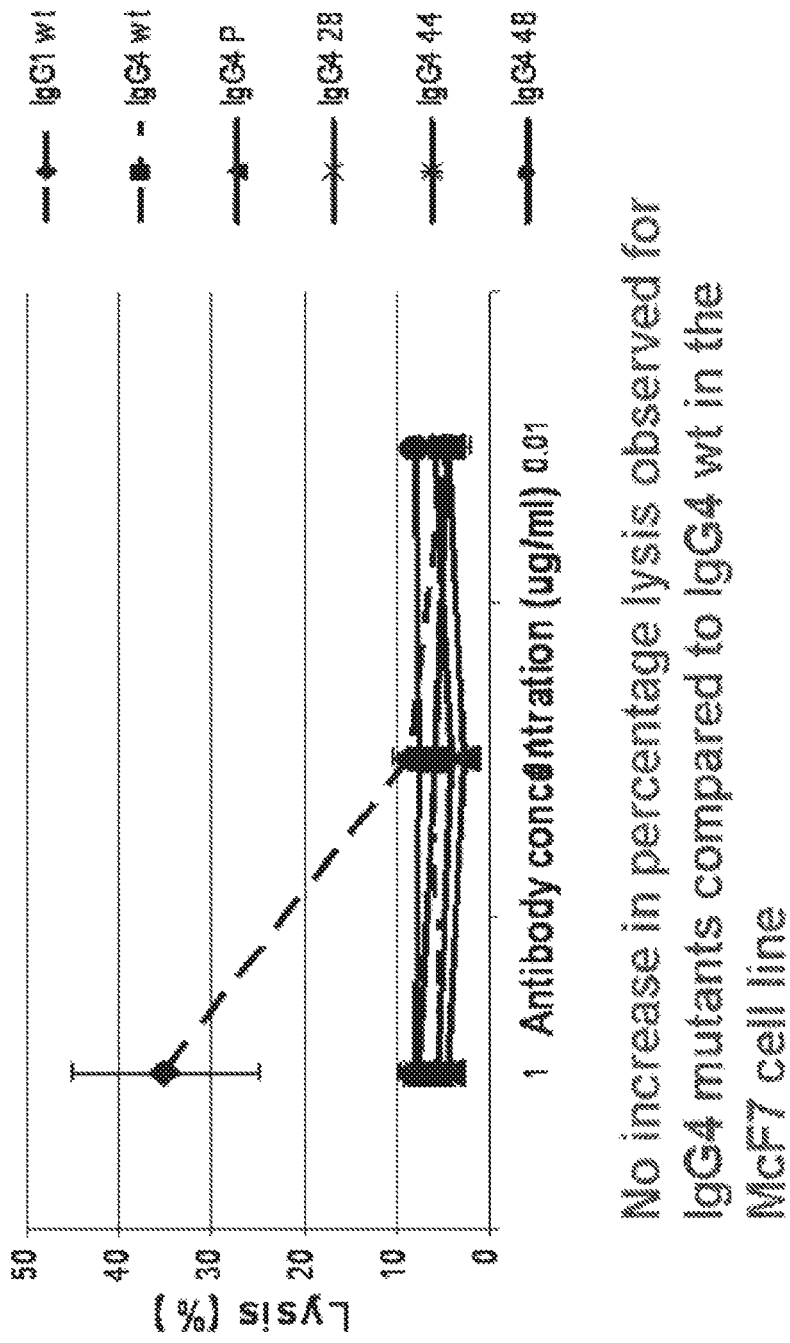
Figure 26:
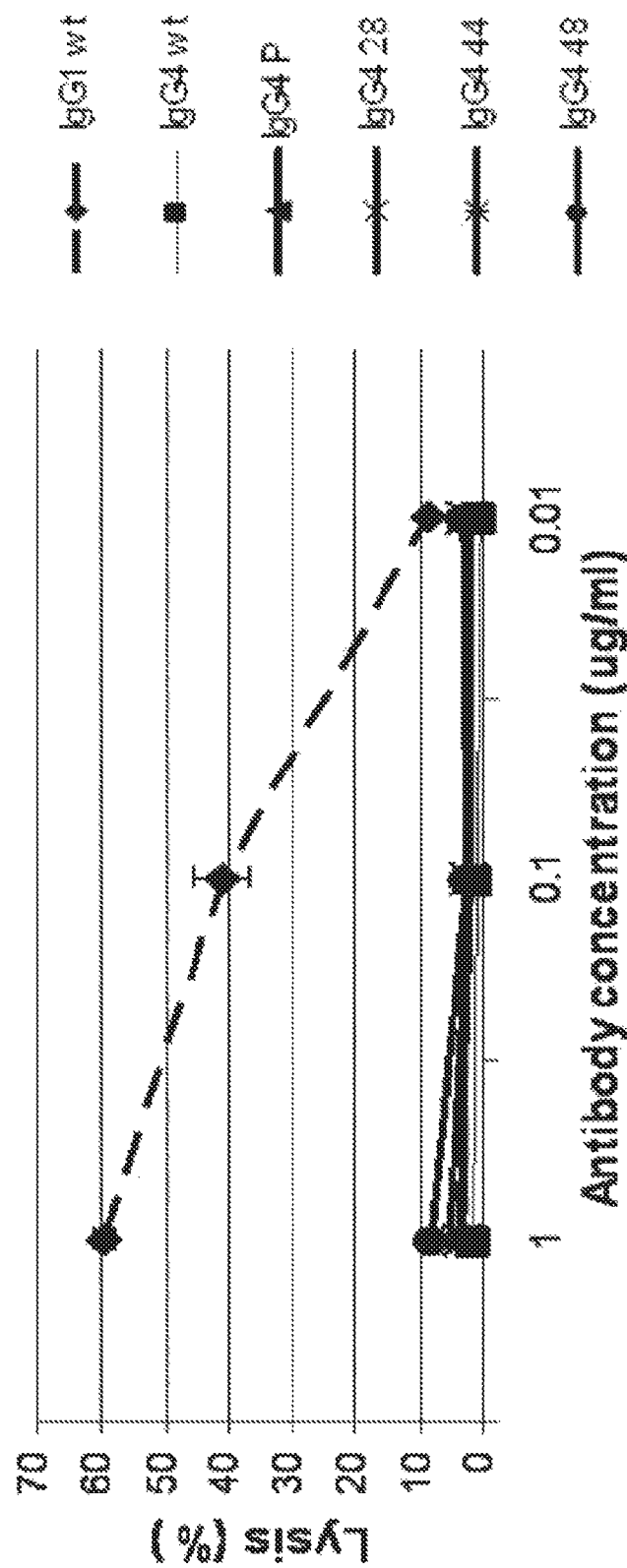

FIGS. 25 and 26 show the ADCC effector function of the various antibodies, including certain antibodies according to the invention.

Figure 27:
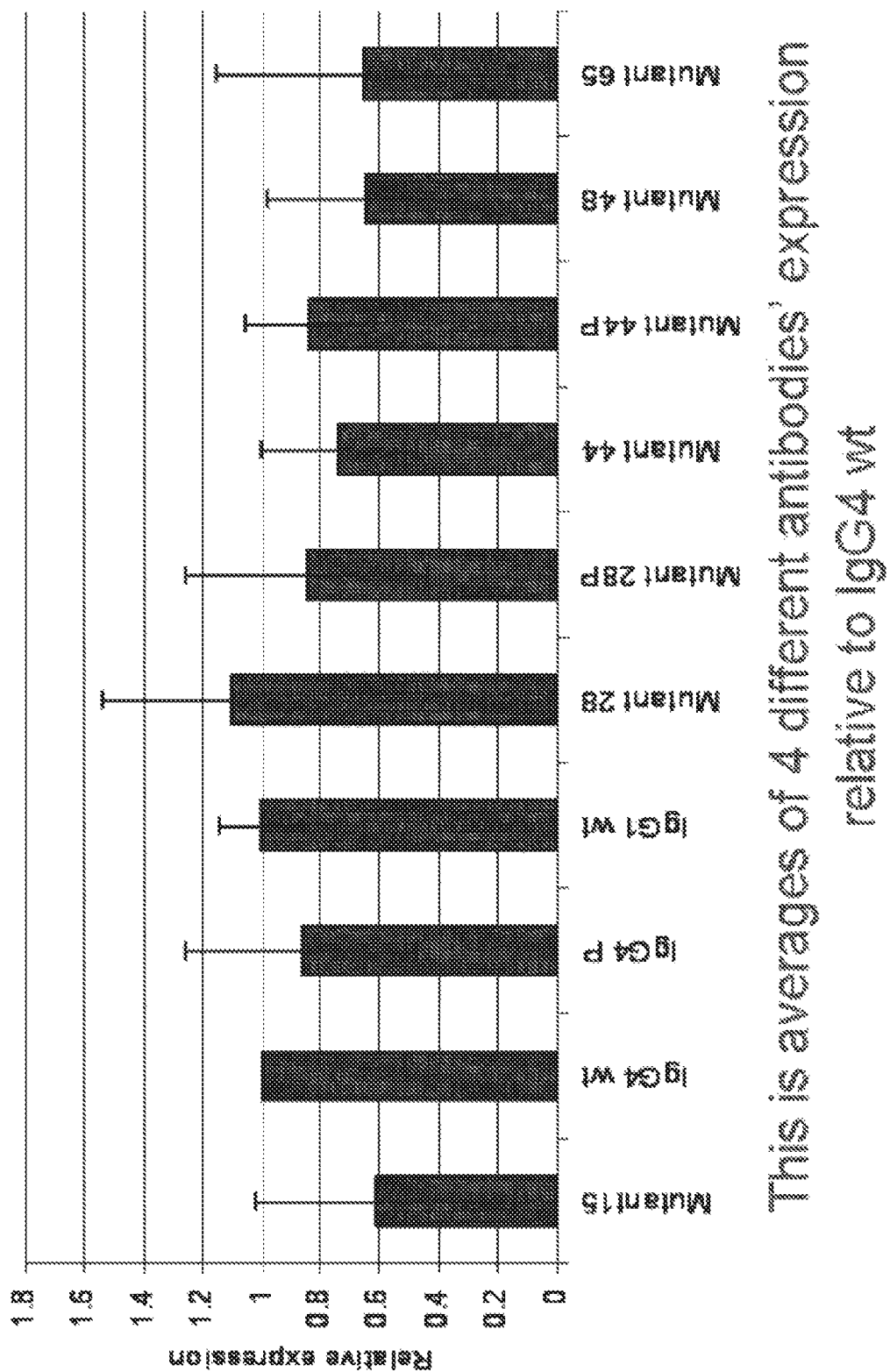

FIG. 27 shows the expression of various antibodies according to the invention.

Figure 28:
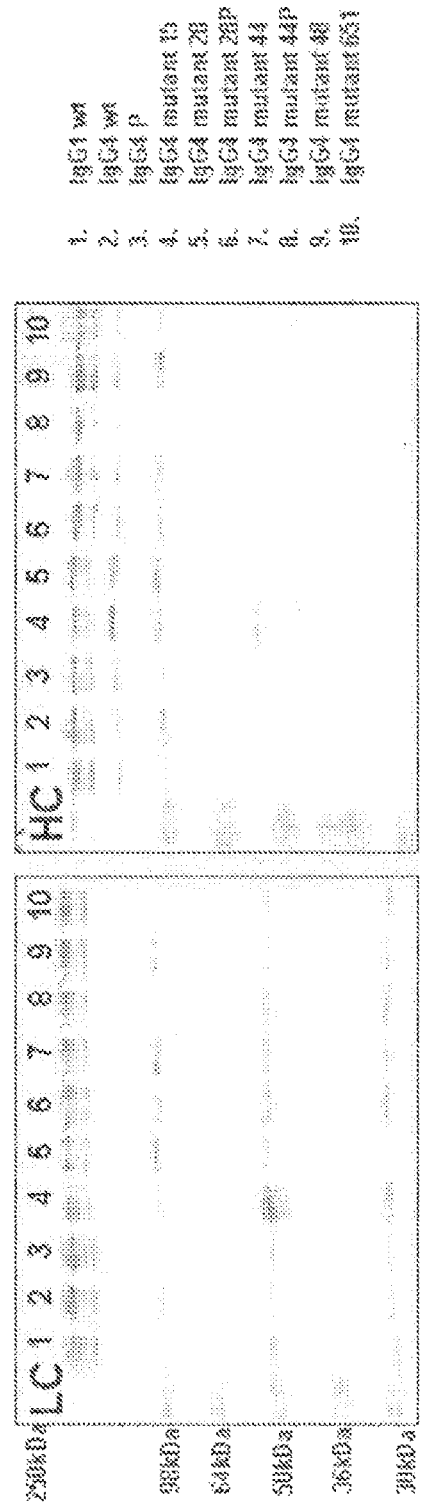

FIG. 28 shows a Western Blot of various mutations of the antibody Herceptin.

Figure 29:
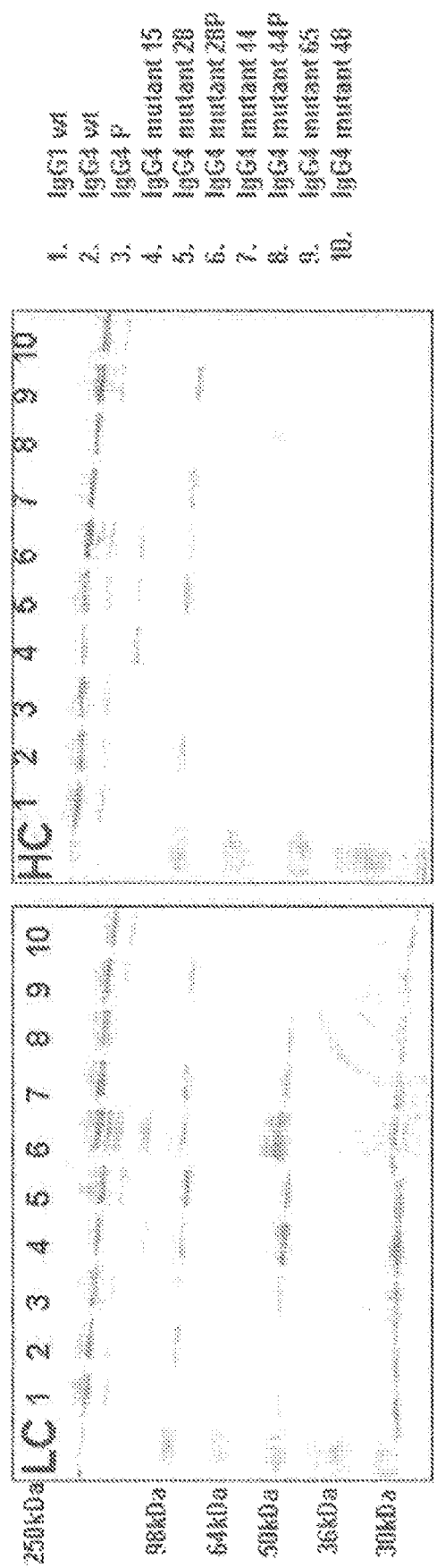

FIG. 29 shows a Western Blot of various mutations of the antibody Tysabri.

Figure 30:
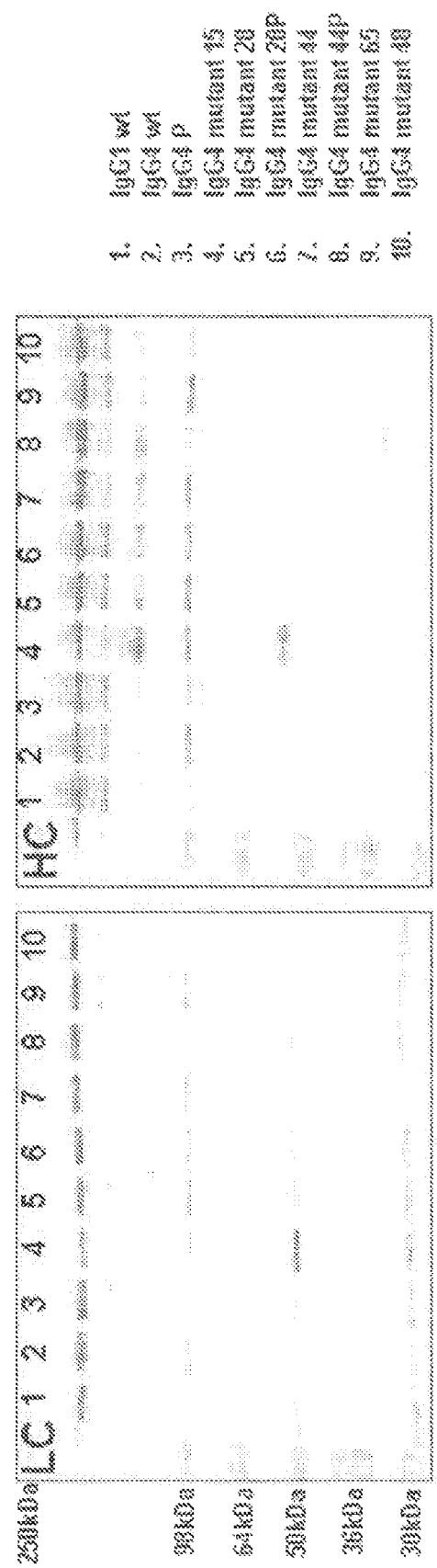

FIG. 30 shows a Western Blot of various mutations of the antibody Actemra.

FIGS. 31 to 34 show the results of a Thermofluor analysis of various antibodies according to the invention.

BRIEF DESCRIPTION OF THE SEQUENCES

SEQ ID NO: 1 shows the CH1 and hinge region sequence of an IgG1 wild-type antibody.

SEQ ID NO: 2 shows the CH1 and hinge region sequence of an IgG4 wild-type antibody.

SEQ ID NO: 3 shows a part of the constant region of a human wild-type kappa light chain.

SEQ ID NO: 4 shows a part of the N-terminal sequence of the CH1 domain of a human IgG1 antibody.

SEQ ID NO: 5 shows the hinge region of a human IgG1 antibody.

SEQ ID NO: 6 shows a part of the N-terminal sequence of the CH1 domain of a human IgG2 antibody.

SEQ ID NO: 7 shows the hinge region of a human IgG2 antibody.

SEQ ID NO: 8 shows a part of the N-terminal sequence of the CH1 domain of a human IgG3 antibody.

SEQ ID NO: 9 shows the hinge region of a human IgG3 antibody.

SEQ ID NO: 10 shows a part of the N-terminal sequence of the CH1 domain of a human IgG4 antibody.

SEQ ID NO: 11 shows the hinge region of a human IgG4 antibody.

SEQ ID NOs: 12 to 37 show the CH1 domain and hinge region sequences of antibodies 6, 7, 8, 15, 16, 28, 29, 30, 31, 32, 33, 34, 35, 36, 37, 38, 39, 44, 45, 46, 47, 2, 3, 48, 28P and 44P respectively.

SEQ ID NOs: 38 to 63 show the CH1 domain, hinge region, CH2 domain and CH3 domain sequences of antibodies 6, 7, 8, 15, 16, 28, 29, 30, 31, 32, 33, 34, 35, 36, 37, 38, 39, 44, 45, 46, 47, 2, 3, 48, 28P and 44P respectively.

SEQ ID NO: 64 show the wild type IgG4 CH2 and CH3 domain sequences.

SEQ ID NO: 65 shows the wild type IgG4 CH2 and wild type IgG1 CH3 domain sequences.

SEQ ID NO: 66 shows the constant region sequence of a human wild-type kappa light chain.

SEQ ID NO: 67 shows a part of the N-terminal sequence of the CH1 domain of a human IgGD antibody.

SEQ ID NO: 68 shows a part of the hinge region of a human IgGD antibody.

SEQ ID NO: 69 shows a part of the N-terminal sequence of the CH1 domain of a human IgGM antibody.

SEQ ID NO: 70 shows a part of the C-terminal sequence of the CH1 domain of a human IgGM antibody.

SEQ ID NO: 71 shows a part of the CH2 domain of a human IgGM antibody.

SEQ ID NO: 72 to 295 shows various hinge regions.

DETAILED DESCRIPTION OF THE PREFERRED EMBODIMENTS OF THE INVENTION

The present invention will now be described in more detail.

The terms "protein" and "polypeptide" are used interchangeably herein, unless the context indicates otherwise. "Peptide" is intended to refer to 10 or less amino acids.

The terms "polynucleotide" includes a gene, DNA, cDNA, RNA, mRNA etc unless the context indicates otherwise.

As used herein, the term "comprising" in context of the present specification should be interpreted as "including".

The term "wild-type" in the context of the present invention means an antibody as it may occur in nature or may be isolated from the environment, which does not comprise any genetically engineered mutations.

The designation for a substitution mutant herein consists of a letter followed by a number followed by a letter. The first letter designates the amino acid in the wild-type protein. The number refers to the amino acid position where the amino acid substitution is being made, and the second letter designates the amino acid that is used to replace the wild-type amino acid.

The residues in antibody variable and constant domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)").

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

Alternatively, the numbering of amino acid residues may be performed by the EU-index or EU numbering system (also described in Kabat et al., Sequences of Proteins of Immunological Interest, 5th Ed. Public Health Service, National Institutes of Health, Bethesda, Md. (1991)).

A further numbering system of amino acid residues in antibodies is the IMGT numbering system (Lefranc, M.-P. et al., Dev. Comp. Immunol., 29, 185-203 (2005)).

The Kabat numbering system is used in the present specification except where otherwise indicated that the EU numbering system or IMGT numbering system is used.

Between the four IgG4 isotypes, the intrachain disulphide bonding arrangements in the heavy and light chain are similar whereas the interchain disulphide bonding arrangements are unique for each isotype [Reviewed by (Wypych, J., Li, M., Guo, A., Zhang, Z., Martinez, T., Allen, M. J., Fodor, S., Kelner, D. N., Flynn, G. C., Liu, Y. D., Bondarenko, P. V., Ricci, M. S., Dillon, T. M., Balland, A., 2008. Human IgG2 antibodies display disulphide-mediated structural isoforms. J Biol. Chem. 283, 16194-16205)].

As shown in FIG. 1b, the hinge region sequences of the four IgG4 isotypes differ. The complete or genetic hinge region typically consists of residues 226 to 251 (numbering based on Kabat numbering system). FIG. 1b shows the upper, core and lower sections of the hinge regions of the four IgG4 isotypes. For the IgG1 isotype, the upper hinge region is residues 226 to 238, the core hinge region is residues 239 to 243 and the lower hinge region is residues 244 to 251. For the IgG4 isotype, the upper hinge region is residues 226 to 238, the core hinge region is residues 239 to 243 and the lower hinge region is residues 244 to 251.

Thus the hinge comprising the upper hinge, core and lower hinge in an IgG1 is 23 amino acids in length as shown in FIG. 1a. The upper hinge is 10 amino acids. The core is 5 amino acids and the lower hinge is 8, see for example FIG. 1b.

The hinge comprising the upper hinge, core and lower hinge in an IgG4 is 20 amino acids in length as shown in FIG. 1a. The upper hinge is 7 amino acids. The core is 5 amino acids and the lower hinge is 8, see for example FIG. 1b.

The new mutant IgG4 antibodies according to the present invention have been developed by modifying the interchain disulphide bond arrangements within IgG4, specifically the $C_L$-$C_{H1}$ interchain disulphide bond arrangement between the light chain (LC) and heavy chain (HC) has been modified.

FIG. 1b shows sections of the human IgG heavy and light chain sequences for the IgG 1-4 isotypes indicating the cysteine positions (underlined) that form the $C_L$-$C_H$1 interchain disulphide bonds. The inter $C_L$-$C_H$1 disulphide bond of IgG1 is formed between the LC C214 (Kabat numbering system) and C233 (Kabat numbering system) of the HC just before the hinge region. In contrast, the $C_H$1-$C_L$ disulphide bond for IgG2, 3 and 4 is formed between the LC C214 and C127 N-terminal to the intrachain disulphide bond of the HC. The LC and HC sequences surrounding the cysteine residues involved in the $C_L$-$C_H$1 disulphide bond formation are shown and aligned in FIG. 1b.

The present invention has investigated how the $C_L$-$C_H$1 disulphide bond affects the properties of an IgG4 antibody including the thermostability, structural stability, disulphide isoform heterogeneity and affinity of the antibody.

Mutants of IgG4 were generated by substitution of the cysteine residue in $C_{H1}$ at position 127 with another amino acid as well as substituting one or more of the amino acids in the upper hinge region, preferably amino acids at positions selected from 227, 228, 229 and 230, numbered according to the Kabat numbering system of IgG4, with cysteine. Positions 227, 228, 229 or 230 are at or near to the equivalent structural position that the IgG1 cysteine 233 is situated.

Each heavy chain may comprise further mutations including the substitution of one or both cysteine residues 239 and 242 in the IgG4 hinge region with another amino acid. A mutation to lengthen the IgG4 upper hinge region by three amino acids between positions 238 and 239 to be the same length as the IgG1 hinge was also included in some antibodies. The S241P mutation was also introduced in some antibodies.

It has been found that the mutant IgG4 antibodies according to the present invention show advantageous properties.

In one embodiment, the mutant IgG4 antibodies according to the present invention show increased thermostability compared to a wild-type IgG4 antibody. It has been surprisingly found that the mutant IgG4 antibodies which have been mutated to replace the cysteine at position 127 in the $C_H1$ domain with another amino acid and in which a cysteine has been introduced in the heavy chain hinge region between positions 227 to 230 show improved thermostability compared to a wild type IgG4 antibody. The mutation to remove cysteine at position 127 alters the position at which the inter-chain disulphide bond forms between the heavy chain and the light chain ($C_L$-$C_{H1}$) and forces the light chain to form a disulphide bond with a cysteine which is introduced between positions 227 and 230 in the hinge region of the heavy chain. Hence in one embodiment, an IgG4 antibody is provided in which the cysteine 127 is substituted for another amino acid and the cysteine of the light chain is linked via a disulphide bond to an engineered cysteine at position 227, 228, 229 or 230.

A further improvement to thermostability was also surprisingly found by adding three amino acids to the IgG4 hinge region in order to lengthen the IgG4 hinge region.

It has also been surprisingly found that the mutant IgG4 antibodies which have been mutated to replace the cysteine at position 127 in the $C_H1$ domain with another amino acid and to replace the cysteine at position 239 or at position 242 in the heavy chain hinge region with another amino acid showed improved thermostability compared to a wild type IgG4 antibody.

In one embodiment the antibodies of the present invention show reduced formation of so-called half-molecules. Antibodies of the present invention which comprise a mutation at C239 but do not carry a mutation at C242 generally show reduced half-molecule formation. Without being bound by theory it is thought that this is due to removal of the Cysteine at position 239 reduces the formation of intra-chain disulphide bond in the heavy chain and therefore reduces the number of half-molecules compared to antibodies which do not carry a mutation at C239 or the C242. Antibodies which carry a mutation at C242 but do not carry a mutation at C239 appear to form more half-molecule compared to antibodies which carry a mutation at C239 but do not carry a mutation at C242. Without being bound by theory, it is believed that the cysteine at position 239 is more reactive compared to the cysteine at position 242 and is capable of forming a disulphide bond with either a heavy chain hinge cysteine or the light chain cysteine.

Antibodies which carry mutation at both C239 and C242 form a high proportion of half-molecules due to no interchain disulphide bond formation between two heavy chains. However, antibodies comprising mutations at both C239 and C242 are still capable of forming whole antibody molecules due to the bonding of heavy chains via non-covalent bonds.

Reduced half-molecule formation is also observed in antibodies carrying the S241P mutation.

In one embodiment the upper hinge and core region is selected from one of the following sequences:

| | |
|---|---|
| ESKYGPPCPSCP | SEQ ID No: 108 |
| ESKYGDKCPSCP | SEQ ID No: 109 |
| EPSKYGPPCPSCP | SEQ ID No: 110 |
| EPSKYGDKCPSCP | SEQ ID No: 111 |
| ESKSYGPPCPSCP | SEQ ID No: 112 |
| ESKSYGDKCPSCP | SEQ ID No: 113 |
| ESKYGPPAACPSCP | SEQ ID No: 114 |
| ESKYGPPGGCPSCP | SEQ ID No: 115 |
| ESKYGPPHTCPSCP | SEQ ID No: 116 |
| ESKYGDKHTCPSCP | SEQ ID No: 117 |
| EPSKYGPPAACPSCP | SEQ ID No: 118 |
| EPSKYGPPGGCPSCP | SEQ ID No: 119 |
| EPSKYGPPHTCPSCP | SEQ ID No: 120 |
| EPSKYGDKHTCPSCP | SEQ ID No: 121 |
| ESKSYGPPAACPSCP | SEQ ID No: 122 |
| ESKSYGPPGGCPSCP | SEQ ID No: 123 |
| ESKSYGPPHTCPSCP | SEQ ID No: 124 |
| ESKSYGDKHTCPSCP | SEQ ID No: 125 |
| ESKYGPPACPSCP | SEQ ID No: 126 |
| ESKYGPPGCPSCP | SEQ ID No: 127 |
| ESKYGPPTTCPSCP | SEQ ID No: 128 |
| ESKYGDKTTCPSCP | SEQ ID No: 129 |

-continued

EPSKYGPPACPSCP SEQ ID No: 130

EPSKYGPPGCPSCP SEQ ID No: 131

EPSKYGPPTTCPSCP SEQ ID No: 132

EPSKYGDKTTCPSCP SEQ ID No: 133

ESKSYGPPACPSCP SEQ ID No: 134

ESKSYGPPGCPSCP SEQ ID No: 135

ESKSYGPPTTCPSCP SEQ ID No: 136

ESKSYGDKTTCPSCP SEQ ID No: 137

ESKYGPPTHCPSCP SEQ ID No: 138

ESKYGDKTHCPSCP SEQ ID No: 139

EPSKYGPPTHCPSCP SEQ ID No: 140

EPSKYGDKTHCPSCP SEQ ID No: 141

ESKSYGPPTHCPSCP SEQ ID No: 142

ESKSYGDKTHCPSCP SEQ ID No: 143

ESKYGPPHTCPSCP SEQ ID No: 144

ESKYGDKHTCPSCP SEQ ID No: 145

EPSKYGPPHTCPSCP SEQ ID No: 146

EPSKYGDKHTCPSCP SEQ ID No: 147

ESKSYGPPHTCPSCP SEQ ID No: 148

ESKSYGDKHTCPSCP SEQ ID No: 149

ESKYGPPTCPSCP SEQ ID No: 150

ESKYGDKTCPSCP SEQ ID No: 151

EPSKYGPPTCPSCP SEQ ID No: 152

EPSKYGDKTCPSCP SEQ ID No: 153

ESKSYGPPTCPSCP SEQ ID No: 154

ESKSYGDKTCPSCP SEQ ID No: 155

ESKYGPPHCPSCP SEQ ID No: 156

-continued

ESKYGDKHCPSCP SEQ ID No: 157

EPSKYGPPHCPSCP SEQ ID No: 158

EPSKYGDKHCPSCP SEQ ID No: 159

ESKSYGPPHCPSCP SEQ ID No: 160

ESKSYGDKHCPSCP SEQ ID No: 161

EPKSCDKAACPPCP SEQ ID No: 162

EPKSCDKGGCPPCP SEQ ID No: 163

EPKSCDKHTSPPCP SEQ ID No: 164

EPKSCDKHTCPPSP SEQ ID No: 165

EPKSCDKHTSPPSP SEQ ID No: 166

EPKSCDKAASPPCP SEQ ID No: 167

EPKSCDKAACPPSP SEQ ID No: 168

EPKSCDKAASPPSP SEQ ID No: 169

EPKSCDKGGSPPCP SEQ ID No: 170

EPKSCDKGGCPPSP SEQ ID No: 171

EPKSCDKGGSPPSP SEQ ID No: 172

EPKSCDKACPPCP SEQ ID No: 173

EPKSCDKGCPPCP SEQ ID No: 174

EPKSCDKTSPPCP SEQ ID No: 175

EPKSCDKTCPPSP SEQ ID No: 176

EPKSCDKTSPPSP SEQ ID No: 177

EPKSCDKASPPCP SEQ ID No: 178

EPKSCDKACPPSP SEQ ID No: 179

EPKSCDKASPPSP SEQ ID No: 180

EPKSCDKGSPPCP SEQ ID No: 181

EPKSCDKGCPPSP SEQ ID No: 182

EPKSCDKGSPPSP SEQ ID No: 183

EPKSCDKCPPCP SEQ ID No: 184

EPKSCDKCPPCP SEQ ID No: 185

EPKSCDKSPPCP SEQ ID No: 186

EPKSCDKCPPSP SEQ ID No: 187

EPKSCDKSPPSP SEQ ID No: 188

EPKSCDKSPPCP SEQ ID No: 189

EPKSCDKCPPSP SEQ ID No: 190

EPKSCDKSPPSP SEQ ID No: 191

EPKSCDKSPPCP SEQ ID No: 192

EPKSCDKCPPSP SEQ ID No: 193

EPKSCDKSPPSP SEQ ID No: 194

EPKSCDKTTSPPCP SEQ ID No: 195

EPKSCDKTTCPPSP SEQ ID No: 196

EPKSCDKTTSPPSP SEQ ID No: 197

EPKSCDKTHSPPCP SEQ ID No: 198

EPKSCDKTHCPPSP SEQ ID No: 199

EPKSCDKTHSPPSP SEQ ID No: 200

ESKYGPPCPPCP SEQ ID No: 201

ESKYGPPCPPCP SEQ ID No: 202

ESKYGPPCPPCP SEQ ID No: 203

ESKYGDKCPPCP SEQ ID No: 204

EPSKYGPPCPPCP SEQ ID No: 205

EPSKYGPPCPPCP SEQ ID No: 206

EPSKYGPPCPPCP SEQ ID No: 207

EPSKYGDKCPPCP SEQ ID No: 208

ESKSYGPPCPPCP SEQ ID No: 209

ESKSYGPPCPPCP SEQ ID No: 210

ESKSYGPPCPPCP SEQ ID No: 211

ESKSYGDKCPPCP SEQ ID No: 212

ESKYGPPAACPPCP SEQ ID No: 213

ESKYGPPGGCPPCP SEQ ID No: 214

ESKYGPPHTCPPCP SEQ ID No: 215

ESKYGDKHTCPPCP SEQ ID No: 216

EPSKYGPPAACPPCP SEQ ID No: 217

EPSKYGPPGGCPPCP SEQ ID No: 218

EPSKYGPPHTCPPCP SEQ ID No: 219

EPSKYGDKHTCPPCP SEQ ID No: 220

ESKSYGPPAACPPCP SEQ ID No: 221

ESKSYGPPGGCPPCP SEQ ID No: 222

ESKSYGPPHTCPPCP SEQ ID No: 223

ESKSYGDKHTCPPCP SEQ ID No: 224

ESKYGPPACPPCP SEQ ID No: 225

ESKYGPPGCPPCP SEQ ID No: 226

ESKYGPPTTCPPCP SEQ ID No: 227

ESKYGDKTTCPPCP SEQ ID No: 228

EPSKYGPPACPPCP SEQ ID No: 229

EPSKYGPPGCPPCP SEQ ID No: 230

EPSKYGPPTTCPPCP SEQ ID No: 231

EPSKYGDKTTCPPCP SEQ ID No: 232

ESKSYGPPACPPCP SEQ ID No: 233

ESKSYGPPGCPPCP SEQ ID No: 234

ESKSYGPPTTCPPCP SEQ ID No: 235

ESKSYGDKTTCPPCP SEQ ID No: 236

ESKYGPPTHCPPCP SEQ ID No: 237

| | |
|---|---|
| ESKYGDKTHCPPCP | SEQ ID No: 238 |
| EPSKYGPPTHCPPCP | SEQ ID No: 239 |
| EPSKYGDKTHCPPCP | SEQ ID No: 240 |
| ESKSYGPPTHCPPCP | SEQ ID No: 241 |
| ESKSYGDKTHCPPCP | SEQ ID No: 242 |
| ESKYGPPHTCPPCP | SEQ ID No: 243 |
| ESKYGDKHTCPPCP | SEQ ID No: 244 |
| EPSKYGPPHTCPPCP | SEQ ID No: 245 |
| EPSKYGDKHTCPPCP | SEQ ID No: 246 |
| ESKSYGPPHTCPPCP | SEQ ID No: 247 |
| ESKSYGDKHTCPPCP | SEQ ID No: 248 |
| ESKYGPPTCPPCP | SEQ ID No: 249 |
| ESKYGDKTCPPCP | SEQ ID No: 250 |
| EPSKYGPPTCPPCP | SEQ ID No: 251 |
| EPSKYGDKTCPPCP | SEQ ID No: 252 |
| ESKSYGPPTCPPCP | SEQ ID No: 253 |
| ESKSYGDKTCPPCP | SEQ ID No: 254 |
| ESKYGPPHCPPCP | SEQ ID No: 255 |
| ESKYGDKHCPPCP | SEQ ID No: 256 |
| EPSKYGPPHCPPCP | SEQ ID No: 257 |
| EPSKYGDKHCPPCP | SEQ ID No: 258 |
| ESKSYGPPHCPPCP | SEQ ID No: 259 |
| ESKSYGDKHCPPCP | SEQ ID No: 260 |
| EPKSCDKTHTCPPCP | SEQ ID No: 261 |
| EPKSCDKTHTCPSCP | SEQ ID No: 262 |
| ESKYCPPACPSCP | SEQ ID No: 263 |
| ESKYCPPAACPSCP | SEQ ID No: 264 |
| ESKYCPPAAACPSCP | SEQ ID No: 265 |
| ESKYCPPAAASPSCP | SEQ ID No: 266 |
| ESKYCPPAAACPSSP | SEQ ID No: 267 |
| ESKCGPPAAACPSCP | SEQ ID No: 268 |
| ESKYCPPAAAACPSCP | SEQ ID No: 269 |
| ESKYCPPAAAAACPSCP | SEQ ID No: 270 |
| ESKYCPPGGGCPSCP | SEQ ID No: 271 |
| ESKYCPPSSSCPSCP | SEQ ID No: 272 |
| ESKYCPPTCPSCP | SEQ ID No: 273 |
| ESKYCPPTHCPSCP | SEQ ID No: 274 |
| ESKYCPPTHTCPSCP | SEQ ID No: 275 |
| ESKYCPKTHTCPSCP | SEQ ID No: 276 |
| ESKYCDKTHTCPSCP | SEQ ID No: 277 |
| ESKYCDKTHCPSCP | SEQ ID No: 278 |
| ESKYCDKTCPSCP | SEQ ID No: 279 |
| ESKYCDKAAACPSCP | SEQ ID No: 280 |
| ESKYCDKCPSCP | SEQ ID No: 281 |
| ESKSCDKTHTCPSCP | SEQ ID No: 282 |
| EPKYCDKTHTCPSCP | SEQ ID No: 283 |
| EPKSCPPCPSCP | SEQ ID No: 284 |
| ESKSCPPCPSCP | SEQ ID No: 285 |
| EPKYCPPCPSCP | SEQ ID No: 286 |
| ECKYGPPCPSCP | SEQ ID No: 287 |
| ECKYGPPSPSCP | SEQ ID No: 288 |
| ECKYGPPCPSSP | SEQ ID No: 289 |
| ESCYGPPCPSCP | SEQ ID No: 290 |
| ESCYGPPSPSCP | SEQ ID No: 291 |

| | |
|---|---|
| ESCYGPPCPSSP | SEQ ID No: 292 |
| ESKCGPPCPSCP | SEQ ID No: 293 |
| ESKCGPPSPSCP | SEQ ID No: 294 |
| ESKCGPPCPSSP | SEQ ID No: 295 |

Antibodies according the present invention also show comparable affinity towards the target antigen compared the wild-type IgG4 antibody.

The mutations to the antibodies of the present invention will now be described in further detail. The methods for replacing amino acids are well known in the art of molecular biology. Such methods include for example site directed mutagenesis using methods such as PCR to delete and/or substitute amino acids or de novo design of synthetic sequences.

FIG. 2a shows the hinge residues of IgG1 wild type, IgG4 wild type and the positions where mutations have been introduced in the antibodies of the present invention. Numbering based on Kabat numbering system.

The antibodies according to the present invention comprise a mutation at position 127 (C127), wherein the cysteine residue is replaced by another amino acid, preferably an amino acid that does not contain a thiol group. By replace or substitute we mean that where the interchain cysteine 127 would normally be found in the antibody heavy chain another amino acid is in its place. The mutation at C127 may be any suitable mutation to one, two or three of the nucleotides encoding the amino acid at position 127 which changes the amino acid residue from cysteine to another suitable amino acid. Examples of suitable amino acids include serine, threonine, alanine, glycine or any polar amino acid. A particularly preferred amino acid is serine.

The substitution of the cysteine at position 127 with another amino acid removes the cysteine in the $C_H1$ domain which normally forms a disulphide bond with a cysteine in the light chain in the wild-type IgG4. Therefore, in order to form a light chain and heavy chain pairing via an inter-chain disulphide bond the light chain must form a disulphide bond with a cysteine which is positioned in the hinge region of the heavy chain.

In a first aspect of the invention, antibodies according to the present invention comprise a heavy chain wherein one or more of the amino acids at positions selected from 227, 228, 229 and 230, numbered according to the Kabat numbering system, is substituted with cysteine. Accordingly, antibodies according to the present invention may carry one or more of the following mutations:

S227C
K228C
Y229C
G230C

Preferably only one residue selected from 227, 228, 229 and 230 is substituted with a cysteine residue.

Particularly preferred antibodies of the present invention carry the mutation Y229C or G230C.

The inclusion of a cysteine residue at a position selected from 227, 228, 229 and 230, in the hinge region of the heavy chain provides a new position for an inter-chain disulphide bond to form between the heavy chain and the light chain. It has been found by the present inventors that this new inter-chain disulphide bond arrangement provides IgG4 antibodies having improved thermostability compared to a wild-type IgG4 antibody.

Further mutations may be introduced to the antibodies of this aspect of the present invention. In one embodiment the cysteine at position 239 (C239) and/or the cysteine at position 242 (C242), numbered according to the Kabat numbering system, in the heavy chain are substituted with another amino acid, preferably an amino acid that does not contain a thiol group. By replace or substitute we mean that where the cysteine 239 and/or the cysteine 242 would normally be found in the antibody heavy chain another amino acid is in its place. The mutation at C239 and/or C242 may be any suitable mutation to one, two or three of the nucleotides encoding the amino acid which changes the amino acid residue from cysteine to another suitable amino acid. Examples of suitable amino acids include serine, threonine, alanine, glycine or any polar amino acid. A particularly preferred amino acid is serine.

In one embodiment the cysteine at position 239 in the heavy chain is substituted with another amino acid and the cysteine at position 242 in the heavy chain is substituted with another amino acid. In this embodiment, the substitution of both C239 and C242 removes both cysteine residues in the hinge region of the heavy chain which normally form inter-heavy chain disulphide bonds with the corresponding cysteines in another heavy chain. The resulting half-molecules may form whole antibody molecules through non-covalent bonding between two heavy chains.

In an alternative embodiment the cysteine at position 239 in the heavy chain is substituted with another amino acid. In this embodiment the cysteine at position 242 is not substituted with another amino acid.

In a further alternative embodiment the cysteine at position 242 in the heavy chain is substituted with another amino acid. In this embodiment the cysteine at position 239 is not substituted with another amino acid.

The substitution of either C239 or C242, leaves one cysteine in the heavy chain which is capable of forming an inter-heavy chain disulphide bond with a cysteine in another heavy chain. Without being bound by theory it is thought that the substitution of one cysteine in the hinge region, particularly substitution of C239, reduces the formation of an intra-chain disulphide bond in the hinge region and therefore may reduce the formation of half antibody molecules.

In one embodiment of the present invention, wherein the serine at position 227 is substituted with a cysteine, the antibody preferably does not comprise mutations at positions C239 and C242. In another embodiment, wherein the serine at position 227 is substituted with a cysteine, the cysteine at position 239 in the heavy chain is preferably substituted with another amino acid but the cysteine at position 242 is not substituted with another amino acid.

In one embodiment the antibodies of the present invention comprise an IgG4 heavy chain which is mutated to insert one or more amino acids between amino acids 226-243. The number of amino acids inserted may be 1 to 10, 1 to 5, 1 to 3, preferably 1, 2, 3 or 4 amino acids are inserted. The amino acids are preferably inserted between amino acids 238 and 239. Any suitable amino acids may be inserted in the hinge region, such as alanines, glycines, serines or threonines and combinations thereof. Preferably three alanines (AAA), three glycines (GGG), three serines (SSS) or three threonines (TTT) are inserted or a threonine, histidine and another threonine (THT). It has been found that antibodies of the present invention comprising an IgG4 heavy chain which has been mutated to insert three amino acids in the hinge region show improved thermostability.

A further mutation which may be introduced in the antibodies according to the present invention is the mutation S241P. This mutation has been previously shown to reduce the formation of half molecules (Angal, S. et al., 1993. A single amino acid substitution abolishes the heterogeneity of chimeric mouse/human (IgG4) antibody. Mol Immunol 30, 105-108).

The antibodies according to the present invention may comprise one or more further mutations in the hinge region. For example the antibodies may further comprise one or more of the following mutations S227P, Y229S, P237D and P238K.

In one embodiment the antibody according to the present invention effectively comprises an IgG1 hinge region from residue 226 to 243 (upper hinge and core hinge). Accordingly, the antibody of the present invention comprises a hinge region wherein the glycine at position 230 is substituted with cysteine, the serine at position 227 is substituted with proline, the tyrosine at position 229 is substituted with serine, the proline at position 237 is substituted with aspartic acid, the proline at position 238 is substituted with lysine, the amino acid sequence threonine-histidine-threonine is inserted between positions 238 and 239 and the serine at position 241 is substituted with proline. These mutations may also be written as S227P, Y229S, G230C, P237D, P238KTHT and S241P, as shown in FIG. 2a. It has been found that the introduction of these further mutations to the IgG4 hinge region provides an antibody having improved thermostability.

The antibody according to the present invention preferably has an IgG4 lower hinge from residue 244 to 251 (APEFLGGP). Without being bound by theory it is believed that the IgG4 lower hinge region contributes to the lack of effector function of an IgG4 antibody.

In a second aspect of the present invention, the antibody comprises a heavy chain wherein the cysteine at position 127 is substituted with another amino acid, as described above, and the cysteine at position 239 or the cysteine at position 242, numbered according to the Kabat numbering system, in the heavy chain is substituted with another amino acid. In this second aspect, none of the residues at positions 227, 228, 229 and 230 are substituted with a cysteine residue.

Antibodies according to the second aspect of the present invention have surprisingly been found to have improved thermostability compared to a wild-type IgG4 antibody.

In the second aspect of the present invention, the antibody may comprise one or more further mutations. In one embodiment the antibody comprises an IgG4 heavy chain which is mutated to insert three amino acids between amino acids 226-243, preferably between amino acids 238 and 239, as described above. In a further embodiment the antibody comprises the mutation S241P. In a further embodiment, the antibody may further comprise one or more of the following mutations S227P, Y229S, P237D and P238K.

Table 1 below lists example antibodies of the present invention and the mutations which have been introduced compared to the IgG4 wild-type sequence. Table 1 also includes wild-type IgG1 and IgG4 antibodies and control antibodies.

TABLE 1

| Antibody Number | Heavy Chain Mutations (Kabat Numbering) | $C_H1$ domain & hinge SEQ ID NO: | $C_H1$, Hinge, $C_H2$ & $C_H3$ SEQ ID NO: |
|---|---|---|---|
| 1 | C127S | — | — |
| 2 | C127S, C239S | 33 | 59 |
| 3 | C127S, C242S | 34 | 60 |
| 6 | C127S, G230C, C239S | 12 | 38 |
| 7 | C127S, G230C, C242S | 13 | 39 |
| 8 | C127S, G230C, C239S, C242S | 14 | 40 |
| 12 | C239S | — | — |
| 13 | C242S | — | — |
| 15 | C127S, G230C | 15 | 41 |
| 16 | C127S, G230C, S241P | 16 | 42 |
| 17 | Human IgG4 wild type | 2 | — |
| 18 | S241P | — | — |
| 19 | Human IgG1 wild type | 1 | — |
| 28 | C127S Y229C | 17 | 43 |
| 28P | C127S Y229C, S241P | 36 | 62 |
| 29 | C127S Y229C C239S | 18 | 44 |
| 30 | C127S Y229C C242S | 19 | 45 |
| 31 | C127S Y229C C239S C242S | 20 | 46 |
| 32 | C127S K228C | 21 | 47 |
| 33 | C127S K228C C239S | 22 | 48 |
| 34 | C127S K228C C242S | 23 | 49 |
| 35 | C127S K228C C239S C242S | 24 | 50 |
| 36 | C127S S227C | 25 | 51 |
| 37 | C127S S227C C239S | 26 | 52 |
| 38 | C127S S227C C242S | 27 | 53 |
| 39 | C127S S227C C239S C242S | 28 | 54 |
| 44 | C127S G230C P238PAAA | 29 | 55 |
| 44P | C127S G230C P238PAAA, S241P | 37 | 63 |
| 45 | C127S G230C P238PAAA C239S | 30 | 56 |
| 46 | C127S G230C P238PAAA C242S | 31 | 57 |
| 47 | C127S G230C P238PAAA C239S C242S | 32 | 58 |
| 48 | C127S, S227P, Y229S, G230C, P237D, P238KTHT, S241P | 35 | 61 |
| 49 | C127S G230C P232PA | | |
| 50 | C127S G230C P232PAA S241P | | |
| 51 | C127S, G230C, P232PAAAA | | |
| 52 | C127S, G230C, P232PAAAAA | | |
| 55 | C127S, G230C, P232PTHT | | |
| 56 | C127S, G230C, P231D, P232KTHT | | |
| 57 | C127S, G230C, P232PGGG | | |
| 60 | C127S, S227P, G230C | | |
| 62 | C127S, Y229S, G230C | | |
| 64 | C127S, S227P, Y229S, G230C | | |
| 65 | P237D, P238KTHT | | |
| 66 | C127S, G230C, P231D, P232KTH | | |
| 67 | C127S, G230C, P231D, P232KT | | |
| 68 | C127S, G230C, P231D, P232K | | |
| 69 | C127S, G230C P231D, P232KAAA | | |
| 71 | C127S, S227P, G230C, P231D, P232KTHT | | |
| 73 | C127S, Y229S, G230C, P231D, P232KTHT | | |

FIGS. 3a and 4a also show the mutations introduced in IgG4 antibodies according to the present invention. FIGS. 3b and 4b show the positions of the cysteine residues in the IgG4 antibodies of the present invention and also show the predicted bonding of the cysteine to a cysteine in the light chain (LC) or another heavy chain (HC). For cysteine residues which show (LC or HC), it is possible that the cysteine is binding to a cysteine in the light chain or the heavy chain but where either the LC or HC is underlined this is the disulphide bond which is believed to predominantly occur.

In a preferred embodiment, the present invention provides an antibody comprising at least one heavy chain, wherein each heavy chain comprises a $C_H1$ domain and a hinge region and each heavy chain comprises the mutations of an antibody selected from 2, 3, 6, 7, 8, 15, 16, 28, 28P, 29, 30, 31, 32, 33, 34, 35, 36, 37, 38, 39, 44, 44P, 45, 46, 47 and 48, as shown in Table 1. Accordingly, the present invention provides an antibody comprising at least one heavy chain, wherein each heavy chain comprises a $C_H1$ domain and a hinge region and each heavy chain comprises one of the following sequences: SEQ ID NO: 12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO: 36 and SEQ ID NO: 37.

In a preferred embodiment the antibody of the present invention comprises at least one heavy chain wherein each heavy chain comprises a $C_H1$ domain and a hinge region, and comprises one of the following sequences: SEQ ID NO: 12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:29, SEQ ID NO:30, SEQ ID NO:31, SEQ ID NO:32 SEQ ID NO:35, SEQ ID NO: 36 and SEQ ID NO: 37. More preferably, the antibody of the present invention comprises at least one heavy chain wherein each heavy chain comprises a $C_H1$ domain and a hinge region and each heavy chain comprises one of the following sequences: SEQ ID NO: 12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:29, SEQ ID NO:30, SEQ ID NO:31, SEQ ID NO:32 SEQ ID NO:35, SEQ ID NO: 36 and SEQ ID NO: 37.

In a further preferred embodiment, the present invention provides an antibody comprising at least one heavy chain, wherein each heavy chain comprises a $C_H1$ domain, a hinge region, a $C_H2$ domain and a $C_H3$ domain and each heavy chain comprises the mutations of an antibody selected from 2, 3, 6, 7, 8, 15, 16, 28, 28P, 29, 30, 31, 32, 33, 34, 35, 36, 37, 38, 39, 44, 44P, 45, 46, 47 and 48, as shown in Table 1. Accordingly, the present invention provides an antibody comprising at least one heavy chain, wherein each heavy chain comprises a $C_H1$ domain, a hinge region, a $C_H2$ domain and a $C_H3$ domain and each heavy chain comprises one of the following sequences: SEQ ID NO: 38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO: 62 and SEQ ID NO: 63.

A particularly preferred antibody of the present invention comprises at least one heavy chain which comprises a $C_H1$ domain and a hinge region, wherein the heavy chain comprises SEQ ID NO:36 (antibody 28P), SEQ ID NO: 37 (antibody 44P) or SEQ ID NO:35 (antibody 48). A further particularly preferred antibody of the present invention comprises at least one heavy chain which comprises a $C_H1$ domain, a hinge region, a $C_H2$ domain and a $C_H3$ domain wherein the heavy chain comprises SEQ ID NO:62 (antibody 28P), SEQ ID NO: 63 (antibody 44P) or SEQ ID NO:61 (antibody 48). Antibodies 28P, 44P and 48 are particularly preferred because they exhibit significantly improved thermostability and further exhibit reduced half-molecule formation.

Antibodies 2, 3 and 8 have been shown to form significant quantity of so-called half-molecules (HL). These mutants may form whole antibody molecules (H2L2) in vitro under non-denaturing conditions but any non-covalent associations between the heavy chains and/or between heavy and light chains is removed under non-reducing SDS-PAGE conditions. Whilst it often taught to be desirable to reduce the formation of half-molecules, antibodies which have an increased tendency to form half-molecules may be advantageous for certain uses. Antibodies which form stable half-molecules (HL) and little or no whole antibody (H2L2) due to the antibody heavy chain being incapable to form a covalent or non-covalent association with another heavy chain are of particular interest. Antibodies which form stable half-molecules may be advantageous for the production of monovalent antibodies. Antibodies which form half-molecules may also provide a useful way to produce a bispecific antibody due to the formation of whole antibodies from half-molecules having different specificities, wherein the whole antibody is bispecific and monovalent for each antigen.

Antibody 3 retains C239 in the hinge region but appears unable to form interhinge heavy chain disulphide bonds, presumably due to efficient formation of a disulphide between the C-terminal light chain cysteine and the hinge C239. A comparison of antibodies 2 and 3 shows the extent of the 'reach' of the C-terminal cysteine of the light chain, in that the light chain disulphide bonds more efficiently to C239 than to C242 in the hinge region. Furthermore antibody 3 shows increased stability compared to antibody 2.

Whilst the mutated antibodies according to the present invention are described above with respect to the IgG4 isotype, the skilled person will appreciate that the mutations made to the IgG4 antibody may also be applied to other antibody isotypes or classes which have the same disulphide bond arrangement as an IgG4 antibody in order to provide an improved antibody. Specific examples of antibodies which have the same disulphide bond arrangement as an IgG4 antibody are IgG3 antibodies, IgM antibodies and IgD antibodies. As shown in FIG. 1b, IgG3 and IgM have a cysteine at position 127 in the $C_H1$ domain and IgD has a cysteine at position 128 in the $C_H1$ domain which is equivalent to the C127 in the $C_H1$ domain of IgG4 which forms an inter-chain disulphide bond with a cysteine in the light chain. Further, it can also be seen from FIG. 1b that upper hinge regions of IgG3 and IgD and the C-terminal region of the $C_H1$ domain and the N-terminal region of the $C_H2$ domain in IgM do not contain a cysteine residue which is equivalent to the residues of the upper hinge region of IgG1. Accordingly, the present invention further provides an IgG3 antibody, an IgD antibody and an IgM antibody wherein the cysteine in the $C_H1$ domain which forms an inter-chain disulphide bond with a cysteine in a light chain is substituted with another amino acid and wherein one or more amino acids which are in a structurally analogous position to the upper hinge region of IgG1 or IgG4 are substituted with cysteine.

Accordingly, the present invention also provides an antibody of the class IgG3 comprising at least one heavy chain which comprises a $C_H1$ domain and a hinge region, wherein in each heavy chain:
  a. the cysteine in the $C_H1$ domain which forms an inter-chain disulphide bond with a cysteine in a light chain is substituted with another amino acid; and
  b. one or more of the amino acids positioned in the upper hinge region is substituted with cysteine.

In a preferred embodiment of the IgG3 antibody aspect of the present invention, the cysteine in the $C_H1$ domain which forms an inter-chain disulphide bond with a cysteine in a light chain is the cysteine at position 127, numbered according to the Kabat numbering system, as shown in FIGS. 1b and 2b.

In a preferred embodiment of the IgG3 antibody aspect of the present invention, the one or more amino acids positioned in the upper hinge region which may be substituted with cysteine are one or more of the amino acids at positions selected from 226, 227, 228 229, 230, 232 and 233, numbered according to the Kabat numbering system, as shown in FIGS. 1b and 2b.

The present invention further provides an antibody of the class IgM comprising at least one heavy chain which comprises a $C_H1$ domain and a $C_H2$ domain, wherein in each heavy chain:
 a. the cysteine in the $C_H1$ domain which forms an inter-chain disulphide bond with a cysteine in a light chain is substituted with another amino acid; and
 b. one or more of the amino acids positioned in the $C_H1$ domain or $C_H2$ domain is substituted with cysteine.

In a preferred embodiment of the IgM antibody aspect of the present invention, the cysteine in the $C_H1$ domain which forms an inter-chain disulphide bond with a cysteine in a light chain is the cysteine at position 127, numbered according to the Kabat numbering system, as shown in FIGS. 1b and 2c.

In a preferred embodiment of the IgM antibody aspect of the present invention, one or more amino acids positioned in the C-terminal end of the $C_H1$ domain or the N-terminal end of the $C_H2$ domain are substituted with cysteine. Preferred amino acids position in the C-terminal end of the $C_H1$ domain which may be substituted with cysteine are one or more of the amino acids at positions selected from 223, 223A, 223B and 223C, numbered according to the Kabat numbering system, as shown in FIGS. 1b and 2c. Preferred amino acids position in the N-terminal end of the $C_H2$ domain which may be substituted with cysteine are one or more of the amino acids at positions selected from 243G, 243H and 243I, numbered according to the Kabat numbering system, as shown in FIGS. 1b and 2c. Accordingly any one or more of amino acids 223 to 243 may be substituted with cysteine.

The present invention further provides an antibody of the class IgD comprising at least one heavy chain which comprises a $C_H1$ domain and a hinge region, wherein in each heavy chain:
 a. the cysteine in the $C_H1$ domain which forms an inter-chain disulphide bond with a cysteine in a light chain is substituted with another amino acid; and
 b. one or more of the amino acids positioned in the hinge region is substituted with cysteine.

In a preferred embodiment of the IgD antibody aspect of the present invention, the cysteine in the $C_H1$ domain which forms an inter-chain disulphide bond with a cysteine in a light chain is the cysteine at position 128 numbered according to the Kabat numbering system, as shown in FIGS. 1b and 2d.

The hinge region of an IgD antibody may be defined as R224-P243, according to the Kabat numbering system.

In a preferred embodiment of the IgD antibody aspect of the present invention, the one or more amino acids positioned in the hinge region which are substituted with cysteine are one or more of the amino acids at positions selected from 227, 228, 229, 230, 231, 232 and 233, numbered according to the Kabat numbering system, as shown in FIGS. 1b and 2d.

The IgG3, IgD or IgM antibodies provided by the present invention may comprise one or more further mutations to the hinge region as discussed above with respect to the IgG4 antibody.

The term 'antibody' as used herein includes intact (whole) antibodies and functionally active fragments which comprise at least one heavy chain which comprises a $V_H$ domain, a $C_H1$ domain and a hinge region. The antibody according to the present invention preferably comprises at least one light chain. Accordingly, the term "antibody" in the present invention covers bi, tri or tetra-valent antibodies, Fab' and $F(ab)_2$ fragments, half-antibody molecules or half-molecules comprising a single light chain and heavy chain pairing and whole antibody molecules comprising two light chain and heavy chain pairings.

As is well known in the art, a typical Fab' molecule comprises a heavy and a light chain pair in which the heavy chain comprises a variable region $V_H$, a constant domain CH1 and a hinge region and the light chain comprises a variable region VL and a constant domain CL.

In one embodiment there is provided a dimer of Fab' according to the present disclosure for example dimerisation may be through the hinge.

In one embodiment the heavy chain comprises a $C_H2$ domain and a $C_H3$ domain and optionally a $C_H4$ domain. In one embodiment the antibody comprises two heavy chains each of which is as defined above in the first or second aspect of the present invention. The antibodies according to the present invention also preferably comprise two light chains. In this embodiment wherein the antibody comprises two heavy chains, preferably both heavy chain sequences are identical as defined above by the first or second aspect of the present invention.

In a preferred embodiment the antibody of the present invention is a whole antibody comprising two light chains and two heavy chains, wherein each heavy chain comprises an IgG4 CH1 wherein the cysteine at position 127, numbered according to the Kabat numbering system is substituted with another amino acid, an IgG1 upper and middle hinge region, an IgG4 lower hinge region, a $C_H2$ domain and a $C_H3$ domain.

The complete hinge region of an IgG4 antibody typically consists of residues 226 to 251 (numbering based on Kabat numbering system. However the hinge region may be shortened or lengthened as required. For example, antibodies according to the first aspect of the present invention, the wild type amino acid is substituted with a cysteine residue at position 227, 228, 229 or 230, the hinge region may end after the new cysteine residue at position 227, 228, 229 or 230. Antibodies according to the present invention may also comprise one or more further amino acids positioned N-terminal and/or C-terminal of the hinge region. In addition other characteristics of the hinge can be controlled, such as the distance of the hinge cysteine(s) from the light chain interchain cysteine, the distance between the cysteines of the hinge and the composition of other amino acids in the hinge that may affect properties of the hinge such as flexibility e.g. glycines may be incorporated into the hinge to increase rotational flexibility or prolines may be incorporated to reduce flexibility. Alternatively combinations of charged or hydrophobic residues may be incorporated into the hinge to confer multimerisation or purification properties. Other modified hinge regions may be entirely synthetic and may be designed to possess desired properties such as length, composition and flexibility.

The constant region domains, in particular in the Fc domain, where present, employed in the present invention, are preferably of IgG4 isotype where antibody effector functions are not required. According each heavy chain preferably comprises an IgG4 $C_H2$ domain and a $C_H3$ domain, as shown in SEQ ID NO:64.

It will be appreciated that sequence variants of the Fc constant region domains may also be used.

In one embodiment each heavy chain comprises IgG4 $C_H2$ and $C_H3$ domains wherein the arginine at position 409 (EU numbering) is substituted with lysine, threonine, methionine or leucine in order to inhibit aggregate formation at low pH (US 2008/0063635 Takahashi et al.) Mutations at L235, D265, D270, K322, P331 and P329 (numbered according to EU numbering system) are also taught in order to attenuate CDC activity (US 2008/0063635 Takahashi et al.).

Each heavy chain may comprise the mutations as taught in WO2008/145142 Van de Winkel et al. which discloses stable IgG4 antibodies that have a reduced ability to undergo Fab-arm exchange by substitution of the arginine residue at position 409, the Phe residue at position 405 or the Lys at position 370 (numbered according to EU numbering system).

In one embodiment each heavy chain comprises an IgG4 $C_H2$ domain and an IgG1 $C_H3$ domain, as shown in SEQ ID NO:65.

In the embodiment of the present invention wherein the antibody is a mutated IgG3, IgD or IgM antibody, each heavy chain preferably comprises a $C_H2$ domain and a $C_H3$ domain, and optionally a $C_H4$ domain. In the IgG3 antibody each heavy chain preferably comprises IgG3 $C_H2$ domain and a IgG3 $C_H3$ domain. In the IgD antibody each heavy chain preferably comprises IgD $C_H2$ domain and a IgD $C_H3$ domain. In the IgM antibody each heavy chain preferably comprises IgM $C_H2$ domain, a IgM $C_H3$ domain and a IgM $C_H4$ domain.

In one embodiment, the antibody is a monoclonal, fully human, humanized or chimeric antibody fragment. In one embodiment the antibody is fully human or humanised.

Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA*, 1996, 93(15), 7843-7848, WO 92/02551, WO2004/051268 and WO2004/106377.

Humanized antibodies are antibody molecules from non-human species having one or more complementarity determining regions (CDRs) from the non-human species and a framework region from a human immunoglobulin molecule which optionally comprise one or more donor residues from the non-human species (see, for example, U.S. Pat. No. 5,585,089).

The antibodies for use in the present invention can also be generated using various phage display methods known in the art and include those disclosed by Brinkman et al., *J. Immunol. Methods*, 1995, 182, 41-50; Ames et al., *J. Immunol. Methods*, 1995, 184, 177-186; Kettleborough et al. *Eur. J. Immunol.*, 1994, 24, 952-958; Persic et al., *Gene*, 1997 187, 9-18; and Burton et al., *Advances in Immunology*, 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403, 484; 5,580,717; 5,427,908; 5,750,753; 5,821,047; 5,571, 698; 5,427,908; 5,516,637; 5,780,225; 5,658,727; 5,733, 743; and 5,969,108. Also, transgenic mice, or other organisms, including other mammals, may be used to generate humanized antibodies.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and/or constant region genes have been replaced by their human counterparts eg. as described in general terms in EP0546073 B1, U.S. Pat. Nos. 5,545,806, 5,569,825, 5,625,126, 5,633,425, 5,661,016, 5,770,429, EP 0438474 B1 and EP0463151 B1.

The antibody starting material for use in the present invention may be prepared by the use of recombinant DNA techniques involving the manipulation and re-expression of DNA encoding the antibody variable and constant region(s). Standard molecular biology techniques may be used to modify, add or delete amino acids or domains as desired. Any alterations to the variable or constant regions are still encompassed by the terms 'variable' and 'constant' regions as used herein.

The antibody starting material may be obtained from any species including for example mouse, rat, rabbit, hamster, camel, llama, goat or human. Parts of the antibody may be obtained from more than one species, for example the antibody may be chimeric. In one example, the constant regions are from one species and the variable regions from another. The antibody starting material may also be modified. In another example, the variable region of the antibody has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing these antibodies are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

In one embodiment the antibody comprises a variable domain pair forming a binding domain is a cognate pair. Cognate pair as employed herein is intended to refer to a natural pair of variable domains, that is to say isolated from a single antibody or antibody expressing cell.

Variable domains may have been optimized and/or humanized.

Optimised/humanized variable domains derived from a cognate pair will still be considered a cognate pair after optimization/humanization.

Thus the invention extends to human, humanized or chimeric molecules.

In one embodiment the molecule specifically binds a target antigen. Specifically binds as employed herein is intended to refer to molecules having high affinity for a target antigen (to which it is specific) and which binds antigens to which it is not specific with a low or much lower affinity (or not at all). Methods of measuring affinity are known to those skilled in the art and include such assays as BIAcore™.

The antibody molecules of the present invention suitably have a high binding affinity, in particular, nanomolar or picomolar. Affinity may be measured using any suitable method known in the art, including BIAcore™. In one embodiment the molecule of the present invention has a binding affinity of about 100 pM or better. In one embodiment the molecule of the present invention has a binding affinity of about 50 pM or better. In one embodiment the molecule of the present invention has a binding affinity of about 40 pM or better. In one embodiment the molecule of the present invention has a binding affinity of about 30 pM or better. In one embodiment the molecule of the present invention is fully human or humanised and has a binding affinity of about 100 pM or better.

A derivative of a naturally occurring domain as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained.

In one embodiment the antibody molecules of the present invention comprise one or more albumin binding peptides. In vivo the peptide binds albumin, which increases the half-life of the molecule.

The albumin binding peptide may be appended from one or more variable regions, a hinge or C-terminal of the molecule or any location that does not interfere with the molecules antigen binding properties.

Examples of albumin binding peptides are provided in WO 2007/106120.

It will also be understood by one skilled in the art that the antibody may undergo a variety of posttranslational modifications. The type and extent of these modifications often depends on the host cell line used to express the molecule as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995).

If desired a molecule for use in the present invention may be conjugated to one or more effector molecule(s). It will be appreciated that the effector molecule may comprise a single effector molecule or two or more such molecules so linked as to form a single moiety that can be attached to the antibody molecule of the present invention. Where it is desired to obtain an antibody according to the invention linked to an effector molecule, this may be prepared by standard chemical or recombinant DNA procedures in which the antibody is linked either directly or via a coupling agent to the effector molecule. Techniques for conjugating such effector molecules to an antibody are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotr exate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, $Lu^{177}$, $Bismuth^{213}$, $Californium^{252}$, $Iridium^{192}$ and $Tungsten^{188}$/$Rhenium^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM- CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO 05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody of the disclosure and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example an antibody for use in the present invention is attached to poly(ethyleneglycol) (PEG) moieties. In one particular example the PEG molecules may be attached through any available amino acid side-chain or terminal amino acid functional group located in the antibody, for example any free amino, imino, thiol, hydroxyl or carboxyl group. Such amino acids may occur naturally in the antibody or may be engineered into the antibody using recombinant DNA methods (see for example U.S. Pat. Nos. 5,219,996; 5,667,425; WO 98/25971). In one example the molecule of the present invention is a modified antibody wherein the modification is the addition to the C-terminal end of its heavy chain one or more amino acids to allow the attachment of an effector molecule. Multiple sites can be used to attach two or more PEG molecules.

In one embodiment a PEG molecule is linked to a cysteine 171 in the light chain, for example see WO2008/038024 incorporated herein by reference.

Suitably PEG molecules are covalently linked through a thiol group of at least one cysteine residue located in the antibody. Each polymer molecule attached to the modified antibody may be covalently linked to the sulphur atom of a cysteine residue located in the antibody. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

The present invention also provides isolated DNA encoding an antibody molecule described herein.

In a further aspect there is provided a vector comprising said DNA.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

In a further aspect there is provided a host cell comprising said vector and/or DNA.

Any suitable host cell/vector system may be used for expression of the DNA sequences encoding the molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule as described herein comprising culturing a host cell containing a vector (and/or DNA) of the present invention under conditions suitable for leading to expression of protein from DNA encoding an antibody molecule of the present invention, and isolating an antibody molecule.

For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibody molecules according to the present disclosure are expressed at suitable levels from host cells making them conducive to commercial processing.

The antibody may be specific for any target antigen. The antigen may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD40L, CD45, CDW52, CD69, CD134 (OX40), ICOS, BCMP7, CD137, CD27L, CDCP1, CSF1 or CSF1-Receptor, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, KDR and VEGF, PD-1, DC-SIGN, TL1A, DR3, IL-7 receptor A and where appropriate, receptors thereof.

Soluble antigens include interleukins such as IL-1, IL-2, IL-3, IL-4, IL-5, IL-6, IL-8, IL-12, IL-13, IL-14, IL-16 or IL-17, such as IL17A and/or IL17F, viral antigens for example respiratory syncytial virus or cytomegalovirus antigens, immunoglobulins, such as IgE, interferons such as interferon α, interferon β or interferon γ, tumour necrosis factor TNF (formerly known as tumour necrosis factor-α and referred to herein as TNF or TNFα), tumor necrosis factor-β, colony stimulating factors such as G-CSF or GM-CSF, and platelet derived growth factors such as PDGF-α, and PDGF-β, WISP-1 and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody may be used to functionally alter the activity of the antigen of interest. For example, the antibody may neutralize, antagonize or agonise the activity of said antigen, directly or indirectly.

The antibody molecules of the present invention are useful in the treatment and/or prophylaxis of a pathological condition.

Thus there is provided an antibody according to the present invention for use in treatment, by administering a therapeutically effective amount thereof, for example in a pharmaceutical formulation. In one embodiment the antibody according to the invention is administered topically to the lungs, for example by inhalation.

The antibodies provided by the present invention are useful in the treatment of diseases or disorders including inflammatory diseases and disorders, immune disease and disorders, fibrotic disorders and cancers.

The term "inflammatory disease" or "disorder" and "immune disease or disorder" includes rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease.

The term "fibrotic disorder" includes idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery.

The term "cancer" includes a malignant new growth that arises from epithelium, found in skin or, more commonly, the lining of body organs, for example: breast, ovary, prostate, lung, kidney, pancreas, stomach, bladder or bowel. Cancers tend to infiltrate into adjacent tissue and spread (metastasise) to distant organs, for example: to bone, liver, lung or the brain.

The present invention also provides a pharmaceutical or diagnostic composition comprising an antibody of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody of the present invention together with one or more of a pharmaceutically acceptable excipient, diluent or carrier.

The antibody of the disclosure may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody or composition according to the disclosure is employed in combination with a further pharmaceutically active agent, for example a corticosteroid (such as fluticasonoe propionate) and/or a beta-2-agonist (such as salbutamol, salmeterol or formoterol) or inhibitors of cell growth and proliferation (such as rapamycin, cyclophosphmide, methotrexate) or alternative a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. The therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which an antibody of the present invention is administered depends on the nature of the condition to be treated, for example the extent of the disease/inflammation present and on whether the molecule is being used prophylactically or to treat an existing condition.

The frequency of dose will depend on the half-life of the antibody and the duration of its effect. If the antibody has a short half-life (e.g. 2 to 10 hours) it may be necessary to give one or more doses per day. Alternatively, if the antibody has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the molecule of the disclosure may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody, for example if the pH of the formulation is 7 then a pI of from 8-9 or above may be appropriate. Whilst not wishing to be bound by theory it is thought that this may ultimately provide a final formulation with improved stability, for example the antibody remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the antibody) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the above-mentioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 mL of water so as to achieve a pH of about 4.0 to 5.0. A suspension can employ, for example, lyophilised molecule.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the for the formulation, aseptic suspension of the molecule in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibody of the present disclosure are thought to be particularly suitable for delivery via nebulisation.

Comprising in the context of the present specification is intended to meaning including.

Where technically appropriate embodiments of the invention may be combined.

The invention will now be described with reference to the following examples, which are merely illustrative and should not in any way be construed as limiting the scope of the present invention.

EXAMPLES

1 Mutagenesis of IgG4 Heavy Chain and Generating Mutated IgG4 Heavy Chain Single Gene Vectors Amino acid mutations were performed using the Quickchange® Lightening Multi Site Directed Mutagenesis (SDM) kit or the Quickchange® II DSM kit (obtained from Stratagene®) (catalogue numbers 210516 and 200521 respectively) and performed according to manufacturer's instructions.

Mutations were verified by DNA sequencing. The IgG4 heavy chains of at least antibodies 1 to 47 in the following table were produced:

| Antibody Number | Heavy Chain Mutations (Kabat Numbering) | $C_H1$ domain & Hinge SEQ ID NO: | $C_H1$, Hinge, $C_H2$ & $C_H3$ SEQ ID NO: |
|---|---|---|---|
| 1 | C127S | — | — |
| 2 | C127S, C239S | 33 | 59 |
| 3 | C127S, C242S | 34 | 60 |
| 6 | C127S, G230C, C239S | 12 | 38 |
| 7 | C127S, G230C, C242S | 13 | 39 |
| 8 | C127S, G230C, C239S, C242S | 14 | 40 |
| 12 | C239S | — | — |
| 13 | C242S | — | — |
| 15 | C127S, G230C | 15 | 41 |
| 16 | C127S, G230C, S241P | 16 | 42 |
| 17 | Human IgG4 wild type | 2 | — |
| 18 | S241P | — | — |
| 19 | Human IgG1 wild type | 1 | — |
| 28 | C127S Y229C | 17 | 43 |
| 28P | C127S Y229C, S241P | 36 | 62 |
| 29 | C127S Y229C C239S | 18 | 44 |
| 30 | C127S Y229C C242S | 19 | 45 |
| 31 | C127S Y229C C239S C242S | 20 | 46 |
| 32 | C127S K228C | 21 | 47 |
| 33 | C127S K228C C239S | 22 | 48 |
| 34 | C127S K228C C242S | 23 | 49 |
| 35 | C127S K228C C239S C242S | 24 | 50 |
| 36 | C127S S227C | 25 | 51 |
| 37 | C127S S227C C239S | 26 | 52 |
| 38 | C127S S227C C242S | 27 | 53 |
| 39 | C127S S227C C239S C242S | 28 | 54 |
| 44 | C127S G230C P238PAAA | 29 | 55 |
| 44P | C127S G230C P238PAAA, S241P | 37 | 63 |
| 45 | C127S G230C P238PAAA C239S | 30 | 56 |
| 46 | C127S G230C P238PAAA C242S | 31 | 57 |
| 47 | C127S G230C P238PAAA C239S C242S | 32 | 58 |
| 48 | C127S, S227P, Y229S, G230C, P237D, P238KTHT, S241P | 35 | 61 |

Other antibodies prepared are described in table 1 above.

The heavy chain of antibody 48 (Sequence ID NO 35) was generated by PCR and restriction enzyme cloning. The PCR product was generated by a forward oligo encoding the IgG1 upper and core hinge region sequence and a restriction site BglII and a reverse oligo encoding the restriction enzyme DraIII. The PCR fragment was then digested with above mentioned enzymes and ligated into the hG4 single gene vector containing the appropriate variable region.

2. Expression of the Mutated IgG4 Antibodies

All mutant DNA was transfected into CHOK1 cells or CHO-SXE cells. Cells ($2 \times 10^8$ cells/ml) were resuspended in 1 ml Earles Balance Salt Solution (Sigma) and mixed with 400 µg of DNA (200 µg heavy chain DNA and 200 µg kappa light chain DNA). 800 µl aliquots were transferred to 0.4 cm cuvettes (Biorad). For a 500 ml culture, six cuvettes were electroporated under the following parameters: 1 ms, 9.6 Amps; 10 ms, 0 Amps; 40 ms, 3.2 Amps. The transfected cells were incubated for 24 hrs, shaking at 140 rpm in a 5% $CO_2$ humidified environment at 37° C. and continued from day 2 post transfection at 32° C. for 10-13 days. On day 4 post transfection 1.6 mls 1 M sodium butyrate was added to the culture. Once the cells reached 40% viability or up to day 13, the supernatant was harvested. Cultures were centrifuged for 45 minutes at 4000 rpm. The supernatant was put through a 0.22 µM Stericup filter (Millipore) to be purified. Data in FIG. 28 show that changes in IgG4 thermostability encoded by the engineered mutations were the same when the protein was produced from either CHO-K1 or CHO-SXE cells.

3. Purification of Mutated IgG4 Antibodies

Supernatants (200-500 ml) were purified using a Protein A 5 ml HiTrap MabSelect SuRe column (GE Healthcare, Amersham UK). Samples were prepared by adding $\frac{1}{50}^{th}$ of the supernatant volume of 2 M Tris-HCl pH 8.5. Samples were loaded onto the column at 1 ml/min. The column was washed with PBS pH 7.4. To elute the samples, 0.1 M sodium citrate, pH 3.4 was run through the column at 1 ml/min and 0.5 ml fractions were collected. Peak fractions were neutralised by adding 0.125 ml of 2 M Tris-HCl pH8.5 to each. UV detection was set at 280 nm.

4. Characterization of Purified Mutated IgG4 Antibodies

SDS PAGE Analysis:

Crude supernatant was centrifuged at 1200 rpm for 5 mins and quantified on the OCTET. Antibody samples (25-30 ng) were prepared by adding the appropriate amounts of antibody, 4× Loading Buffer (Invitrogen) and 2 µl 100 mM NEM. A total volume of 20 µl was made up using $dH_2O$. The samples were then boiled for 3 mins at 100° C. and loaded onto a 15 well 1.5 mm 4-20% Tris-Glycine gel. Gels were run at 150 V for 1.5 hrs in 1× Tank buffer. Antibodies were transferred to a nitrocellulose membrane using the iBlot dry transfer system set to transfer for 8 mins. The membrane was incubated for 1 hr at room temperature (RT) in PBS-TM on a shaking platform, followed by incubation with a rabbit anti-human IgG Fc HRP conjugated antibody (Jackson Immunoresearch) or goat anti-human Kappa light chain HRP conjugated antibody (Bethyl) for 1 hr, shaking at RT. This was followed by 3 washes of 5 mins each with PBS-T. The blots were revealed using a metal enhanced DAB substrate kit according to the manufacturer's instructions (Pierce).

The results of the Western blot analysis is shown in FIGS. 7, 8, 9 and 10. In FIG. 7-10, H stands for heavy chain and L for light chain, H2L2 is a whole antibody molecule comprising two heavy chains and two light chains and HL is a half molecule comprising one heavy chain and one light chain.

FIG. 7 shows the Western blot analysis for antibodies 15, 16, 6, 7, 8, 17, 18, 19, 1, 2, 3, 12 and 13. It can be seen from FIG. 7 that the antibodies show a good level of H2L2 except for antibody 8 which shows no or very little H2L2 due to the presence of both hinge mutations C239S and C242S. However, antibody 8 can form H2L2 by non-covalent bonding between the heavy chains. Mutant 3 also shows little H2L2, this mutant retains C239 but is unable to form inter heavy chain disulphides in the hinge, presumably due to efficient formation of a disulphide between the C-terminal light chain (LC) cysteine and the hinge C239. It can also be seen that antibodies which comprise the mutation C239S but not C242S (antibodies 2, 6 and 12) show reduced formation of HL compared to antibodies which comprise neither C239S nor C242S or antibodies which comprise C242S but not C239S. Antibody 16 which comprises the S241P mutation also shows reduced formation of HL. A comparison of mutants 2 and 3 shows the extent of the 'reach' of the C-terminal cysteine of light chain to form a disulphide bond with the heavy chain, it appears that the light chain cysteine bonds more efficiently to C239 than to C242 in the heavy chain.

FIG. 8 shows the Western blot analysis for antibodies 15, 6, 7, 8, 28, 29, 30, 31, 17, 19, 32, 33, 33, 34, 35, 36, 37, 38 and 39. It can be seen from FIG. 8 that the antibodies show a good level of H2L2 except for antibodies 8, 31, 35 and 39 which show no or very little H2L2 due to the presence of mutations C239S and C242S in the hinge region and therefore no disulphide bonds form between two heavy chains. However, antibodies 8, 31, 35 and 39 can form H2L2 by non-covalent bonding between the heavy chains. It can also be seen that antibodies which comprise the mutation C239S but not C242S (antibodies 6, 29, 33 and 37) show reduced formation of HL compared to antibodies which comprise neither C239S nor C242S or antibodies which comprise C242S but not C239S. Mutant 15 is able to form a disulphide bond between the light chain and G230C in the CH1 and inter heavy chain disulphides hence resulting in a fully assembled and disulphide bonded protein. Furthermore, a comparison of mutants 15(C127S G230C), 28(C127S Y229C), 32(C127S K228C) and 36(C127S S227C) shows that the position of the introduced cysteine in the upper hinge improves inter LC-HC disulphide bond formation. G230 and Y229 are particularly preferred positions to introduce a cysteine. Mutant 28 (C127S Y229C) shows a low level of HL and H2 and therefore has low disulphide bond heterogeneity.

FIG. 9 shows the Western blot analysis for antibodies 15, 6, 7, 8, 44, 45, 46, 47, 17 and 19. It can be seen from FIG. 9 that the antibodies show a good level of H2L2 except for antibodies 8 and 47 which show no or very little H2L2 due to the presence of mutations C239S and C242S in the hinge region and therefore no disulphide bonds form between two heavy chains. However, antibodies 8 and 47 can form H2L2 by non-covalent bonding between the heavy chains. It can also be seen that antibodies which comprise the mutation C239S but not C242S (antibodies 6 and 45) show reduced formation of HL compared to antibodies which comprise neither C239S nor C242S or antibodies which comprise C242S but not C239S. In particular, mutant 44 shows that insertion of three amino acids in the upper hinge can also reduce the formation of HL and H2 and hence has lower levels of disulphide heterogeneity than the comparable mutant 15.

FIG. 10, shows the Western blot analysis for antibodies 48, 17, 18 and 19. It can be seen from FIG. 10, that antibody 48 shows a good level of H2L2 and very little HL. Mutant 48 contains the IgG1 upper hinge sequence EPKSCDKTHT in place of the IgG4 upper hinge sequence along with a core hinge S241P mutation. Hence mutant 48 has the upper and core hinge sequence EPKSCDKTHTCPPCP. Mutant 48 shows lower levels of disulphide bond heterogeneity compared to the wild type IgG4 antibody 17 and approximately equivalent low levels of disulphide bond heterogeneity compared to the IgG4 S241P mutant 18 and wild type IgG1 antibody 19.

Thermofluor Assay:

Thermostabilities of purified mAbs were analyzed in a thermofluor assay using SYPRO® Orange to monitor the thermal unfolding process of proteins. 5 µl of mAb at 1 mg/ml, 5 µl of 30× dye, and 40 µl of PBS were added together. Ten µl of the mix was dispensed in quadruplicate to a 384 PCR optical well plate and was run on the 7900HT Fast Real-Time PCR System (Agilent Technologies UK Ltd, Wokingham UK). This PCR System contains a heating device for accurate temperature control set at 20° C. to 99° C.; a charged coupled device simultaneously monitors the fluorescence changes in the wells.

FIGS. 11, 12, 13, 14 and 15 show the results of the thermostability analysis of the IgG4 Antibody mutants compared to wild-type IgG1 and IgG4 antibodies.

A comparison of mutant 15 with wild type IgG4 (mutant 17) shows and increase in the Fab Tm due to the altered disulphide arrangement. A comparison of mutant 15 and 28 shows further improvement in Fab Tm for mutant 28 comprising Y229C mutation compared to mutant 15 comprising G230C mutation. A comparison of mutant 15 and 44 shows that the Fab Tm of a G230C mutant can be further increased further by insertion of three amino acids in the upper hinge. Comparison of mutants 17 and 18 show that the S241P middle hinge mutation does not increase Fab Tm even though it significantly reduces HL formation. Mutant 48 also shows significantly improved Fab Tm when compared to both wild type IgG4 (mutant 17) and mutant 15.

FIG. 15 shows the overall ranking of the thermostabilites of selected IgG4 mutants according to the present invention. Mutants 48, 44, 44P, 46, 45, 6, 29, 30, 28, 28P, 31, 8, 47 and 15 all show significantly higher Fab Tm values compared to the wild type IgG4 (mutant 17) and wild type IgG4 S241P (mutant 18).

Antibody Affinity:

The affinity of selected mutant IgG4 antibodies of the present invention to the target soluble cytokine was measured by Biacore™. The assay format was capture of the IgG's on an anti-Fc surface followed by titration of soluble cytokine.

The results are shown in FIG. 16, where it can be see that the mutant antibodies showed comparable affinity towards the soluble cytokine compared to the control IgG1 and IgG4 wild-type antibodies.

The term "$k_d$" ($s^{-1}$), refers to the dissociation rate constant of the antibody-antigen interaction. Said value is also referred to as the $k_{off}$ value.

The term "$k_a$" ($M^{-1}\ s^{-1}$), as used herein, refers to the association rate constant of the antibody-antigen interaction.

The term "$K_D$" (M) or "$K_D$" (pM), as used herein, refers to the dissociation equilibrium constant of the antibody-antigen interaction.

Size Exclusion (SEC) HPLC Analysis:

Approximately 50 ug purified antibody was run on the HPLC using a 5200 column. Abs 1 to 19 were used for the analysis. This result shows that non-covalently associated H2L2 is formed despite alterations to the DSB arrangements of a human IgG4 molecule.

The results of the HPLC analysis are shown in FIG. 17.

Alternative Upper Hinge Spacer Lengths

Poly-alanine spacers of between 1 and 5 amino acids in length were inserted between PP and CPSP, i.e. at the location indicated by '^', ESKYCPP^CPSPA (SEQ ID NO: 72). FIG. 18 shows that inserton of any length of spacer is sufficient to reduce the amount of H2 or L2 formation in mutant 15. However, insertion lengths of 3 or more amino acids appeared to offer the largest increase in thermostability. It is of note that a 3 amino acid insertion most closely mimics the difference in upper hinge length between IgG1 and IgG4.

Alternative Upper Hinge Spacer Amino Acid Composition

In order to explore whether tri-alanine insertions at ESKYCPP^CPSPA (SEQ ID NO: 72) had special properties as upper hinge spacers, two other tri-amino acids insertions were tested: GGG and THT. FIG. 19 shows that both GGG and THT were functional as spacer regions although results suggested that they were not identical. GGG appeared to be less capable than AAA or THT of reducing H2 and L2 formation. The increase in thermostability for GGG and THT was not as great as that observed with AAA.

Alternative Upper Hinge Spacer Amino Acid Length and Composition

IgG4 has a 2 amino acid (PP) 'spacer' between the CH1 interchain cysteine and the first core hinge cysteine, whilst IgG1 has a 5 amino acid DKTHT (SEQ ID NO: 73) spacer. Four mutants (68, 67. 66 and 56) were constructed to enable a comparison against mutant 15 (ESKYCPPCPSCP (SEQ ID NO: 74)). First the PP spacer of IgG4 was replaced with an equal length DK spacer as found in IgG1; mutant 68 (ESKYCDKCPSCP (SEQ ID NO: 75)) and then by one amino acid increments to mimic the IgG1 upper hinge spacer:

```
mutant 67 (ESKYCDKTCPSCP (SEQ ID NO: 76))

mutant 66 (ESKYCDKTHCPSCP (SEQ ID NO: 77))

mutant 56 (ESKYCDKTHTCPSCP (SEQ ID NO: 78)).
```

Data in FIG. 21 suggest that the single most important change is from PP to DK, which resulted in a reduction in H2, H and L formation relative to mutant 15. Increasing lengths of additional IgG1 like spacer insertion (T, TH and THT) appeared to effect minimal incremental reduction in H2 but may have resulted in an additional incremental increase in HL formation. Since mutants 68, 67, 66, and 56 contain a CPSC (SEQ ID NO: 79) core hinge sequence the increase in HL formation may be evidence for the spacers being more effective in isolating the LC-HC interchain disulphide bond cysteines away from the core hinge cysteines which are hence prone to formation of intra-molecular disulphide bonds.

Figure 22:
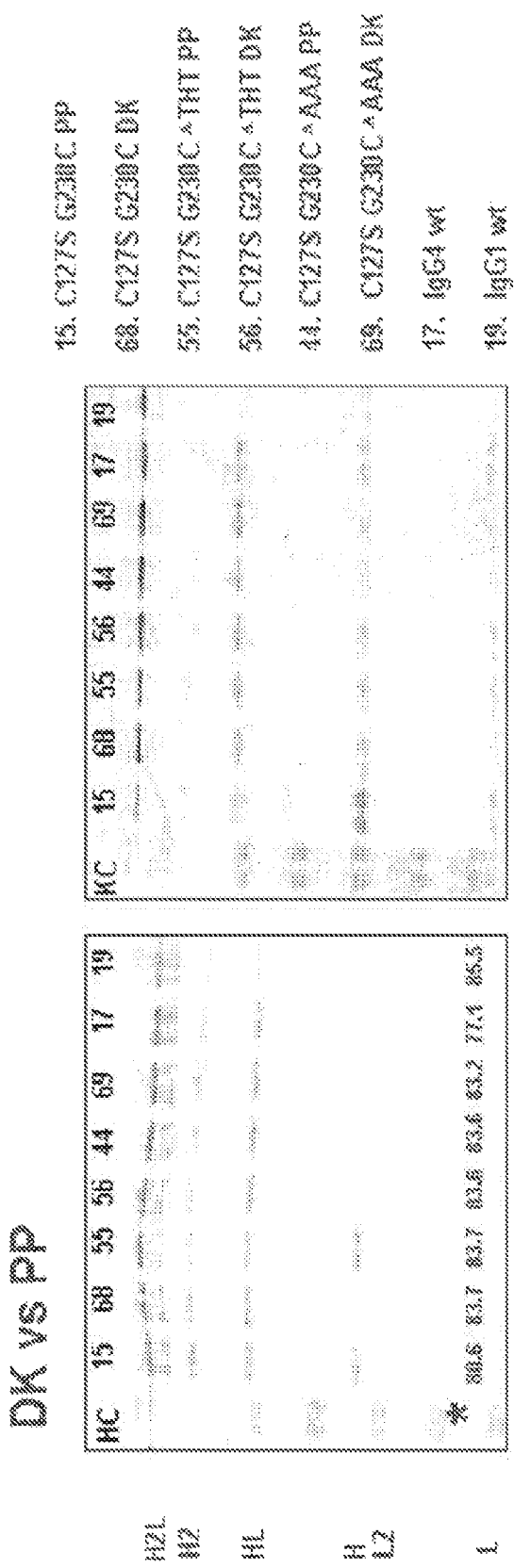

The data in FIG. 22 suggest that DK is preferable to PP as a choice of 2 amino acid spacer in terms of reducing disulphide isoform heterogeneity, compare mutants 15 (ESKYCPPCPSCP (SEQ ID NO: 74)) and 68 (ESKYCDKCPSCP (SEQ ID NO: 75)) and mutants 55 (ESKYCPPTHTCPSCP (SEQ ID NO: 80)) and 56 (ESKYCDKTHTCPSCP (SEQ ID NO: 78)). Short poly-proline motifs such as PP are known to be able to encode for some level of helix turn potential which may result in a local juxtaposition of LC-HC and core hinge cysteines. This local effect appears to be better overcome by an additional AAA as seen in mutant 44

(ESKYCPPAAACPSCP (SEQ ID NO: 81)). None of mutants 68, 55, 56, 44 or 69 appeared to have significantly different thermostabilities.

Influence of Non-Spacer Upper Hinge Sequence Composition

Figure 23:
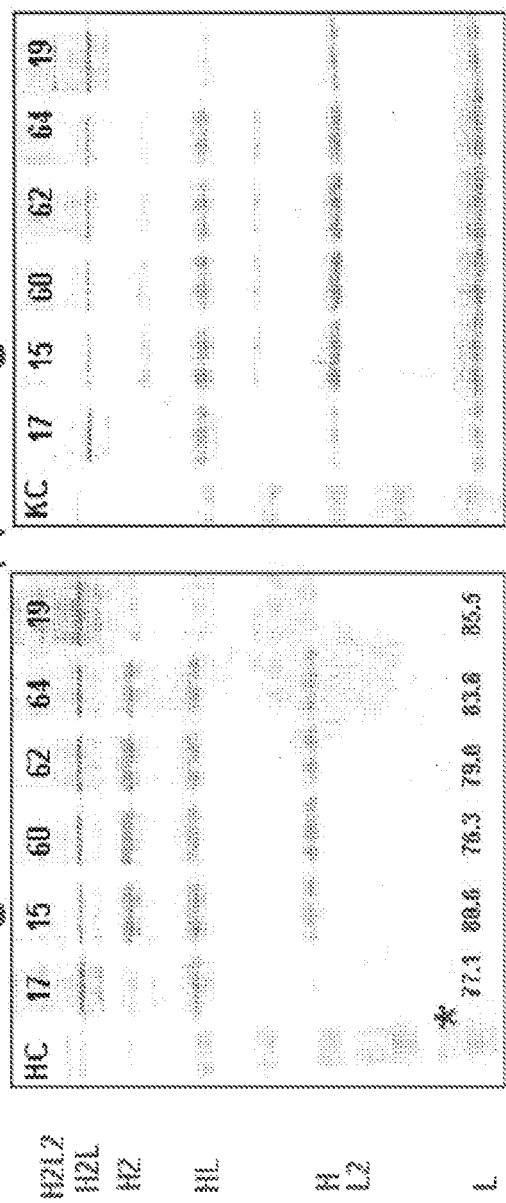

In order to understand the influence of the sequence composition of the upper hinge sequence N-terminal of the inter LC-HC CH1 cysteine (ESKY (SEQ ID NO: 82) in IgG4 and EPKS (SEQ ID NO: 83) in IgG1) all permutations of mutant were made in the context of mutant 15 (ESKYCPPCPSCP (SEQ ID NO: 74)). The data in FIG. 23 shows that in the context of a PP spacer, none of the permutations of upper hinge composition appeared to significantly affect disulphide isoform heterogeneity. Data shown above suggest that this lack of effect is primarily because the proteins contain a short PP spacer and a core hinge motif capable of intra-molecular disulphide bond formation. However, significant differences in thermostability were observed. Both of the naturally evolved sequences; ESKP (SEQ ID NO: 84) (83.8° C.) and EPKS (SEQ ID NO: 83) (80.6° C.) were more stable than either of the hybrid sequences; EPKY (SEQ ID NO: 85) (76.3° C.) and EPKS (SEQ ID NO: 83) (79.0° C.). The data show that the IgG1 EPKS (SEQ ID NO: 83) sequence is most preferable.

Figure 24:
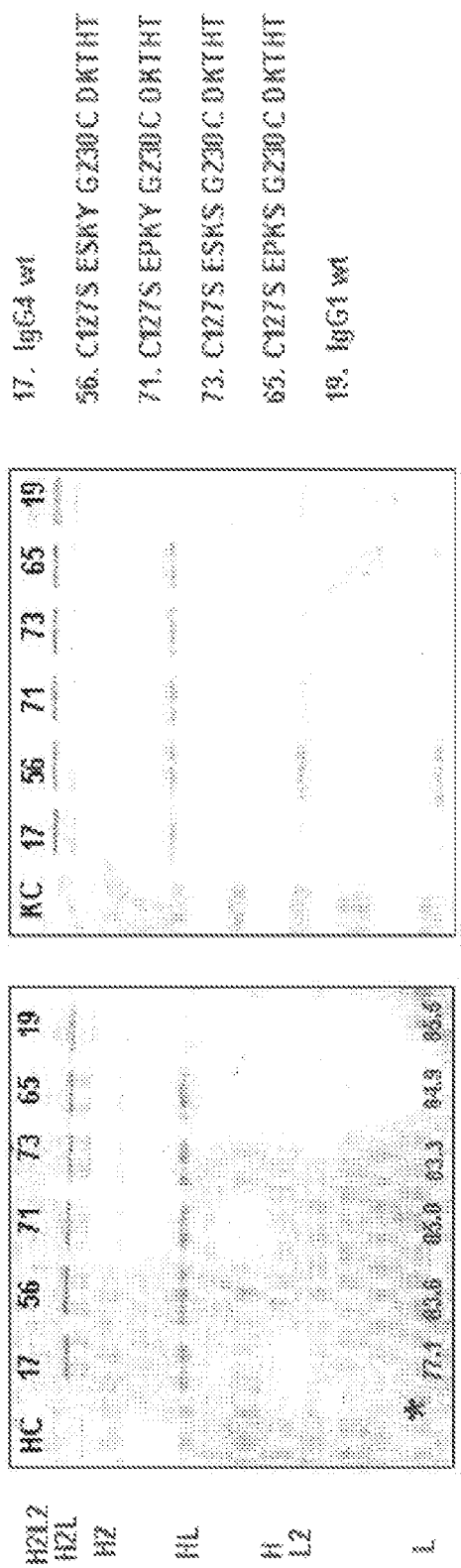

In order to understand the importance of the ESKY (SEQ ID NO: 82) or EPKS (SEQ ID NO: 83) upper hinge motifs in the context of the more preferable DKTHT (SEQ ID NO: 73) spacer region all permutations were made. The data in FIG. 24 show that the natural IgG4 ESKY (SEQ ID NO: 82) motif (mutant 56 ESKYCDKTHTCPSCP (SEQ ID NO: 78)) is the most susceptible to disulphide isoform heterogeneity. Data in FIG. 24 confirm that the natural IgG1 upper hinge sequence (mutant 65 (EPKSCDKTHTCPSCP (SEQ ID NO: 86)) has minimal potential for disulphide isoform heterogeneity and has a high thermostability.

Influence of the Core Hinge Ser to Pro Swap

A most preferred mutant 48 (EPKSCDKTHTCPPCP (SEQ ID NO: 87)) was mutated in order to re-introduce the natural IgG4 core hinge Ser (Ser$^{241}$ by Kabat numbering), resulting in mutant 65 (EPKSCDKTHTCPSCP (SEQ ID NO: 86)). The data in FIG. 20 confirm that mutant 48 has very significantly reduced levels of H2, HL, H and L compare to mutant 15 (ESKYCPPCPSCP (SEQ ID NO: 74)) and a very significantly increased thermostability. Re-introduction of the core hinge Ser$^{241}$ (mutant 65) did not affect the thermostability relative to mutant 48, but did result in reappearence of significant levels of HL. It is of note that mutant 65 still had less H2, H and L than mutant 15 illustrating the importance of upper hinge sequence length and composition with regards to disulphide isoform homogeneity.

Antibody Effector Function Assay by Cell Lysis

Target cells expressing cell surface antigen had their intracellular contents labelled by incubation with the fluorescence enhancing ligand BADTA. BADTA is converted within the cell to a hydrophillic ligand, TDA. Labelled cells are incubated with antibody and PBMC's (peripheral blood mononuclear cells) as lytic agents. Upon lysis of cells, in this example by ADCC, TDA is released and forms a fluorescent and stable chelate EuTDA when Europium is added to cell cultures. In essence, BADTA labelling of cellular contents enables a quantitation of cell lysis. Cell lysis in turn provides as measure of the presence of effector functions in an IgG. FIGS. 25 and 26 attempts to lyse cells with IgG4 by ADCC. An analogue of the Herceptin antibody (trastuzumab) was made as both IgG1 wild type and IgG4 wild type. The Her-2 antigen for Herceptin is expressed on MCF7 and SKBR3 cells. Mutants of the IgG Herceptin analogue were also generated. and IgG purified for use in the ADCC assay. IgG4 are known to have a very low ability to perform ADCC as confirmed by the difference between the control IgG1 wild type (wt) and IgG4 wild type (wt). This lack of innate ADCC potential was not affected by any one of the 4 IgG4 mutants tested. Notably these include mutants 28, 44 and 48 which have altered interchain LC-HC disulphide bond arrangements and most notably mutant 48 (EPKSCDKTHTCPPCP) which contains the IgG1 upper and core hinge motifs. Hence these data show that mutants described do not gain effector functions through use of IgG1 upper and core hinge sequences.

Broad Applicability of Mutants to IgG4 Antibodies.

All data described so far is for a particular UCB proprietory IgG4 antibody, Ab 410. In order to demonstrate that the improvements in disulphide isoform homogeneity and thermostability were not unique to the variable region encoded structure/stability of this IgG, exemplars of other IgG4 were generated. Publically available sequence information was used to create IgG4 analogues of three industrially relevent IgG's: Trastuzumab (Herceptin), Natalizumab (Tysabri) and Tocilizumab (Actemra). Collectively, the data shown in FIGS. 28 to 33 show that the relative performance of key mutants of IgG4 are highly similar on all IgG4 exemplars, both in terms disulphide isoform homogeneity and relative thermostability. The absolute stabilities of each exemplar differ from each other in a way expected from previous published observations on the differing inherent stabilities of IgG's. These data suggest that the mutants described are capable of improving disulphide isoform homogeneity and increasing thermostability in all IgG4 molecules.

Effect of IgG4 Mutants on Practical Considerations: Expression and Host Cell

Figure 31:
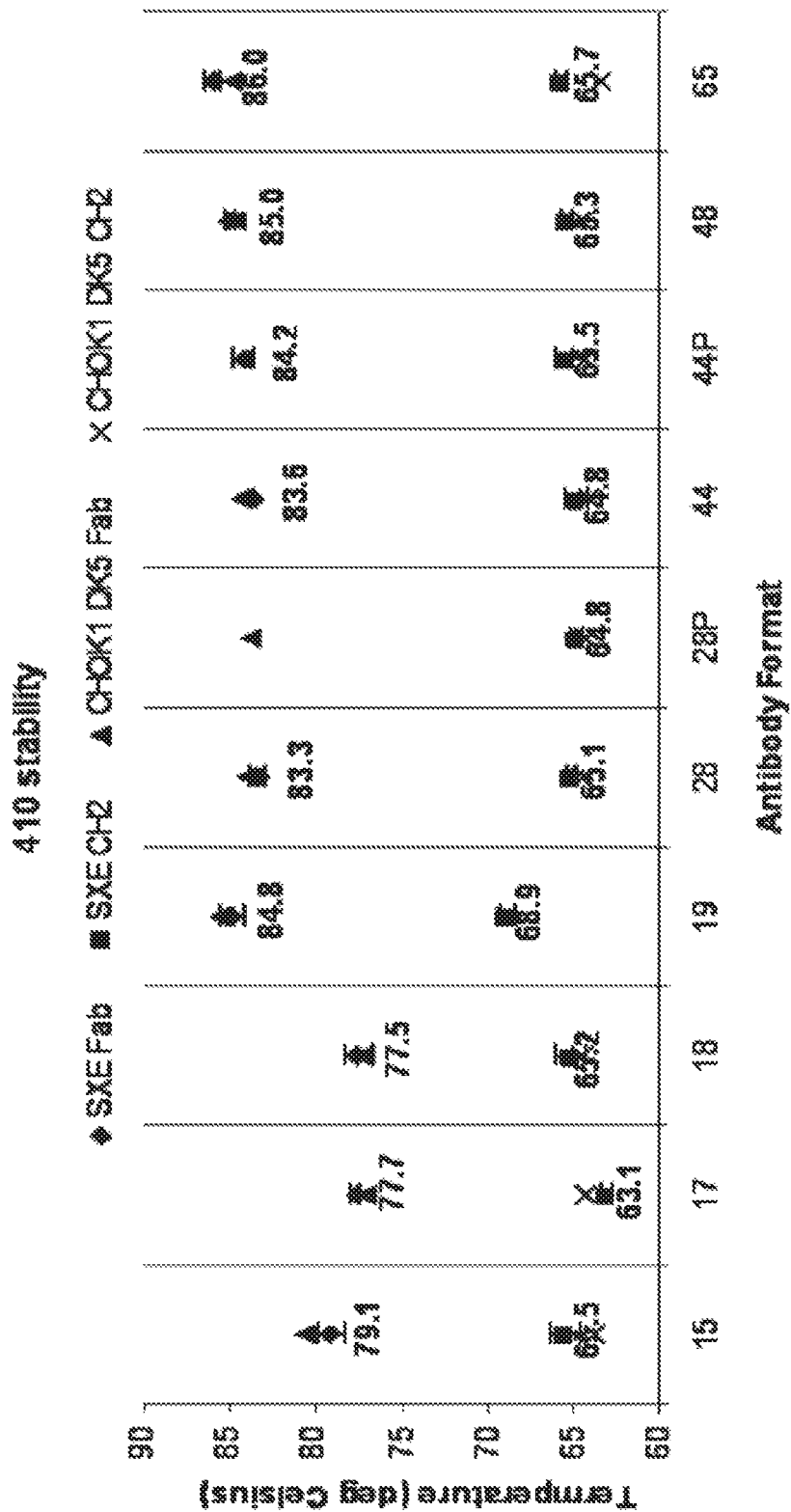
Figure 32:
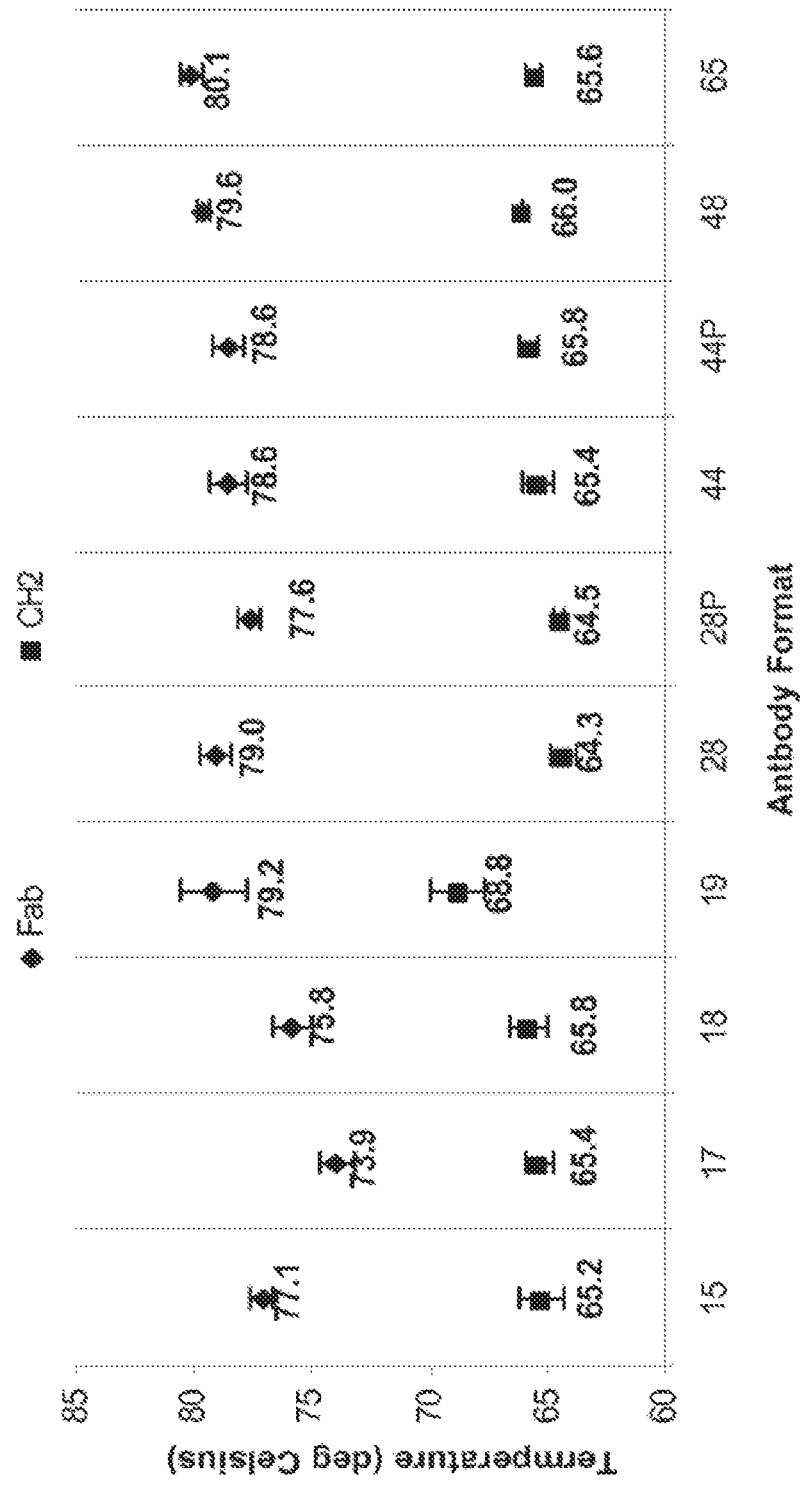
Figure 33:
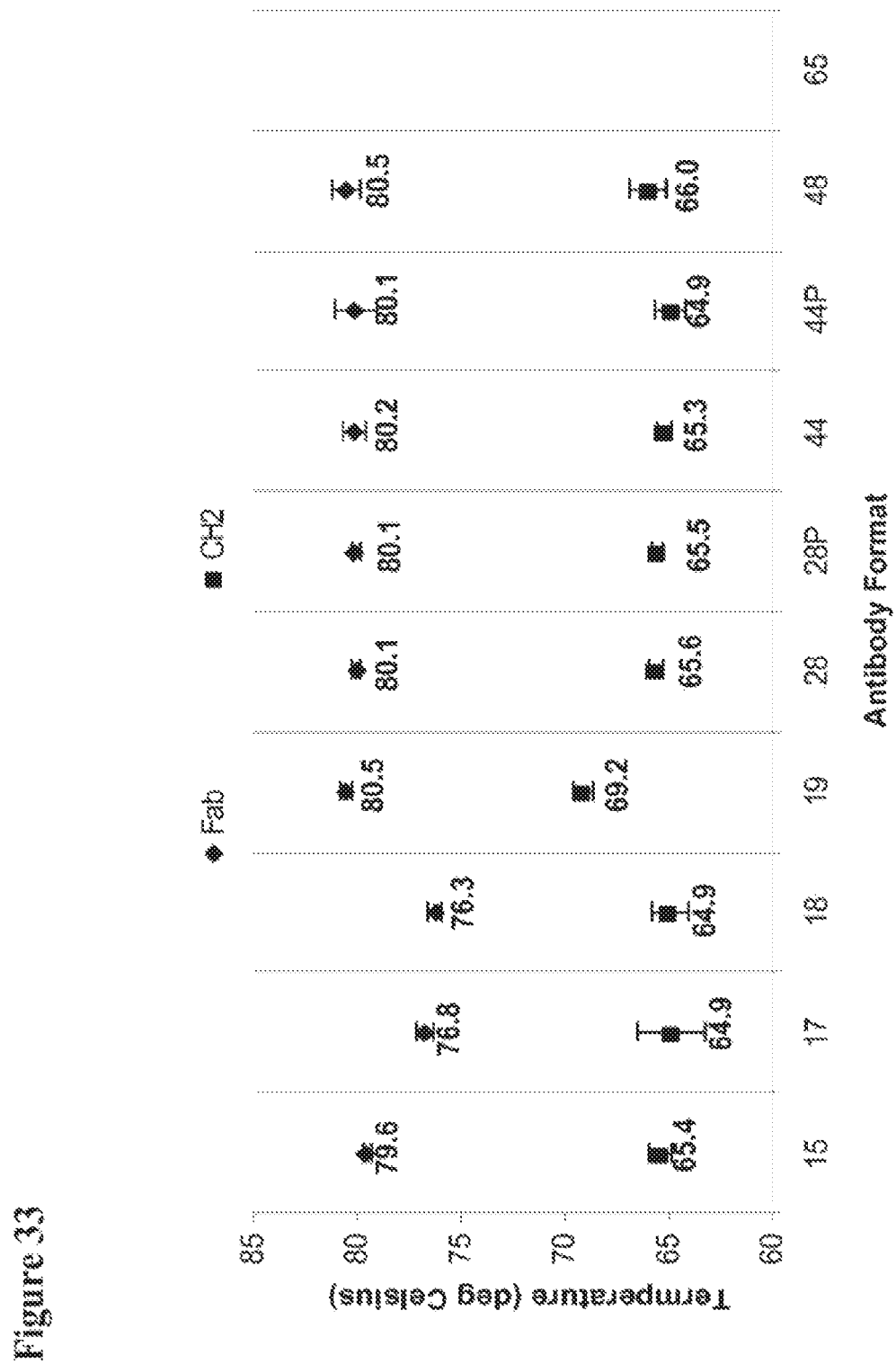
Figure 34:
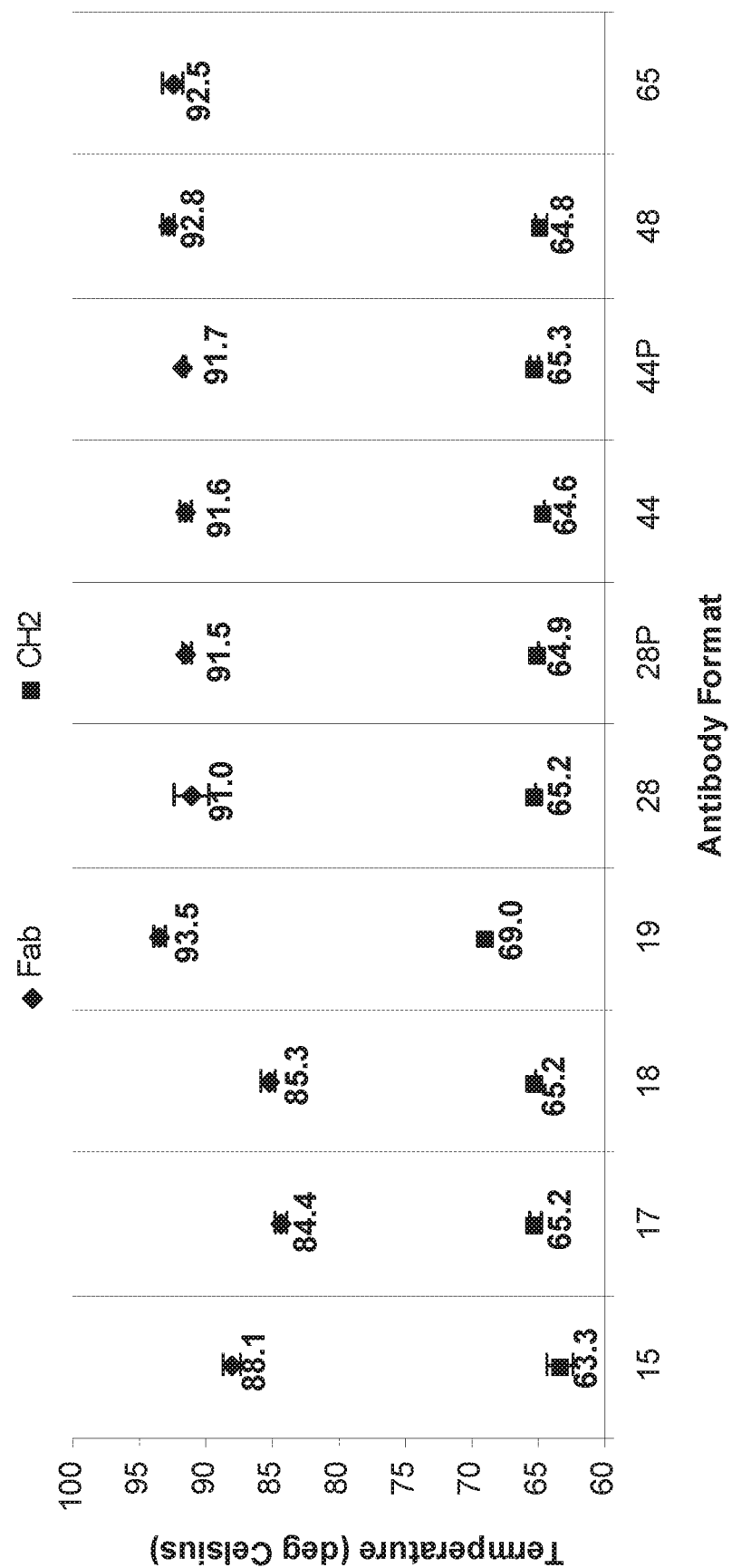

Mutants described have improved the disulphide isoform homogeneity and increased the thermostability in range of IgG4 molecules. Data in FIG. 27 show that these mutants do not negatively impact on IgG4 expression. Expression data shown is the mean expression for each mutant transiently expressed from CHO cells for each of the 4 antigen specificities described; Ab410, and analogues of Trastuzumab, Natalizumab and Tocilizumab. These data suggest that Fab arm interchain disulphide architecture and upper and core hinge sequences are not primary determinants of yield from CHO cells. The data in FIG. 31 show that the thermostability of Ab410 is the same whether the mutants are expressed in CHO-K1 or CHO-SXE cells. These data support that the mutations to the IgG Fab arm interchain disulphide architecture and upper and core hinge sequences are the primary determinants of improved thermostability.

The invention claimed is:

1. An antibody of the class IgG4, comprising two light chains and two heavy chains, wherein the heavy chains comprise a $C_H1$ domain and a hinge region comprising an IgG4 upper hinge and core region, wherein in each heavy chain:
   (a) the inter-chain cysteine at position 127 in the $C_H1$ domain is substituted with an amino acid selected from the group comprising serine, threonine, alanine, and glycine; and
   (b) one or more of the amino acids at positions 227, 228, and 229 in the upper hinge region is substituted with cysteine,
and wherein the amino acid numbering is according to the Kabat numbering system.

2. The antibody of claim 1, wherein the amino acid at position 229 is cysteine.

3. The antibody of claim 1, wherein the amino acid at position 228 is cysteine.

4. The antibody of claim 1, wherein the amino acid at position 227 is cysteine.

5. The antibody of claim 1, wherein at least one of the amino acids at position 239 and position 242, numbered according to the Kabat numbering system, in each of the heavy chains is a serine.

6. The antibody of claim 1, wherein the amino acid at position 239, numbered according to the Kabat numbering system, in each of the heavy chains is serine.

7. The antibody of claim 1, wherein the amino acid at position 242, numbered according to the Kabat numbering system, in each of the heavy chains is serine.

8. The antibody of claim 7, wherein the amino acid at position 239 and/or the amino acid at position 242 is a serine.

9. The antibody of claim 1, wherein the heavy chains are mutated to insert three amino acids between amino acids 226-243, numbered according to the Kabat numbering system.

10. The antibody of claim 9, wherein the heavy chains are mutated to insert three amino acids between positions 238 and 239, numbered according to the Kabat numbering system.

11. The antibody of claim 10, wherein three alanines are inserted between positions 238 and 239, numbered according to the Kabat numbering system.

12. The antibody of claim 10, wherein a threonine, a histidine and a further threonine are inserted between positions 238 and 239, numbered according to the Kabat numbering system.

13. The antibody of claim 10, wherein the serine at position 241, numbered according to the Kabat numbering system, is substituted with proline.

14. The antibody of claim 1, wherein each heavy chain comprises a CH2 domain and a CH3 domain.

15. The antibody of claim 1, wherein the heavy chains are identical.

16. The antibody of claim 1, wherein the upper hinge and core region is of 15 amino acids in length.

17. The antibody of claim 1, wherein the upper hinge and core region is 13-17 amino acids in length.

18. The antibody of claim 1, wherein the inter-chain cysteine at position 127 is substituted with a threonine or serine.

19. The antibody of claim 1, wherein the inter-chain cysteine at position 127 is substituted with a serine.

* * * * *

SEQUENCE LISTING

<160> NUMBER OF SEQ ID NOS: 87

<210> SEQ ID NO 1

```
<211> LENGTH: 120
<212> TYPE: PRT
<213> ORGANISM: Artificial
<220> FEATURE:
<223> OTHER INFORMATION: Hinge
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 1

Xaa Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Xaa Pro Lys Ser Cys Asp Lys Thr His Thr Cys Pro Pro Cys
            100                 105                 110

Pro Ala Pro Glu Leu Gly Gly Pro
            115                 120

<210> SEQ ID NO 2
<211> LENGTH: 118
<212> TYPE: PRT
<213> ORGANISM: Artificial
<220> FEATURE:
<223> OTHER INFORMATION: Hinge
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 2

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Cys Pro Ser Cys Pro Ala Pro
            100                 105                 110
```

```
Glu Phe Leu Gly Gly Pro
        115

<210> SEQ ID NO 3
<211> LENGTH: 6
<212> TYPE: PRT
<213> ORGANISM: Artificial
<220> FEATURE:
<223> OTHER INFORMATION: Light Chain

<400> SEQUENCE: 3

Phe Asn Arg Gly Glu Cys
1               5

<210> SEQ ID NO 4
<211> LENGTH: 9
<212> TYPE: PRT
<213> ORGANISM: Artificial
<220> FEATURE:
<223> OTHER INFORMATION: Heavy Chain IgG1

<400> SEQUENCE: 4

Leu Ala Pro Ser Ser Lys Ser Thr Ser
1               5

<210> SEQ ID NO 5
<211> LENGTH: 23
<212> TYPE: PRT
<213> ORGANISM: Artificial
<220> FEATURE:
<223> OTHER INFORMATION: Heavy Chain IgG1
<220> FEATURE:
<221> NAME/KEY: misc_feature
<222> LOCATION: (10)..(11)
<223> OTHER INFORMATION: discontinuous sequence
<220> FEATURE:
<221> NAME/KEY: misc_feature
<222> LOCATION: (15)..(16)
<223> OTHER INFORMATION: discontinuous sequence

<400> SEQUENCE: 5

Glu Pro Lys Ser Cys Asp Lys Thr His Thr Cys Pro Pro Cys Pro
1               5                   10                  15

Ala Pro Glu Leu Leu Gly Gly Pro
            20

<210> SEQ ID NO 6
<211> LENGTH: 9
<212> TYPE: PRT
<213> ORGANISM: Artificial
<220> FEATURE:
<223> OTHER INFORMATION: Heavy Chain IgG2

<400> SEQUENCE: 6

Leu Ala Pro Cys Ser Arg Ser Thr Ser
1               5

<210> SEQ ID NO 7
<211> LENGTH: 19
<212> TYPE: PRT
<213> ORGANISM: Artificial
<220> FEATURE:
<223> OTHER INFORMATION: Heavy Chain IgG2
<220> FEATURE:
<221> NAME/KEY: misc_feature
<222> LOCATION: (3)..(4)
<223> OTHER INFORMATION: discontinuous sequence
<220> FEATURE:
<221> NAME/KEY: misc_feature
```

```
<222> LOCATION: (12)..(13)
<223> OTHER INFORMATION: discontinuous sequence

<400> SEQUENCE: 7

Glu Arg Lys Cys Cys Val Glu Cys Pro Pro Cys Pro Ala Pro
1               5                   10

Pro Val Ala Gly Pro
            15

<210> SEQ ID NO 8
<211> LENGTH: 9
<212> TYPE: PRT
<213> ORGANISM: Artificial
<220> FEATURE:
<223> OTHER INFORMATION: Heavy Chain IgG3

<400> SEQUENCE: 8

Leu Ala Pro Cys Ser Arg Ser Thr Ser
1               5

<210> SEQ ID NO 9
<211> LENGTH: 70
<212> TYPE: PRT
<213> ORGANISM: Artificial
<220> FEATURE:
<223> OTHER INFORMATION: Heavy Chain IgG3
<220> FEATURE:
<221> NAME/KEY: misc_feature
<222> LOCATION: (12)..(13)
<223> OTHER INFORMATION: discontinuous sequence
<220> FEATURE:
<221> NAME/KEY: misc_feature
<222> LOCATION: (62)..(63)
<223> OTHER INFORMATION: discontinuous sequence

<400> SEQUENCE: 9

Glu Leu Lys Thr Pro Leu Gly Asp Thr Thr His Thr Cys Pro Arg
1               5                   10                  15

Cys Pro Glu Pro Lys Ser Cys Asp Thr Pro Pro Pro Cys Pro Arg Cys
            20                  25                  30

Pro Glu Pro Lys Ser Cys Asp Thr Pro Pro Pro Cys Pro Arg Cys Pro
        35                  40                  45

Glu Pro Lys Ser Cys Asp Thr Pro Pro Pro Cys Pro Arg Cys Pro
    50                  55                  60

Ala Pro Glu Leu Leu Gly Gly Pro
65                  70

<210> SEQ ID NO 10
<211> LENGTH: 9
<212> TYPE: PRT
<213> ORGANISM: Artificial
<220> FEATURE:
<223> OTHER INFORMATION: Heavh Chain IgG4

<400> SEQUENCE: 10

Leu Ala Pro Cys Ser Arg Ser Thr Ser
1               5

<210> SEQ ID NO 11
<211> LENGTH: 20
<212> TYPE: PRT
<213> ORGANISM: Artificial
<220> FEATURE:
<223> OTHER INFORMATION: Heavy Chain IgG4

<400> SEQUENCE: 11
```

-continued

Glu Ser Lys Tyr Gly Pro Pro Cys Pro Ser Cys Pro Ala Pro Glu
1               5                   10                  15

Phe Leu Gly Gly Pro
            20

<210> SEQ ID NO 12
<211> LENGTH: 118
<212> TYPE: PRT
<213> ORGANISM: Artificial
<220> FEATURE:
<223> OTHER INFORMATION: Antibody 6
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 12

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ser Pro Ser Cys Pro Ala Pro
            100                 105                 110

Glu Phe Leu Gly Gly Pro
            115

<210> SEQ ID NO 13
<211> LENGTH: 118
<212> TYPE: PRT
<213> ORGANISM: Artificial
<220> FEATURE:
<223> OTHER INFORMATION: Antibody 7
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 13

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Ser Ser Pro Ala Pro
            100                 105                 110

Glu Phe Leu Gly Gly Pro
            115

<210> SEQ ID NO 14
<211> LENGTH: 118
<212> TYPE: PRT
<213> ORGANISM: Artificial
<220> FEATURE:
<223> OTHER INFORMATION: Antibody 8
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 14

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Ser Ser Pro Ala Pro
            100                 105                 110

Glu Phe Leu Gly Gly Pro
            115

<210> SEQ ID NO 15
<211> LENGTH: 118
<212> TYPE: PRT
<213> ORGANISM: Artificial
<220> FEATURE:
<223> OTHER INFORMATION: Antibody 15
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 15

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Ser Cys Pro Ala Pro
                100                 105                 110

Glu Phe Leu Gly Gly Pro
        115

<210> SEQ ID NO 16
<211> LENGTH: 118
<212> TYPE: PRT
<213> ORGANISM: Artificial
<220> FEATURE:
<223> OTHER INFORMATION: Antibody 16
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or is glutamic acid

<400> SEQUENCE: 16

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Ser Cys Pro Ala Pro
                100                 105                 110

Glu Phe Leu Gly Gly Pro
        115

<210> SEQ ID NO 17
<211> LENGTH: 118
<212> TYPE: PRT
<213> ORGANISM: Artificial
<220> FEATURE:
<223> OTHER INFORMATION: Anitbody 28
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 17

Xaa Ser Thr Lys Gly Pro Ser Val Phe Pro Leu Ala Pro Ser Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Cys Pro Ser Cys Pro Ala Pro
            100                 105                 110

Glu Phe Leu Gly Gly Pro
        115
```

<210> SEQ ID NO 18
<211> LENGTH: 118
<212> TYPE: PRT
<213> ORGANISM: Artificial
<220> FEATURE:
<223> OTHER INFORMATION: Antibody 29
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 18

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Cys Pro Ser Cys Pro Ala Pro
            100                 105                 110

Glu Phe Leu Gly Gly Pro
        115
```

<210> SEQ ID NO 19
<211> LENGTH: 118
<212> TYPE: PRT
<213> ORGANISM: Artificial
<220> FEATURE:
<223> OTHER INFORMATION: Antibody 30
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 19

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Cys Pro Ser Ser Pro Ala Pro
            100                 105                 110

Glu Phe Leu Gly Gly Pro
        115

<210> SEQ ID NO 20
<211> LENGTH: 118
<212> TYPE: PRT
<213> ORGANISM: Artificial
<220> FEATURE:
<223> OTHER INFORMATION: Antibody 20
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 20

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Ser Pro Ser Ser Pro Ala Pro
            100                 105                 110

Glu Phe Leu Gly Gly Pro
        115

<210> SEQ ID NO 21
<211> LENGTH: 118
<212> TYPE: PRT
<213> ORGANISM: Artificial
<220> FEATURE:
<223> OTHER INFORMATION: Antibody 32
<220> FEATURE:
<221> NAME/KEY: misc_feature
<222> LOCATION: (1)..(1)

<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 21

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Cys Pro Ser Cys Pro Ala Pro
            100                 105                 110

Glu Phe Leu Gly Gly Pro
            115
```

<210> SEQ ID NO 22
<211> LENGTH: 118
<212> TYPE: PRT
<213> ORGANISM: Artificial
<220> FEATURE:
<223> OTHER INFORMATION: Antibody 33
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 22

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Cys Pro Ser Cys Pro Ala Pro
            100                 105                 110

Glu Phe Leu Gly Gly Pro
            115
```

<210> SEQ ID NO 23
<211> LENGTH: 118
<212> TYPE: PRT
<213> ORGANISM: Artificial

```
<220> FEATURE:
<223> OTHER INFORMATION: Antibody 34
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 23

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Cys Pro Ser Ser Pro Ala Pro
            100                 105                 110

Glu Phe Leu Gly Gly Pro
            115

<210> SEQ ID NO 24
<211> LENGTH: 118
<212> TYPE: PRT
<213> ORGANISM: Artificial
<220> FEATURE:
<223> OTHER INFORMATION: Antibody 35
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 24

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Ser Pro Ser Ser Pro Ala Pro
            100                 105                 110

Glu Phe Leu Gly Gly Pro
            115
```

```
<210> SEQ ID NO 25
<211> LENGTH: 118
<212> TYPE: PRT
<213> ORGANISM: Artificial
<220> FEATURE:
<223> OTHER INFORMATION: Antibody 36
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 25

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Cys Pro Ser Cys Pro Ala Pro
            100                 105                 110

Glu Phe Leu Gly Gly Pro
            115

<210> SEQ ID NO 26
<211> LENGTH: 118
<212> TYPE: PRT
<213> ORGANISM: Artificial
<220> FEATURE:
<223> OTHER INFORMATION: Antibody 37
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 26

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Ser Pro Ser Cys Pro Ala Pro
```

-continued

```
                100                 105                 110

Glu Phe Leu Gly Gly Pro
        115

<210> SEQ ID NO 27
<211> LENGTH: 118
<212> TYPE: PRT
<213> ORGANISM: Artificial
<220> FEATURE:
<223> OTHER INFORMATION: Antibody 38
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 27

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Cys Pro Ser Ser Pro Ala Pro
            100                 105                 110

Glu Phe Leu Gly Gly Pro
        115

<210> SEQ ID NO 28
<211> LENGTH: 118
<212> TYPE: PRT
<213> ORGANISM: Artificial
<220> FEATURE:
<223> OTHER INFORMATION: Antibody 39
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 28

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

```
Tyr Thr Cys Asn Val Asp His Lys Pro Ser Asn Thr Lys Val Asp Lys
                85                  90                  95

Arg Val Xaa Cys Lys Tyr Gly Pro Pro Ser Pro Ser Ser Pro Ala Pro
            100                 105                 110

Glu Phe Leu Gly Gly Pro
        115

<210> SEQ ID NO 29
<211> LENGTH: 121
<212> TYPE: PRT
<213> ORGANISM: Artificial
<220> FEATURE:
<223> OTHER INFORMATION: Antibody 44
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 29

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Cys Pro Ser Cys
            100                 105                 110

Pro Ala Pro Glu Phe Leu Gly Gly Pro
        115                 120

<210> SEQ ID NO 30
<211> LENGTH: 121
<212> TYPE: PRT
<213> ORGANISM: Artificial
<220> FEATURE:
<223> OTHER INFORMATION: Antibody 45
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 30

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Ser Pro Ser Cys
            100                 105                 110

Pro Ala Pro Glu Phe Leu Gly Gly Pro
            115                 120

<210> SEQ ID NO 31
<211> LENGTH: 121
<212> TYPE: PRT
<213> ORGANISM: Artificial
<220> FEATURE:
<223> OTHER INFORMATION: Antibody 46
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 31

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Cys Pro Ser Ser
            100                 105                 110

Pro Ala Pro Glu Phe Leu Gly Gly Pro
            115                 120

<210> SEQ ID NO 32
<211> LENGTH: 121
<212> TYPE: PRT
<213> ORGANISM: Artificial
<220> FEATURE:
<223> OTHER INFORMATION: Antibody 47
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 32

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
```

```
                  20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Ser Pro Ser Ser
                100                 105                 110

Pro Ala Pro Glu Phe Leu Gly Gly Pro
            115                 120

<210> SEQ ID NO 33
<211> LENGTH: 118
<212> TYPE: PRT
<213> ORGANISM: Artificial
<220> FEATURE:
<223> OTHER INFORMATION: Antibody 2
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 33

Xaa Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Ser Pro Ser Cys Pro Ala Pro
                100                 105                 110

Glu Phe Leu Gly Gly Pro
            115

<210> SEQ ID NO 34
<211> LENGTH: 118
<212> TYPE: PRT
<213> ORGANISM: Artificial
<220> FEATURE:
<223> OTHER INFORMATION: Antibody 3
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 34
```

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Cys Pro Ser Pro Ala Pro
            100                 105                 110

Glu Phe Leu Gly Gly Pro
            115

<210> SEQ ID NO 35
<211> LENGTH: 121
<212> TYPE: PRT
<213> ORGANISM: Artificial
<220> FEATURE:
<223> OTHER INFORMATION: Antibody 48
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 35

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Pro Lys Ser Cys Asp Lys Thr His Thr Cys Pro Pro Cys
            100                 105                 110

Pro Ala Pro Glu Phe Leu Gly Gly Pro
        115                 120

<210> SEQ ID NO 36
<211> LENGTH: 118
<212> TYPE: PRT
<213> ORGANISM: Artificial
<220> FEATURE:
<223> OTHER INFORMATION: Antibody 28P
<220> FEATURE:
<221> NAME/KEY: misc_feature
<222> LOCATION: (1)..(1)
<223> OTHER INFORMATION: Xaa is absent or alanine
<220> FEATURE:

-continued

```
<221> NAME/KEY: misc_feature
<222> LOCATION: (99)..(99)
<223> OTHER INFORMATION: Xaa is absent or glutamic acid

<400> SEQUENCE: 36

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Cys Pro Pro Cys Pro Ala Pro
            100                 105                 110

Glu Phe Leu Gly Gly Pro
            115

<210> SEQ ID NO 37
<211> LENGTH: 121
<212> TYPE: PRT
<213> ORGANISM: Artificial
<220> FEATURE:
<223> OTHER INFORMATION: Antibody 44P
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 37

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Cys Pro Pro Cys
            100                 105                 110

Pro Ala Pro Glu Phe Leu Gly Gly Pro
            115                 120

<210> SEQ ID NO 38
<211> LENGTH: 327
<212> TYPE: PRT
<213> ORGANISM: Artificial
<220> FEATURE:
<223> OTHER INFORMATION: Antibody 6
```

```
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 38
```

| | | | | | | | | | | | | | | | |
|---|---|---|---|---|---|---|---|---|---|---|---|---|---|---|---|
| Xaa | Ser | Thr | Lys | Gly | Pro | Ser | Val | Phe | Pro | Leu | Ala | Pro | Ser | Ser | Arg |
| 1 | | | | 5 | | | | | 10 | | | | | 15 | |
| Ser | Thr | Ser | Glu | Ser | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | | 40 | | | | | 45 | | |
| Gly | Val | His | Thr | Phe | Pro | Ala | Val | Leu | Gln | Ser | Ser | Gly | Leu | Tyr | Ser |
| | | 50 | | | | | 55 | | | | | 60 | | | |
| Leu | Ser | Ser | Val | Val | Thr | Val | Pro | Ser | Ser | Ser | Leu | Gly | Thr | Lys | Thr |
| 65 | | | | | 70 | | | | | 75 | | | | | 80 |
| Tyr | Thr | Cys | Asn | Val | Asp | His | Lys | Pro | Ser | Asn | Thr | Lys | Val | Asp | Lys |
| | | | | 85 | | | | | 90 | | | | | 95 | |
| Arg | Val | Xaa | Ser | Lys | Tyr | Cys | Pro | Pro | Ser | Pro | Ser | Cys | Pro | Ala | Pro |
| | | | 100 | | | | | 105 | | | | | 110 | | |
| Glu | Phe | Leu | Gly | Gly | Pro | Ser | Val | Phe | Leu | Phe | Pro | Pro | Lys | Pro | Lys |
| | | | 115 | | | | | 120 | | | | | 125 | | |
| Asp | Thr | Leu | Met | Ile | Ser | Arg | Thr | Pro | Glu | Val | Thr | Cys | Val | Val | Val |
| | | 130 | | | | | 135 | | | | | 140 | | | |
| Asp | Val | Ser | Gln | Glu | Asp | Pro | Glu | Val | Gln | Phe | Asn | Trp | Tyr | Val | Asp |
| 145 | | | | | 150 | | | | | 155 | | | | | 160 |
| Gly | Val | Glu | Val | His | Asn | Ala | Lys | Thr | Lys | Pro | Arg | Glu | Glu | Gln | Phe |
| | | | | 165 | | | | | 170 | | | | | 175 | |
| Asn | Ser | Thr | Tyr | Arg | Val | Val | Ser | Val | Leu | Thr | Val | Leu | His | Gln | Asp |
| | | | 180 | | | | | 185 | | | | | 190 | | |
| Trp | Leu | Asn | Gly | Lys | Glu | Tyr | Lys | Cys | Lys | Val | Ser | Asn | Lys | Gly | Leu |
| | | | 195 | | | | | 200 | | | | | 205 | | |
| Pro | Ser | Ser | Ile | Glu | Lys | Thr | Ile | Ser | Lys | Ala | Lys | Gly | Gln | Pro | Arg |
| | | 210 | | | | | 215 | | | | | 220 | | | |
| Glu | Pro | Gln | Val | Tyr | Thr | Leu | Pro | Pro | Ser | Gln | Glu | Glu | Met | Thr | Lys |
| 225 | | | | | 230 | | | | | 235 | | | | | 240 |
| Asn | Gln | Val | Ser | Leu | Thr | Cys | Leu | Val | Lys | Gly | Phe | Tyr | Pro | Ser | Asp |
| | | | | 245 | | | | | 250 | | | | | 255 | |
| Ile | Ala | Val | Glu | Trp | Glu | Ser | Asn | Gly | Gln | Pro | Glu | Asn | Asn | Tyr | Lys |
| | | | 260 | | | | | 265 | | | | | 270 | | |
| Thr | Thr | Pro | Pro | Val | Leu | Asp | Ser | Asp | Gly | Ser | Phe | Phe | Leu | Tyr | Ser |
| | | | 275 | | | | | 280 | | | | | 285 | | |
| Arg | Leu | Thr | Val | Asp | Lys | Ser | Arg | Trp | Gln | Glu | Gly | Asn | Val | Phe | Ser |
| | | 290 | | | | | 295 | | | | | 300 | | | |
| Cys | Ser | Val | Met | His | Glu | Ala | Leu | His | Asn | His | Tyr | Thr | Gln | Lys | Ser |
| 305 | | | | | 310 | | | | | 315 | | | | | 320 |
| Leu | Ser | Leu | Ser | Leu | Gly | Lys | | | | | | | | | |
| | | | | 325 | | | | | | | | | | | |

```
<210> SEQ ID NO 39
<211> LENGTH: 327
<212> TYPE: PRT
<213> ORGANISM: Artificial
```

```
<220> FEATURE:
<223> OTHER INFORMATION: Antibody 7
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 39

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Ser Ser Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 40
<211> LENGTH: 327
```

```
<212> TYPE: PRT
<213> ORGANISM: Artificial
<220> FEATURE:
<223> OTHER INFORMATION: Antibody 8
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 40

Xaa Ser Thr Lys Gly Pro Ser Val Phe Pro Leu Ala Pro Ser Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Xaa Ser Lys Tyr Cys Pro Pro Ser Pro Ser Ser Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 41
<211> LENGTH: 327
<212> TYPE: PRT
<213> ORGANISM: Artificial
<220> FEATURE:
<223> OTHER INFORMATION: Antibody 15
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 41

Xaa Ser Thr Lys Gly Pro Ser Val Phe Pro Leu Ala Pro Ser Ser Arg
 1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 42
<211> LENGTH: 327
<212> TYPE: PRT
<213> ORGANISM: Artificial
<220> FEATURE:
<223> OTHER INFORMATION: Antibody 16
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 42

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

-continued

```
Leu Ser Leu Ser Leu Gly Lys
            325

<210> SEQ ID NO 43
<211> LENGTH: 327
<212> TYPE: PRT
<213> ORGANISM: Artificial
<220> FEATURE:
<223> OTHER INFORMATION: Antibody 28
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 43

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
```

```
                305                 310                 315                 320
Leu Ser Leu Ser Leu Gly Lys
                325

<210> SEQ ID NO 44
<211> LENGTH: 327
<212> TYPE: PRT
<213> ORGANISM: Artificial
<220> FEATURE:
<223> OTHER INFORMATION: Antibody 29
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 44

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Ser Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 45
<211> LENGTH: 327
<212> TYPE: PRT
<213> ORGANISM: Artificial
<220> FEATURE:
<223> OTHER INFORMATION: Antibody 30
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 45

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Cys Pro Ser Ser Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 46
<211> LENGTH: 327
<212> TYPE: PRT
<213> ORGANISM: Artificial
<220> FEATURE:
<223> OTHER INFORMATION: Antbody 31
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 46

Xaa Ser Thr Lys Gly Pro Ser Val Phe Pro Leu Ala Pro Ser Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Xaa Ser Lys Cys Gly Pro Pro Ser Pro Ser Pro Ala Pro
            100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
```

```
                275                 280                 285
Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 47
<211> LENGTH: 327
<212> TYPE: PRT
<213> ORGANISM: Artificial
<220> FEATURE:
<223> OTHER INFORMATION: Antibody 32
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 47

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 48
<211> LENGTH: 327
<212> TYPE: PRT
<213> ORGANISM: Artificial
<220> FEATURE:
<223> OTHER INFORMATION: Antibody 33
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 48

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Ser Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 49
<211> LENGTH: 327
<212> TYPE: PRT
<213> ORGANISM: Artificial
<220> FEATURE:
<223> OTHER INFORMATION: Antibody 34
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 49

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Cys Pro Ser Ser Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
```

```
                            245                 250                 255
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 50
<211> LENGTH: 327
<212> TYPE: PRT
<213> ORGANISM: Artificial
<220> FEATURE:
<223> OTHER INFORMATION: Anitbody 35
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 50

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Ser Pro Ser Ser Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 51
<211> LENGTH: 327
<212> TYPE: PRT
<213> ORGANISM: Artificial
<220> FEATURE:
<223> OTHER INFORMATION: Antibody 36
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 51

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 52
<211> LENGTH: 327
<212> TYPE: PRT
<213> ORGANISM: Artificial
<220> FEATURE:
<223> OTHER INFORMATION: Antibody 37
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 52

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Ser Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
              210                 215                 220
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 53
<211> LENGTH: 327
<212> TYPE: PRT
<213> ORGANISM: Artificial
<220> FEATURE:
<223> OTHER INFORMATION: Antobody 38
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 53

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Cys Pro Ser Ser Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 54
<211> LENGTH: 327
<212> TYPE: PRT
<213> ORGANISM: Artificial
<220> FEATURE:
<223> OTHER INFORMATION: Antibody 39
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 54

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Ser Pro Ser Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 55
<211> LENGTH: 330
<212> TYPE: PRT
<213> ORGANISM: Artificial
<220> FEATURE:
<223> OTHER INFORMATION: Antibody 44
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 55

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Cys Pro Ser Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
```

```
                    180                 185                 190
His Gln Asp Trp Leu Asn Gly Lys Glu Tyr Lys Cys Lys Val Ser Asn
                195                 200                 205

Lys Gly Leu Pro Ser Ser Ile Glu Lys Thr Ile Ser Lys Ala Lys Gly
            210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
                275                 280                 285

Leu Tyr Ser Arg Leu Thr Val Asp Lys Ser Arg Trp Gln Glu Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 56
<211> LENGTH: 330
<212> TYPE: PRT
<213> ORGANISM: Artificial
<220> FEATURE:
<223> OTHER INFORMATION: Antibody 45
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 56

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Ser Pro Ser Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175
```

```
Glu Gln Phe Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Gly Leu Pro Ser Ser Ile Glu Lys Thr Ile Ser Lys Ala Lys Gly
        210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Glu Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 57
<211> LENGTH: 330
<212> TYPE: PRT
<213> ORGANISM: Artificial
<220> FEATURE:
<223> OTHER INFORMATION: Antibody 46
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 57

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Cys Pro Ser Ser
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Gln Glu Asp Pro Glu Val Gln Phe Asn Trp
145                 150                 155                 160
```

```
Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Glu Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 58
<211> LENGTH: 330
<212> TYPE: PRT
<213> ORGANISM: Artificial
<220> FEATURE:
<223> OTHER INFORMATION: Antibody 47
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 58

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Ser Pro Ser Ser
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Gln Glu Asp Pro Glu Val Gln Phe Asn Trp
```

```
            145                 150                 155                 160
Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Gly Leu Pro Ser Ser Ile Glu Lys Thr Ile Ser Lys Ala Lys Gly
                210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Arg Leu Thr Val Asp Lys Ser Arg Trp Gln Glu Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 59
<211> LENGTH: 327
<212> TYPE: PRT
<213> ORGANISM: Artificial
<220> FEATURE:
<223> OTHER INFORMATION: Antibody 2
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 59

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Ser Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 60
<211> LENGTH: 327
<212> TYPE: PRT
<213> ORGANISM: Artificial
<220> FEATURE:
<223> OTHER INFORMATION: Antibody 3
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 60

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Cys Pro Ser Ser Pro Ala Pro
            100                 105                 110

Glu Phe Leu Gly Gly Pro Ser Val Phe Leu Phe Pro Pro Lys Pro Lys
        115                 120                 125
```

```
Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 61
<211> LENGTH: 330
<212> TYPE: PRT
<213> ORGANISM: Artificial
<220> FEATURE:
<223> OTHER INFORMATION: Antibody 48
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 61

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
```

```
                    115                 120                 125
Lys Pro Lys Asp Thr Leu Met Ile Ser Arg Thr Pro Glu Val Thr Cys
130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 62
<211> LENGTH: 327
<212> TYPE: PRT
<213> ORGANISM: Artificial
<220> FEATURE:
<223> OTHER INFORMATION: Antibody 28P
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 62

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Cys Pro Pro Cys Pro Ala Pro
            100                 105                 110
```

-continued

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 63
<211> LENGTH: 330
<212> TYPE: PRT
<213> ORGANISM: Artificial
<220> FEATURE:
<223> OTHER INFORMATION: Antibody 44P
<220> FEATURE:
<221> NAME/KEY: misc_feature
<222> LOCATION: (1)..(1)
<223> OTHER INFORMATION: Xaa is absent or alanine
<220> FEATURE:
<221> NAME/KEY: misc_feature
<222> LOCATION: (99)..(99)
<223> OTHER INFORMATION: Xaa is absent or glutamic acid

<400> SEQUENCE: 63

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

```
Arg Val Xaa Ser Lys Tyr Cys Pro Ala Ala Ala Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Glu Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 64
<211> LENGTH: 209
<212> TYPE: PRT
<213> ORGANISM: Artificial
<220> FEATURE:
<223> OTHER INFORMATION: IgG4 CH2 and CH3

<400> SEQUENCE: 64

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser Gln Glu Asp
            20                  25                  30

Pro Glu Val Gln Phe Asn Trp Tyr Val Asp Gly Val Glu Val His Asn
        35                  40                  45

Ala Lys Thr Lys Pro Arg Glu Glu Gln Phe Asn Ser Thr Tyr Arg Val
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Gly Leu Pro Ser Ser Ile Glu Lys
                85                  90                  95

Thr Ile Ser Lys Ala Lys Gly Gln Pro Arg Glu Pro Gln Val Tyr Thr
            100                 105                 110

Leu Pro Pro Ser Gln Glu Glu Met Thr Lys Asn Gln Val Ser Leu Thr
        115                 120                 125
```

Cys Leu Val Lys Gly Phe Tyr Pro Ser Asp Ile Ala Val Glu Trp Glu
            130                 135                 140

Ser Asn Gly Gln Pro Glu Asn Asn Tyr Lys Thr Thr Pro Pro Val Leu
145                 150                 155                 160

Asp Ser Asp Gly Ser Phe Phe Leu Tyr Ser Arg Leu Thr Val Asp Lys
                165                 170                 175

Ser Arg Trp Gln Glu Gly Asn Val Phe Ser Cys Ser Val Met His Glu
            180                 185                 190

Ala Leu His Asn His Tyr Thr Gln Lys Ser Leu Ser Leu Ser Leu Gly
        195                 200                 205

Lys

<210> SEQ ID NO 65
<211> LENGTH: 209
<212> TYPE: PRT
<213> ORGANISM: Artificial
<220> FEATURE:
<223> OTHER INFORMATION: IgG4 CH2 and IgG1 CH3

<400> SEQUENCE: 65

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser Gln Glu Asp
            20                  25                  30

Pro Glu Val Gln Phe Asn Trp Tyr Val Asp Gly Val Glu Val His Asn
        35                  40                  45

Ala Lys Thr Lys Pro Arg Glu Glu Gln Phe Asn Ser Thr Tyr Arg Val
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Gly Leu Pro Ser Ser Ile Glu Lys
                85                  90                  95

Thr Ile Ser Lys Ala Lys Gly Gln Pro Arg Glu Pro Gln Val Tyr Thr
            100                 105                 110

Leu Pro Pro Ser Arg Asp Glu Leu Thr Lys Asn Gln Val Ser Leu Thr
        115                 120                 125

Cys Leu Val Lys Gly Phe Tyr Pro Ser Asp Ile Ala Val Glu Trp Glu
            130                 135                 140

Ser Asn Gly Gln Pro Glu Asn Asn Tyr Lys Thr Thr Pro Pro Val Leu
145                 150                 155                 160

Asp Ser Asp Gly Ser Phe Phe Leu Tyr Ser Lys Leu Thr Val Asp Lys
                165                 170                 175

Ser Arg Trp Gln Gln Gly Asn Val Phe Ser Cys Ser Val Met His Glu
            180                 185                 190

Ala Leu His Asn His Tyr Thr Gln Lys Ser Leu Ser Leu Ser Pro Gly
        195                 200                 205

Lys

<210> SEQ ID NO 66
<211> LENGTH: 106
<212> TYPE: PRT
<213> ORGANISM: Artificial
<220> FEATURE:
<223> OTHER INFORMATION: Wild type Kappa constant light chain

<400> SEQUENCE: 66

Thr Val Ala Ala Pro Ser Val Phe Ile Phe Pro Pro Ser Asp Glu Gln

```
                1               5                  10                  15
Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 67
<211> LENGTH: 9
<212> TYPE: PRT
<213> ORGANISM: Artificial
<220> FEATURE:
<223> OTHER INFORMATION: Heavy chain IgD fragment

<400> SEQUENCE: 67

Ile Ile Ser Gly Cys Arg His Pro Lys
1               5

<210> SEQ ID NO 68
<211> LENGTH: 34
<212> TYPE: PRT
<213> ORGANISM: Artificial
<220> FEATURE:
<223> OTHER INFORMATION: Heavy chain IgD Hinge fragment
<220> FEATURE:
<221> NAME/KEY: misc_feature
<222> LOCATION: (1)..(1)
<223> OTHER INFORMATION: Xaa is absent or glutamic acid

<400> SEQUENCE: 68

Xaa Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr

<210> SEQ ID NO 69
<211> LENGTH: 9
<212> TYPE: PRT
<213> ORGANISM: Artificial
<220> FEATURE:
<223> OTHER INFORMATION: Heavy Chain IgM fragment

<400> SEQUENCE: 69

Leu Val Ser Cys Glu Asn Ser Pro Ser
1               5

<210> SEQ ID NO 70
<211> LENGTH: 7
<212> TYPE: PRT
<213> ORGANISM: Artificial
<220> FEATURE:
<223> OTHER INFORMATION: Heavy Chain IgM fragment

<400> SEQUENCE: 70

Glu Lys Asn Val Pro Leu Pro
```

<210> SEQ ID NO 71
<211> LENGTH: 11
<212> TYPE: PRT
<213> ORGANISM: Artificial
<220> FEATURE:
<223> OTHER INFORMATION: Heavy Chain IgM fragment
<220> FEATURE:
<221> NAME/KEY: misc_feature
<222> LOCATION: (1)..(1)
<223> OTHER INFORMATION: Xaa is absent or valine

<400> SEQUENCE: 71

Xaa Ile Ala Glu Leu Pro Pro Lys Val Ser Val
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic

<400> SEQUENCE: 72

Glu Ser Lys Tyr Cys Pro Pro Cys Pro Ser Pro Ala
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic

<400> SEQUENCE: 73

Asp Lys Thr His Thr
1               5

<210> SEQ ID NO 74
<211> LENGTH: 12
<212> TYPE: PRT
<213> ORGANISM: Artificial Sequence
<220> FEATURE:
<223> OTHER INFORMATION: Synthetic

<400> SEQUENCE: 74

Glu Ser Lys Tyr Cys Pro Pro Cys Pro Ser Cys Pro
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic

<400> SEQUENCE: 75

Glu Ser Lys Tyr Cys Asp Lys Cys Pro Ser Cys Pro
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic

<400> SEQUENCE: 76

Glu Ser Lys Tyr Cys Asp Lys Thr Cys Pro Ser Cys Pro
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Synthetic

<400> SEQUENCE: 77

Glu Ser Lys Tyr Cys Asp Lys Thr His Cys Pro Ser Cys Pro
1               5                   10

<210> SEQ ID NO 78
<211> LENGTH: 15
<212> TYPE: PRT
<213> ORGANISM: Artificial Sequence
<220> FEATURE:
<223> OTHER INFORMATION: Synthetic

<400> SEQUENCE: 78

Glu Ser Lys Tyr Cys Asp Lys Thr His Thr Cys Pro Ser Cys Pro
1               5                   10                  15

<210> SEQ ID NO 79
<211> LENGTH: 4
<212> TYPE: PRT
<213> ORGANISM: Artificial Sequence
<220> FEATURE:
<223> OTHER INFORMATION: Synthetic

<400> SEQUENCE: 79

Cys Pro Ser Cys
1

<210> SEQ ID NO 80
<211> LENGTH: 15
<212> TYPE: PRT
<213> ORGANISM: Artificial Sequence
<220> FEATURE:
<223> OTHER INFORMATION: Synthetic

<400> SEQUENCE: 80

Glu Ser Lys Tyr Cys Pro Pro Thr His Thr Cys Pro Ser Cys Pro
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic

<400> SEQUENCE: 81

Glu Ser Lys Tyr Cys Pro Pro Ala Ala Ala Cys Pro Ser Cys Pro
1               5                   10                  15

<210> SEQ ID NO 82
<211> LENGTH: 4
<212> TYPE: PRT
<213> ORGANISM: Artificial Sequence
<220> FEATURE:
<223> OTHER INFORMATION: Synthetic

<400> SEQUENCE: 82

Glu Ser Lys Tyr
1

<210> SEQ ID NO 83
<211> LENGTH: 4
<212> TYPE: PRT
<213> ORGANISM: Artificial Sequence
<220> FEATURE:
<223> OTHER INFORMATION: Synthetic

<400> SEQUENCE: 83

Glu Pro Lys Ser
1

<210> SEQ ID NO 84
<211> LENGTH: 4
<212> TYPE: PRT
<213> ORGANISM: Artificial Sequence
<220> FEATURE:
<223> OTHER INFORMATION: Synthetic

<400> SEQUENCE: 84

Glu Ser Lys Pro
1

<210> SEQ ID NO 85
<211> LENGTH: 4
<212> TYPE: PRT
<213> ORGANISM: Artificial Sequence
<220> FEATURE:
<223> OTHER INFORMATION: Synthetic

<400> SEQUENCE: 85

Glu Pro Lys Tyr
1

<210> SEQ ID NO 86
<211> LENGTH: 15
<212> TYPE: PRT
<213> ORGANISM: Artificial Sequence
<220> FEATURE:
<223> OTHER INFORMATION: Synthetic

<400> SEQUENCE: 86

Glu Pro Lys Ser Cys Asp Lys Thr His Thr Cys Pro Ser Cys Pro
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic

<400> SEQUENCE: 87

Glu Pro Lys Ser Cys Asp Lys Thr His Thr Cys Pro Pro Cys Pro
1               5                   10                  15